United States Patent
Essner et al.

(10) Patent No.: US 9,074,224 B2
(45) Date of Patent: Jul. 7, 2015

(54) METHODS AND COMPOSITIONS FOR TARGETED GENE MODIFICATION

(75) Inventors: Jeffrey J. Essner, Ames, IA (US); Hsin-Kai Liao, Ames, IA (US); Scott C. Fahrenkrug, Minneapolis, MN (US)

(73) Assignee: Recombinetics, Inc., Saint Paul, MN (US)

( * ) Notice: Subject to any disclaimer, the term of this patent is extended or adjusted under 35 U.S.C. 154(b) by 579 days.

(21) Appl. No.: 12/869,232

(22) Filed: Aug. 26, 2010

(65) Prior Publication Data

US 2011/0059160 A1    Mar. 10, 2011

Related U.S. Application Data

(63) Continuation of application No. PCT/US2010/004236, filed on Aug. 3, 2010.

(60) Provisional application No. 61/230,784, filed on Aug. 3, 2009.

(51) Int. Cl.
*C12N 11/02* (2006.01)
*C12N 15/09* (2006.01)
*C12N 15/90* (2006.01)
*C07K 14/00* (2006.01)
*A61K 48/00* (2006.01)

(52) U.S. Cl.
CPC .............. *C12N 15/90* (2013.01); *A61K 48/00* (2013.01); *C07K 14/00* (2013.01); *C07K 2319/09* (2013.01); *C07K 2319/81* (2013.01); *C12N 2770/14022* (2013.01); *C12N 2800/30* (2013.01)

(58) Field of Classification Search
CPC ........... C07K 2319/00; C07K 2319/09; C07K 2319/71; C07K 2319/80; C12N 15/00; C12N 15/09; C12N 11/00; C12N 11/02; C12N 2310/00; C12N 2320/00
USPC ........... 435/440, 455, 462, 463; 530/350, 812
See application file for complete search history.

(56) References Cited

U.S. PATENT DOCUMENTS

| | | | |
|---|---|---|---|
| 4,536,475 A | 8/1985 | Anderson | |
| 4,684,611 A | 8/1987 | Schilperoort et al. | |
| 4,873,191 A | 10/1989 | Wagner et al. | |
| 4,888,274 A | 12/1989 | Radding et al. | |
| 4,897,355 A | 1/1990 | Eppstein et al. | |
| 4,945,050 A | 7/1990 | Sanford et al. | |
| 4,946,787 A | 8/1990 | Eppstein et al. | |
| 5,049,386 A | 9/1991 | Eppstein et al. | |
| 5,061,620 A | 10/1991 | Tsukamoto et al. | |
| 5,142,047 A | 8/1992 | Summerton et al. | |
| 5,185,444 A | 2/1993 | Summerton et al. | |
| 5,510,473 A | 4/1996 | Camerino-Otero et al. | |
| 5,539,082 A | 7/1996 | Nielsen et al. | |
| 5,585,245 A | 12/1996 | Johnsson et al. | |
| 5,674,992 A | 10/1997 | Jagendorf et al. | |
| 5,681,559 A | 10/1997 | DiGiusto et al. | |
| 5,731,411 A | 3/1998 | Voloshin et al. | |
| 5,763,240 A | 6/1998 | Zarling et al. | |
| 5,773,571 A | 6/1998 | Nielsen et al. | |
| 5,789,538 A | 8/1998 | Rebar et al. | |
| 5,792,933 A | 8/1998 | Ma | |
| 5,843,780 A | 12/1998 | Thomson | |
| 5,866,121 A | 2/1999 | Coffino et al. | |
| 5,925,523 A | 7/1999 | Dove et al. | |
| 5,948,653 A | 9/1999 | Pati et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas, III et al. | |
| 6,200,759 B1 | 3/2001 | Dave et al. | |
| 6,200,806 B1 | 3/2001 | Thomson | |
| 6,242,568 B1 | 6/2001 | Barbas, III et al. | |
| 6,280,718 B1 | 8/2001 | Kaufman et al. | |
| 6,335,195 B1 | 1/2002 | Rodgers et al. | |
| 6,388,169 B1 | 5/2002 | Mahajan et al. | |
| 6,395,474 B1 | 5/2002 | Buchardt et al. | |
| 6,410,248 B1 | 6/2002 | Greisman et al. | |
| 6,451,968 B1 | 9/2002 | Egholm et al. | |
| 6,453,242 B1 | 9/2002 | Eisenberg et al. | |
| 6,479,626 B1 | 11/2002 | Kim et al. | |
| 6,489,458 B2 * | 12/2002 | Hackett et al. | ............... 536/23.2 |
| 6,498,458 B1 | 12/2002 | Chen | |
| 6,506,559 B1 | 1/2003 | Fire et al. | |
| 6,528,313 B1 | 3/2003 | LeMouellic et al. | |
| 6,528,314 B1 | 3/2003 | LeMouellic et al. | |
| 6,534,261 B1 | 3/2003 | Cox, III et al. | |
| 6,541,684 B1 | 4/2003 | Bowen et al. | |
| 6,548,741 B2 | 4/2003 | DeSousa et al. | |

(Continued)

FOREIGN PATENT DOCUMENTS

EP    1 308 516 A1    7/2003
WO    91/16024 A1    10/1991

(Continued)

OTHER PUBLICATIONS

Guo et al, Proc Natl Acad Sci 101(25):9205-9210, 2004.*
Clark et al, Genesis 39:225-233, 2004.*
Shcherbakova et al., "Overexpression of bacterial RecA protein stimulates homologous recombination in somatic mammalian cells", Mutation Research, 45:65-71 (2000).
International Search Report (PCT/US2010/044236) dated Apr. 12, 2011—10 pages.
Aboussekhra et al., "Semidominant suppressors of Srs2 helicase mutations of *Saccharomyces cerevisiae* map in the RAD51 gene, whose sequence predicts a protein with similarities to procaryotic RecA proteins", Mol. Cell. Biol., 72:3224-3234 (Jul. 1992).

(Continued)

*Primary Examiner* — Kevin Hill
(74) *Attorney, Agent, or Firm* — Dardi & Herbert, PLLC; Curtis B. Herbert

(57) ABSTRACT

Disclosed herein are methods and compositions for gene targeting utilizing fusion molecules comprising a recombinase domain and a sequence-specific DNA-binding domain.

13 Claims, 10 Drawing Sheets

(56) References Cited

U.S. PATENT DOCUMENTS

| | | |
|---|---|---|
| 6,555,692 B1 | 4/2003 | Dervan |
| 6,569,681 B1 | 5/2003 | Ivanov |
| 6,602,711 B1 | 8/2003 | Thomson et al. |
| 6,610,512 B1 | 8/2003 | Barbas |
| 6,613,568 B2 | 9/2003 | Kaufman et al. |
| 6,645,489 B2 | 11/2003 | Pykett et al. |
| 6,667,064 B2 | 12/2003 | Surette |
| 6,686,515 B1 | 2/2004 | Lassner et al. |
| 6,720,478 B1 | 4/2004 | Mahajan et al. |
| 6,733,970 B2 | 5/2004 | Choo et al. |
| 6,746,838 B1 | 6/2004 | Choo et al. |
| 6,774,213 B1 | 8/2004 | Roca |
| 6,790,941 B2 | 9/2004 | Barbas, III et al. |
| 6,794,136 B1 | 9/2004 | Eisenberg et al. |
| 6,809,183 B2 | 10/2004 | Mahajan |
| 6,824,978 B1 | 11/2004 | Cox, III et al. |
| 6,866,997 B1 | 3/2005 | Choo et al. |
| 6,887,706 B2 | 5/2005 | Zhang et al. |
| 6,903,185 B2 * | 6/2005 | Kim et al. .................. 530/300 |
| 6,905,857 B2 | 6/2005 | Bowen et al. |
| 6,933,113 B2 | 8/2005 | Case et al. |
| 7,005,252 B1 | 2/2006 | Thomson |
| 7,029,847 B2 | 4/2006 | Joung et al. |
| 7,029,913 B2 | 4/2006 | Thomson |
| 7,034,117 B2 | 4/2006 | Mahajan et al. |
| 7,067,617 B2 | 6/2006 | Barbas, III et al. |
| 7,144,734 B2 | 12/2006 | Court et al. |
| 7,160,682 B2 | 1/2007 | Hackett et al. |
| 7,176,007 B2 | 2/2007 | Cox et al. |
| 7,199,218 B1 | 4/2007 | Bronner et al. |
| 7,199,281 B2 | 4/2007 | Murray et al. |
| 7,229,767 B2 | 6/2007 | Kmiec et al. |
| 7,294,494 B2 | 11/2007 | Roca |
| 7,297,491 B2 | 11/2007 | Joung et al. |
| 7,361,641 B2 | 4/2008 | Calos |
| 7,378,485 B2 | 5/2008 | Burchardt et al. |
| 7,416,847 B1 | 8/2008 | Lindqvist et al. |
| 7,527,966 B2 | 5/2009 | Cooper et al. |
| 7,732,585 B2 | 6/2010 | Calos |
| 7,919,583 B2 | 4/2011 | Hackett et al. |
| 2002/0064802 A1 | 5/2002 | Raschke et al. |
| 2002/0081603 A1 | 6/2002 | Wolffe et al. |
| 2002/0165356 A1 | 11/2002 | Barbas, III et al. |
| 2003/0108880 A1 | 6/2003 | Rebar et al. |
| 2003/0119023 A1 | 6/2003 | Choo et al. |
| 2003/0217376 A1 | 11/2003 | Ebens, Jr. et al. |
| 2004/0137624 A1 | 7/2004 | Lowe |
| 2004/0197892 A1 | 10/2004 | Moore et al. |
| 2005/0112620 A1 | 5/2005 | Chan |
| 2005/0233993 A1 * | 10/2005 | Kadonaga et al. .......... 514/44 |
| 2007/0009948 A1 | 1/2007 | Choo et al. |
| 2007/0009962 A1 | 1/2007 | Choo et al. |
| 2007/0031380 A1 | 2/2007 | Hackett et al. |
| 2007/0154989 A1 | 7/2007 | Barbas, III |
| 2007/0213269 A1 | 9/2007 | Barbas, III et al. |
| 2010/0146655 A1 | 6/2010 | Fahrenkrug et al. |

FOREIGN PATENT DOCUMENTS

| | | |
|---|---|---|
| WO | 91/17424 A1 | 11/1991 |
| WO | 96/32496 A1 | 10/1996 |
| WO | 99/07206 A1 | 8/1997 |
| WO | 98/53059 A1 | 5/1998 |
| WO | 98/44350 A1 | 10/1998 |
| WO | 99/16890 A1 | 4/1999 |
| WO | 99/40210 A1 | 8/1999 |
| WO | 01/16024 A1 | 3/2001 |
| WO | 01/53480 A1 | 7/2001 |
| WO | 01/60970 A2 | 8/2001 |
| WO | 02/057293 A2 | 7/2002 |
| WO | 03/016496 A2 | 2/2003 |
| WO | 2006/036975 A2 | 4/2006 |
| WO | 2008006028 | 1/2008 |

OTHER PUBLICATIONS

Akopian et al., Chimeric recombinases with designed DNA sequence recognition, Proc. Natl. Acad. Sci. USA, 100:8688-8691 (Jul. 22, 2003).

Baliga et al., "RecA.oligonucleotide filaments bind in the minor groove of double-stranded DNA", Proc. Natl. Acad. Sci. USA, 92(22):10393-10397 (Oct. 24, 1995).

Basile et al., "Nucleotide sequence and transcriptional regulation of the yeast recombinational repair gene RAD51", Mol. Cell. Biol., 12(7): 3235-3246 (Jul. 1992).

Beerli et al., "Engineering polydactyl zinc-finger transcription factors", Nat. Biotechnol., 20(2):135-141 (Feb. 2002).

Bertrand et al., Increase of spontaneous intrachromosomal homologous recombination in mammalian cells expressing a mutant p53 protein, Oncogene, 14(9):1117-1122 (Mar. 6, 1997).

Bevan et al., "T-DNA of the Agrobacterium Ti and Ri plasmids", Annu. Rev. Genet. 16:357-384 (1982).

Bevan et al., "The structure and transcription start site of a major potato tuber protein gene", Nucleic Acids Res., 14(11):4625-4638 (Jun. 11, 1986).

Bibikova et al., "Targeted chromosomal cleavage and mutagenesis in *Drosophila* using zinc-finger nucleases", Genetics, 161(3):1169-1175 (Jul. 2002).

Biet et al., "Stimulation of RecA-mediated D-Loop Formation by Oligonucleotide-Directed Triple-Helix Formation: Guided Homologous Recombination (GOREC)", Biochemistry, 40:1779-1786 (2001).

Boehden et al., "p53 mutated in the transactivation domain retains regulatory functions in homology-directed double-strand break repair" Oncogene, 22(26):4111-4117 (Jun. 26, 2003).

Bray, "Expression of the β-subunit of β-conglycinin in seeds of transgenic plants", Planta, 172(3):364-370 (1987).

Brendel et al., "Evolutionary comparisons of RecA-like proteins across all major kingdoms of living organisms", J. Mol. Evol., 44(5):528-541 (May 1997).

Brisson et al, "Expression of a bacterial gene in plants by using a viral vector", Nature, 310:511-514 (Aug. 9, 1984).

Capecchi, "Altering the genome by homologous recombination", Science, 244(4910):1288-1292 (Jun. 16, 1989).

Cassuto et al., "Partial purification of an activity from human cells that promotes homologous pairing and the formation of heteroduplex DNA in the presence of ATP", Mol. Gen. Genet., 208(1-2):10-14 (Jun. 1987).

Chang et al., "Modification of DNA ends can decrease end joining relative to homologous recombination in mammalian cells", Proc. Natl. Acad. Sci. USA, 84(14):4959-4963 (Jul. 1987).

Choo et al., "Advances in zinc finger engineering", Curr. Opin. Struct. Biol., 10(4):411-416 (Aug. 2000).

Choulika et al., "Induction of homologous recombination in mammalian chromosomes by using the I-Scel system of *Saccharomyces cerevisiae*", Mol. Cell. Biol., 15(4):1968-1973 (Apr. 1995).

Christensen et al., "Maize polyubiquitin genes: structure, thermal perturbation of expression and transcript splicing, and promoter activity following transfer to protoplasts by electroporation", Plant Mol. Biol., 18(4):675-689 (Feb. 1992).

Cibelli et al., "Cloned transgenic calves produced from nonquiescent fetal fibroblasts", Science, 280(5367):1256-1258 (May 22, 1998).

Clark et al., "Isolation, DNA sequence, and regulation of a *Saccharomyces cerevisiae* gene that encodes DNA strand transfer protein alpha", Molec. Cell. Biol., 11(5):2576-2582 (May 1991).

Coruzzi et al., "Tissue-specific and light-regulated expression of a pea nuclear gene encoding the small subunit of ribulose-1,5-bisphosphate carboxylase", EMBO J., 3(8):1671-1679 (Aug. 1984).

Cox, "Historical overview: searching for replication help in all of the rec places", Proc. Natl. Acad. Sci. USA, 98(15):8173-8180 (Jul. 17, 2001).

Cui et al., "RecA-mediated, targeted mutagenesis in zebrafish", Marine Biotechnol., 5(2):174-184 (Mar.-Apr. 2003).

(56) References Cited

OTHER PUBLICATIONS

Desjarlais et al., "Use of a zinc-finger consensus sequence framework and specificity rules to design specific DNA binding proteins", Proc. Natl. Acad. Sci. USA, 90(6):2256-2260 (Mar. 15, 1993).
Desjarlais et al., "Length-encoded multiplex binding site determination: application to zinc finger proteins", Proc. Natl. Acad. Sci. USA 91(23):11099-11103 (Nov. 8, 1994).
D'Halluin et al., "Transgenic maize plants by tissue electroporation", Plant Cell 4(12):1495-1505 (Dec. 1992).
Dimos et al., "Induced pluripotent stem cells generated from patients with ALS can be differentiated into motor neurons", Science 321(5893):1218-1221 (Aug. 29, 2008).
Donoho et al. "Analysis of gene targeting and intrachromosomal homologous recombination stimulated by genomic double-strand breaks in mouse embryonic stem cells", Mol. Cell. Biol., 18(7):4070-4078 (Jul. 1998).
Dunderdale et al., "Formation and resolution of recombination intermediates by *E. coli* RecA and RuvC proteins", Nature, 354(6354):506-510 (Dec. 19-26, 1991).
Dupuy et al., "Mammalian germ-line transgenesis by transposition", Proc Natl Acad Sci USA, 99(7):4495-4499 (Apr. 2, 2002).
Dykstra et al., "Cloning and characterization of DST2, the gene for DNA strand transfer protein beta from *Saccharomyces cerevisiae*", Molec. Cell. Biol., 11(5):2583-2592 (May 1991).
Eisen et al., "A recombinase from *Drosophila melanogaster* embryos", Proc. Natl. Acad. Sci. USA, 85(20)1481-7485 (Oct. 1988).
Escriou et al., "NLS bioconjugates for targeting therapeutic genes to the nucleus", Advanced Drug Delivery Reviews, 55(2):295-306 (Feb. 10, 2003).
Fields et al., "A novel genetic system to detect protein-protein interactions", Nature, 340(6230):245-246 (Jul. 20, 1989).
Fishel et al., "Identification of homologous pairing and strand-exchange activity from a human tumor cell line based on Z-DNA affinity chromatography", Proc. Natl. Acad. Sci. USA, 85(1):36-40 (Jan. 1988).
Fromm et al., "Expression of genes transferred into monocot and dicot plant cells by electroporation", Proc. Nat. Acad. Sci. USA, 82(17):5824-5828 (Sep. 1985).
Fujisawa et al., "Sequence of the T4 recombination gene, uvsX, and its comparison with that of the recA gene of *Escherichia coil*", Nucl. Acids Res., 13(20):7473-7481 (1985).
Ganea et al., "Characterization of an ATP-dependent DNA strand transferase from human cells", Mol. Cell Biol. 7(9):3124-3130 (Sep. 1987).
Goff et al., "Transactivation of anthocyanin biosynthetic genes following transfer of B regulatory genes into maize tissues", EMBO J. 9(8):2517-2522 (Aug. 1990).
Gordon-Kamm et al., "Transformation of Maize Cells and Regeneration of Fertile Transgenic Plants", Plant Cell 2(7):603-618 (Jul. 1990).
Gossen et al., "Tight control of gene expression in mammalian cells by tetracycline-responsive promoters", Proc. Natl. Acad. Sci USA, 89(12):5547-5551 (Jun. 15, 1992).
Gribskov et al., "Sigma factors from *E. coli, B. subtilis*, phage SP01, and phage T4 are homologous proteins", Nucl. Acids Res., 14(6):6745-6763 (Aug. 26, 1986).
Guatelli et al., "Isothermal, in vitro amplification of nucleic acids by a multienzyme reaction modeled after retroviral replication", Proc. Natl. Acad. Sci. USA, 87(5):1874-1878 (Mar. 1990).
Gurley et al., "Upstream sequences required for efficient expression of a soybean heat shock gene", Cell. Biol., 6(2):559-565 (Feb. 1986).
Hacien-Bey-Abina et al., "LMO2-associated clonal T cell proliferation in two patients after gene therapy for SCID-X1", Science, 302(5644):415-419 (Oct. 24, 2003).
Halbrook et al., "Purification and characterization of a DNA-pairing and strand transfer activity from mitotic *Saccharomyces cerevisiae*", J. Biol. Chem., 264(35):21403-21412 (Dec. 15, 1989).

Hernalsteens et al., "An Agrobacterium-transformed cell culture from the monocot *Asparagus officinalis*", EMBO J., 3(13):3039-3041 (Dec. 20, 1984).
Hoeijmakers, "Genome maintenance mechanisms for preventing cancer", Nature, 411(6835):366-374 (May 17, 2001).
Horsch et al., "A simple and general method for transferring genes into plants", Science, 227(4691):1229-1231 (Mar. 8, 1985).
Hsieh et al., "Formation of joint DNA molecules by two eukaryotic strand exchange proteins does not require melting of a DNA duplex", J. Biol. Chem., 264(9):5089-5097 (Mar. 25, 1989).
Isalan et al., "A rapid, generally applicable method to engineer zinc fingers illustrated by targeting the HIV-1 promoter", Nature Biotechnol., 19(7):656-660 (Jul. 2001).
Ishiwatari et al., "Rice phloem thioredoxin h has the capacity to mediate its own cell-to-cell transport through plasmodesmata", Planta 205(1):12-22 (May 1998).
Janz et al., "Wild-type p53 inhibits replication-associated homologous recombination", Oncogene, 21(38):5929-5933 (Aug. 29, 2002).
Jefferson, "Assaying chimeric genes in plants: The GUS gene fusion system", Plant Molec Biol. Rep., 5(4):387-405 (1987).
Kaeppler et al., "Silicon carbide fiber-mediated DNA delivery into plant cells", Plant Cell Reports, 9(8):415-418 (1990).
Kay et al., "Duplication of CaMV 35S Promoter Sequences Creates a Strong Enhancer for Plant Genes", Science 236(4806):1299-1302 (Jun. 5, 1987).
Klein et al., "Transfer of foreign genes into intact maize cells with high-velocity microprojectiles", Proc. Nat. Acad. Sci. USA, 85(12):4305-4309 (Jun. 1988).
Kolodner et al., "Purification and characterization of an activity from *Saccharomyces cerevisiae* that catalyzes homologous pairing and strand exchange", Proc. Natl. Acad. Sci. USA, 84(7):5560-5564 (Aug. 1987).
Lamason et al., "SLC24A5, a putative cation exchanger, affects pigmentation in zebrafish and humans", Science, 310(5755):1782-1786 (Dec. 16, 2005).
Lavitrano et al., "Efficient production by sperm-mediated gene transfer of human decay accelerating factor (hDAF) transgenic pigs for xenotransplantation", Proc. Natl. Acad. Sci. USA, 99(22):14230-14235 (Oct. 29, 2002).
Lavitrano et al. "Sperm-mediated gene transfer", Reprod. Fert. Develop., 18:19-23 (2006).
Lo, "Transformation by iontophoretic microinjection of DNA: multiple integrations without tandem insertions", Mol. Cell. Biol. 3(10):1803-1814 (Oct. 1983).
Lowenhaupt et al., "*Drosophila melanogaster* strand transferase. A protein that forms heteroduplex DNA in the absence of both ATP and single-strand DNA binding protein", J. Biol. Chem., 264(3):20568-20575 (Dec. 5, 1989).
Madiraju et al., "Properties of a mutant recA-encoded protein reveal a possible role for *Escherichia coli* recF-encoded protein in genetic recombination", Proc. Natl. Acad. Sci. USA, 85(18):6592-6596 (Sep. 1988).
Maeder et al., "Rapid "open-source" engineering of customized zinc-finger nucleases for highly efficient gene modification", Mol. Cell 312):294-301 (Jul. 25, 2008).
Maeshima et al., "RAD51 homologues in *Xenopus laevis*: two distinct genes are highly expressed in ovary and testis", Gene, 160:195-200 (1995).
Mapp et al., "Activation of gene expression by small molecule transcription factors", Proc. Natl. Acad. Sci. USA, 97(8):3930-3935 (Apr. 11, 2000).
McCarthy et al., "Sensitive homologous recombination strand-transfer assay: partial purification of a *Drosophila melanogaster* enzyme and detection of sequence effects on the strand-transfer of RecA protein", Proc. Natl. Acad. Sci. USA, 85(16):5854-5858 (Aug. 1988).
McElroy et al., "Isolation of an efficient actin promoter for use in rice transformation", Plant Cell, 2(2):163-171 (Feb. 1990).
Medberry et al., "The Commenlina yellow mottle virus promoter is a strong promoter in vascular and reproductive tissues", Plant Cell 4(2):195-192 (Feb. 1992).
Mekeel et al., "Inactivation of p53 results in high rates of homologous recombination", Oncogene, 14(15):1847-1857 (Apr. 17, 1997).

(56) References Cited

OTHER PUBLICATIONS

Miller et al., "Repetitive zinc-binding domains in the protein transcription factor IIIA from *Xenopus oocytes*", EMBO J., 4(6):1609-1614 (Jun. 1985).
Moore et al., "Purification and characterization of a protein from human cells which promotes homologous pairing of DNA", J. Biol. Chem., 265(19):11108-11117 (Jul. 5, 1990).
Moore et al., "The human homologous pairing HPP-1 is specifically stimulated by the cognate single-stranded binding protein hRP-A", Proc. Natl. Acad. Sci. U.S.A, 88(20):9067-9071 (Oct. 15, 1991).
Moore et al., "Design of polyzinc finger peptides with structured linkers", Proc. Natl. Acad. Sci. USA, 98(4):1432-1436 (Feb. 13, 2001).
Moore et al., "Improved DNA binding specificity from polyzinc finger peptides by using strings of two-finger units", Proc. Natl. Acad. Sci. USA, 98(4):1437-1441 (Feb. 13, 2001).
Morita et al., "A mouse homolog of the *Escherichia coli* recA and *Saccharomyces cerevisiae* RAD51 genes", Proc. Natl. Acad. Sci. USA, 90(14):6577-6580 (Jul. 15, 1993).
Muller-Rober et al., "One of two different ADP-glucose pyrophosphorylase genes from potato responds strongly to elevated levels of sucrose", Mol. Gen. Genet., 224(1):136-146 (1990).
Neering et al., "Transduction of primitive human hematopoietic cells with recombinant adenovirus vectors", Blood, 88(4):1147-1155 (Aug. 15, 1996).
Nehls et al., "Two genetically separable steps in the differentiation of thymic epithelium", Science, 272(5263):886-889 (May 10, 1996).
Nielsen et al., "Sequence-selective recognition of DNA by strand displacement with a thymine-substituted polyamide", Science 254(5037):1497-1500 (Dec. 6, 1991).
Oligino et al., "Drug inducible transgene expression in brain using a herpes simplex virus vector", Gene Ther., 5(4):491-496 (Apr. 1998).
Oparka et al., "Gating of epidermal plasmodesmata is restricted to the leading edge of expanding infection sites of tobacco mosaic virus (TMV)", Plant J., 12(4):781-789 (Oct. 1997).
Ow et al., "Transient and stable expression of the firefly luciferase gene in plant cells and transgenic plants", Science, 234:856-859 (Nov. 14, 1986).
Pabo et al., "Transcription factors: structural families and principles of DNA recognition", Ann. Rev. Biochem., 61:1053-1095 (1992).
Pabo et al., "Design and selection of novel Cys2His2 zinc finger proteins", Ann. Rev. Biochem. 70:313-340 (2001).
Palva et al., "Secretion of interferon by *Bacillus subtilis*", Gene, 22(2-3):229-235 (May-Jun. 1983).
Paskcowski et al., "Direct gene transfer to plants", EMBO J., 3(12):2717-2722 (Dec. 1, 1984).
Potrykus et al., "Molecular and general genetics of a hybrid foreign gene introduced into tobacco by direct gene transfer", Molec. Gen. Genet., 199(2):169-177 (1985).
Reiss et al., "RecA protein stimulates homologous recombination in plants", Proc. Natl. Acad. Sci. USA, 93(7):3094-3098 (Apr. 2, 1996).
Reiss et al., "RecA stimulates sister chromatid exchange and the fidelity of double-strand break repair, but not gene targeting, in plants transformed with Agrobacterium", Proc. Natl. Acad. Sci. USA, 97(7):3358-3363 (Mar. 28, 2000).
Rendahl et al., "Regulation of gene expression in vivo following transduction by two separate rAAV vectors", Nature Biotechnol., 16(8):757-761 (Aug. 1998).
Riggs et al., "Stable transformation of tobacco by electroporation: evidence for plasmid concatenation", Proc. Natl. Acad. Sci USA, 83(15):5602-5606 (Aug. 1986).
Robu et al., "Situational repair of replication forks: roles of RecG and RecA proteins", J. Biol. Chem., 279(12):10973-10981 (Mar. 19, 2004).
Roca et al., "The RecA protein: structure and function", Crit. Rev. Biochem. Molec. Biol., 25(6):415-456 (1990).
Rouet et al., "Introduction of double-strand breaks into the genome of mouse cells by expression of a rare-cutting endonuclease", Mol. Cell. Biol., 14(12):8096-8106 (Dec. 1994).
Saintigny et al., "Mutant p53 proteins stimulate spontaneous and radiation-induced intrachromosomal homologous recombination independently of the alteration of the transactivation activity and of the G1 checkpoint", Oncogene, 18(24):3553-3563 (Jun. 17, 1999).
Sanger et al., "Characteristics of a strong promoter from figwort mosaic virus: comparison with the analogous 35S promoter from cauliflower mosaic virus and the regulated mannopine synthase promoter", Plant Mol. Biol., 14(3):433-443 (Mar. 1990).
Santa Cruz et al., "Cell-to-cell and phloem-mediated transport of potato virus X. The role of virions", Plant Cell, 10(4):495-510 (Apr. 1998).
Segal et al., "Custom DNA-binding proteins come of age: polydactyl zinc-finger proteins", Curr. Opin. Biotechnol., 12(6):632-637 (2001).
Shimamoto et al. "Fertile transgenic rice plants regenerated from transformed protoplasts", Nature, 338(6212):274-276 (Mar. 16, 1989).
Shinohara et al., "Cloning of human, mouse and fission yeast recombination genes homologous to RAD51 and recA", Nature Genet. 4(3):239-243 (Jul. 1993).
Smith et al., "Comparison of biosequences", Advances in Applied Mathematics 2(4):482-489 (Dec. 1981).
Streisinger et al., "Clonal origins of cells in the pigmented retina of the zebrafish eye", Dev. Biol., 131(1):60-69 (Jan. 1989).
Sugino et al., "ATP-independent DNA strand transfer catalyzed by protein(s) from meiotic cells of the yeast *Saccharomyces cerevisiae*", Proc. Natl. Acad, Sci. USA, 85(11): 3683-3687 (Jun. 1988).
Takahashi et al., "Characterization of zebrafish Rad52 and replication protein A for oligonucleotide-mediated mutagenesis", Nucleic Acids Res., 33(13):e120 (2005).
Takamatsu et al., "Expression of bacterial chloramphenicol acetyltransferase gene in tobacco plants mediated by TMV-RNA", EMBO J. 6(2):307-311 (Feb. 1987).
Tauchi et al., "Nijmegen breakage syndrome gene, NBS1, and molecular links to factors for genome stability", Oncogene, 21(58):8967-8980 (Dec. 16, 2002).
Tishkoff et al., "Molecular and genetic analysis of the gene encoding the *Saccharomyces cerevisiae* strand exchange protein Sep1", Molec. Cell. Biol., 11(5):2593-2608 (May 1991).
Uhlin et al., "Overproduction of the *Escherichia coli* recA protein without stimulation of its proteolytic activity", J. Bacteriol., 148(1):386-390 (Oct. 1981).
Urnov et al., "Highly efficient endogenous human gene correction using designed zinc-finger nucleases", Nature, 435(7042):646-651 (Jun. 2, 2005).
Valerie et al., "Regulation and mechanisms of mammalian double-strand break repair", Oncogene, 22(37):5792-5812 (Sep. 1, 2003).
Van Der Putten et al., "Efficient insertion of genes into the mouse germ line via retroviral vectors", Proc. Natl. Acad. Sci. USA, 82(18):6148-1652 (Sep. 1985).
Wakayama et al., "Full-term development of mice from enucleated oocytes injected with cumulus cell nuclei", Nature, 394(6691):369-374 (Jul. 23, 1998).
Wang et al., "Positive and negative regulation of gene expression in eukaryotic cells with an inducible transcriptional regulator", Gene Ther., 4(5):432-441(May 1997).
Wang et al., "Dimerization of zinc fingers mediated by peptides evolved in vitro from random sequences", Proc. Natl. Acad. Sci. USA 9617):9568-9573 (Aug. 17, 1999).
Weiss, "Hot prospect for new gene amplifier", Science, 254(5036):1292-1293 (Nov. 29, 1991).
Wilmut et al., "Viable offspring derived from fetal and adult mammalian cells", Nature, 385(6619):810-813 (Feb. 27, 1997).
Yanez et al., "Therapeutic gene targeting", Gene Therapy, 5(2):149-159 (Feb. 1998).
Yanez et al., "Gene targeting is enhanced in human cells overexpressing hRAD51", Gene Ther., 6(7):1282-1290 (Jul. 1999).
Yin et al., "The regulatory regions of the rice tungro bacilliform virus promoter and interacting nuclear factors in rice (*Oryza sativa* L.)" Plant J., 7(6):969-980 (Jun. 1995).

(56) References Cited

OTHER PUBLICATIONS

Yu et al., "Induced pluripotent stem cell lines derived from human somatic cells", Science, 318(5858): 1917-1920 (Dec. 21, 2007).

Shcherbakova et al., "Overexpression of Bacterial RecA Protein Stimulates Homologous Recombination in Somatic Mammalian Cells", Mutation Ressearch, 459:65-71 (Oct. 22, 1999).

Liao et al. "Use of RecA Fusion Proteins to Induce Genomic Modifications in Zebrafish", Nucleic Acids Research, 39(10):4166-4179 (Dec. 31, 2010).

Supplementary European Search Report and Written Opinion from corresponding PCT Application No. PCT/US2010/044236, 11 pages, dated Jan. 8, 2013.

* cited by examiner

FIG. 1

Amino acid sequence of NLS/RecA/Gal4 (SEQ ID NO:3)

MPPKKKRKVEDPKMAIDENKQKALAAALGQIEKQFGKGS
IMRLGEDRSMDVETISTGSLSLDIALGAGGLPMGRIVEIYG
PESSGKTTLTLQVIAAAQREGKTCAFIDAEHALDPIYARKL
GVDIDNLLCSQPDTGEQALEICDALARSGAVDVIVVDSVA
ALTPKAEIEGEIGDSHMGLAARMMSQAMRKLAGNLKQSN
TLLIFINQIRMKIGVMFGNPETTTGGNALKFYASVRLDIRR
IGAVKEGENVVGSETRVKVVKNKIAAPFKQAEFQILYGEG
INFYGELVDLGVKEKLIEKAGAWYSYKGEKIGQGKANAT
AWLKDNPETAKEIEKKVRELLLSNPNSTPDFSVDDSEGVA
ETNEDFASMKLLSSIEQACDICRLKKLKCSKEKPKCAKCL
KNNWECRYSPKTKRSPLTRAHLTEVESRLERLEQLFLLIFP
REDLDMILKMDSLQDIKALLTGLFVQDNVKDAVTDRLA
SVETDMPLTLRQHRISATSSSEESSNKGQRQLTVSAAALE
HHHHHHHH 1-13 aa: NLS
14-366 aa: RecA
369-515 aa: Gal4
521-528 aa: His tag
other aa: linker

FIG. 2

Nucleotide sequence encoding NLS/RecA/Gal4 (SEQ ID NO:4)

atgccacctaaaaagaagagaaaggtagaagaccccaagatggctatcgacgaaaacaaacagaaagcgttggcggcagca
ctgggccagattgagaaacaatttggtaaaggctccatcatgcgcctgggtgaagaccgttccatggatgtggaaaccatctcta
ccggttcgctttcactggatatcgcgcttggggcaggtggtctgccgatgggccgtatcgtcgaaatctacggaccggaatcttc
cggtaaaaccacgctgacgctgcaggtgatcgccgcagcgcagcgtgaaggtaaaacctgtgcgtttatcgatgctgaacacg
cgctggacccaatctacgcacgtaaactgggcgtcgatatcgataacctgctgtgctcccagccggacaccggcgagcaggc
actggaaatctgtgacgccctggcgcgttctggcgcagtagacgttatcgtcgttgactccgtggcggcactgacgccgaaagc
ggaaatcgaaggcgaaatcggcgactctcacatgggccttgcggcacgtatgatgagccaggcgatgcgtaagctggcgggt
aacctgaagcagtccaacacgctgctgatcttcatcaaccagatccgtatgaaaattggtgtgatgttcggtaacccggaaacca
ctaccggtggtaacgcgctgaaattctacgcctctgttcgtctcgacatccgtcgtatcggcgcggtgaaagagggcgaaaacg
tggtgggtagcgaaacccgcgtgaaagtggtgaagaacaaaatcgctgcgccgtttaaacaggctgaattccagatcctctacg
gcgaaggtatcaacttctacggcgaactggttgacctgggcgtaaaagagaagctgatcgagaaagcaggcgcgtggtacag
ctacaaaggtgagaagatcggtcagggtaaagcgaatgcgactgcctggctgaaagataacccggaaaccgcgaaagagat
cgagaagaaagtacgtgagttgctgctgagcaacccgaactcaacgccggatttctctgtagatgatagcgaaggcgtagcag
aaactaacgaagattttgctagcatgaagctactgtcttctatcgaacaagcatgcgatatttgccgacttaaaaagctcaagtgct
ccaaagaaaaaccgaagtgcgccaagtgtctgaagaacaactgggagtgtcgctactctcccaaaaccaaaaggtctccgctg
actagggcacatctgacagaagtggaatcaaggctagaaagactggaacagctatttctactgattttcctcgagaagaccttga
catgattttgaaaatggattctttacaggatataaaagcattgttaacaggattatttgtacaagataatgtgaataaagatgccgtca
cagatagattggcttcagtggagactgatatgcctctaacattgagacagcatagaataagtgcgacatcatcatcggaagagag
tagtaacaaaggtcaaagacagttgactgtatcggcggccgcactcgagcaccaccaccaccaccaccac

FIG. 3

Amino acid sequence of NLS/RecA (SEQ ID NO:5)

```
M P P K K K R K V E D P K M A I D E N K Q K A L A A A L G Q
I E K Q F G K G S I M R L G E D R S M D V E T I S T G S L S
L D I A L G A G G L P M G R I V E I Y G P E S S G K T T L T
L Q V I A A A Q R E G K T C A F I D A E H A L D P I Y A R K
L G V D I D N L L C S Q P D T G E Q A L E I C D A L A R S G
A V D V I V V D S V A A L T P K A E I E G E I G D S H M G L
A A R M M S Q A M R K L A G N L K Q S N T L L I F I N Q I R
M K I G V M F G N P E T T T G G N A L K F Y A S V R L D I R
R I G A V K E G E N V V G S E T R V K V V K N K I A A P F K
Q A E F Q I L Y G E G I N F Y G E L V D L G V K E K L I E K
A G A W Y S Y K G E K I G Q G K A N A T A W L K D N P E T A
K E I E K K V R E L L L S N P N S T P D F S V D D S E G V A
E T N E D F A S A A A L E H H H H H H H H
```

(SEQ ID NO:5)

FIG. 4

Amino acid sequence of NLS/RecA (SEQ ID NO:6)

atgccacctaaaaagaagagaaaggtagaagaccccaagatggctatcgacgaaaacaa
acagaaagcgttggcggcagcactgggccagattgagaaacaatttggtaaaggctcca
tcatgcgcctgggtgaagaccgttccatggatgtggaaaccatctctaccggttcgctt
tcactggatatcgcgcttggggcaggtggtctgccgatgggccgtatcgtcgaaatcta
cggaccggaatcttccggtaaaaccacgctgacgctgcaggtgatcgccgcagcgcagc
gtgaaggtaaaacctgtgcgtttatcgatgctgaacacgcgctggacccaatctacgca
cgtaaactgggcgtcgatatcgataacctgctgtgctcccagccggacaccggcgagca
ggcactggaaatctgtgacgccctggcgcgttctggcgcagtagacgttatcgtcgttg
actccgtggcggcactgacgccgaaagcggaaatcgaaggcgaaatcggcgactctcac
atgggccttgcggcacgtatgatgagccaggcgatgcgtaagctggcgggtaacctgaa
gcagtccaacacgctgctgatcttcatcaaccagatccgtatgaaaattggtgtgatgt
tcggtaacccggaaaccactaccggtggtaacgcgctgaaattctacgcctctgttcgt
ctcgacatccgtcgtatcggcgcggtgaaagagggcgaaaacgtggtgggtagcgaaac
ccgcgtgaaagtggtgaagaacaaaatcgctgcgccgtttaaacaggctgaattccaga
tcctctacggcgaaggtatcaacttctacggcgaactggttgacctgggcgtaaaagag
aagctgatcgagaaagcaggcgcgtggtacagctacaaaggtgagaagatcggtcaggg
taaagcgaatgcgactgcctggctgaaagataacccggaaccgcgaaagagatcgaga
agaaagtacgtgagttgctgctgagcaacccgaactcaacgccggatttctctgtagat
gatagcgaaggcgtagcagaaactaacgaagattttgcggccgcactcgagcaccacca
ccaccaccaccac FIG. 5
A. NLS-RecA-Gal4
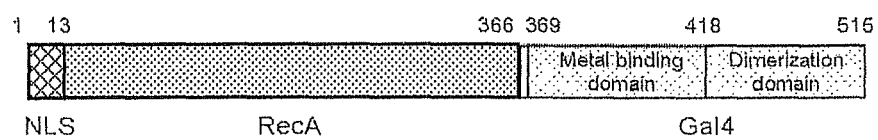
B. NLS-RecA
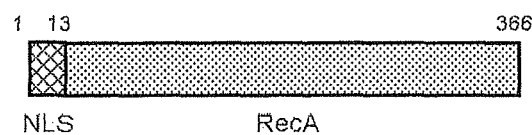
C. NLS-RecA-Gal4△DD
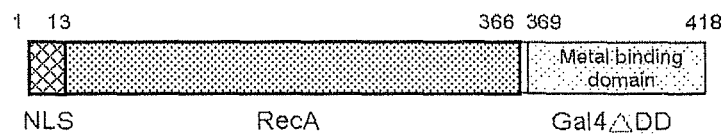

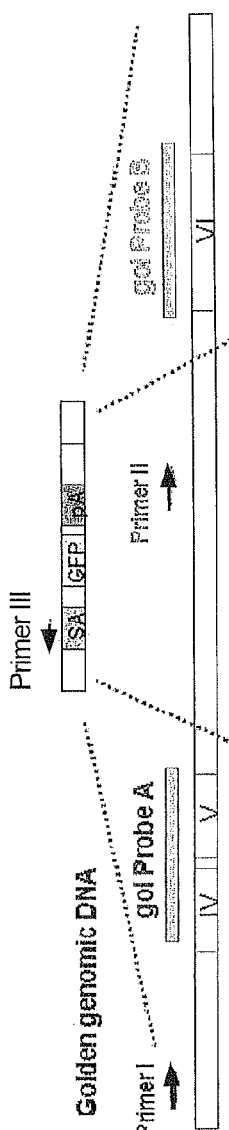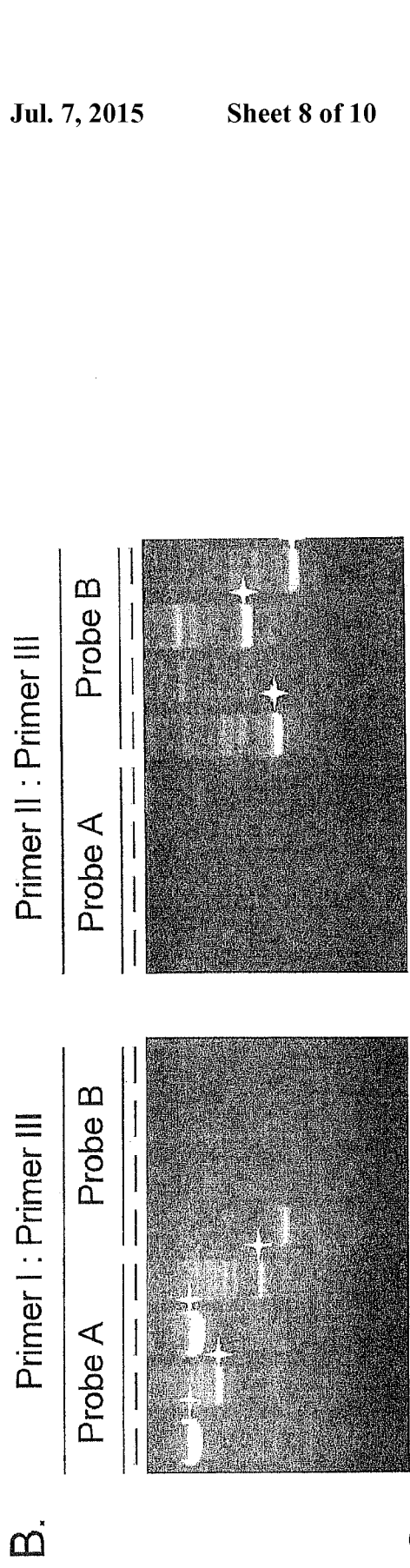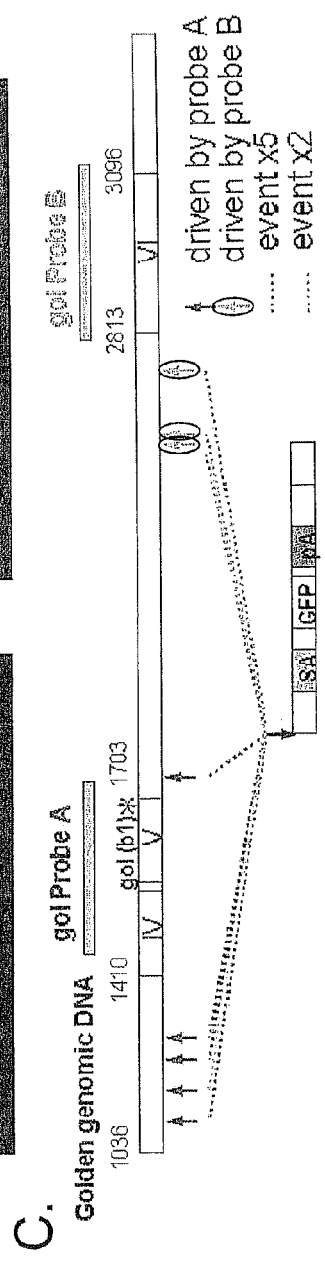
FIG. 8

FIG. 9
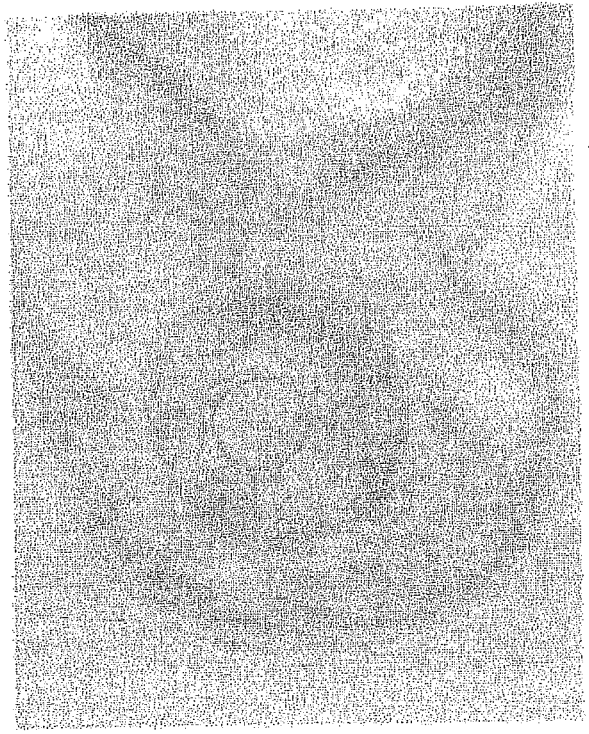
F1 from a test cross
Light Pigment
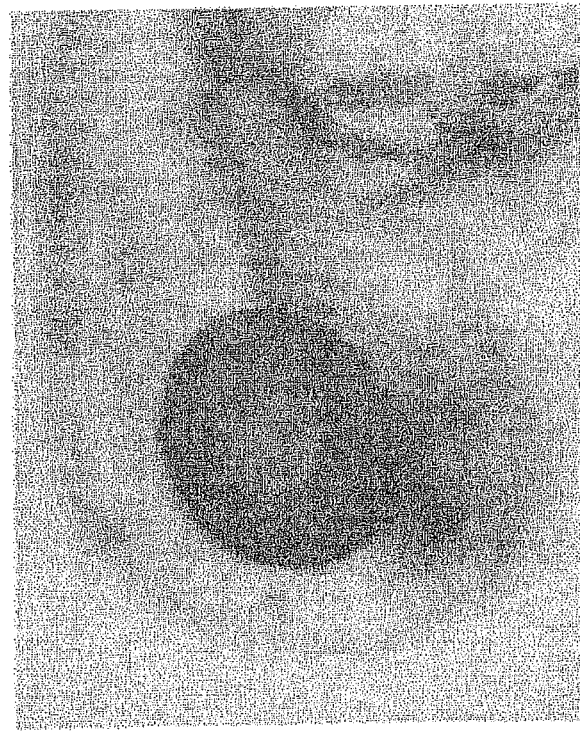
Wild type control
Normal Pigment

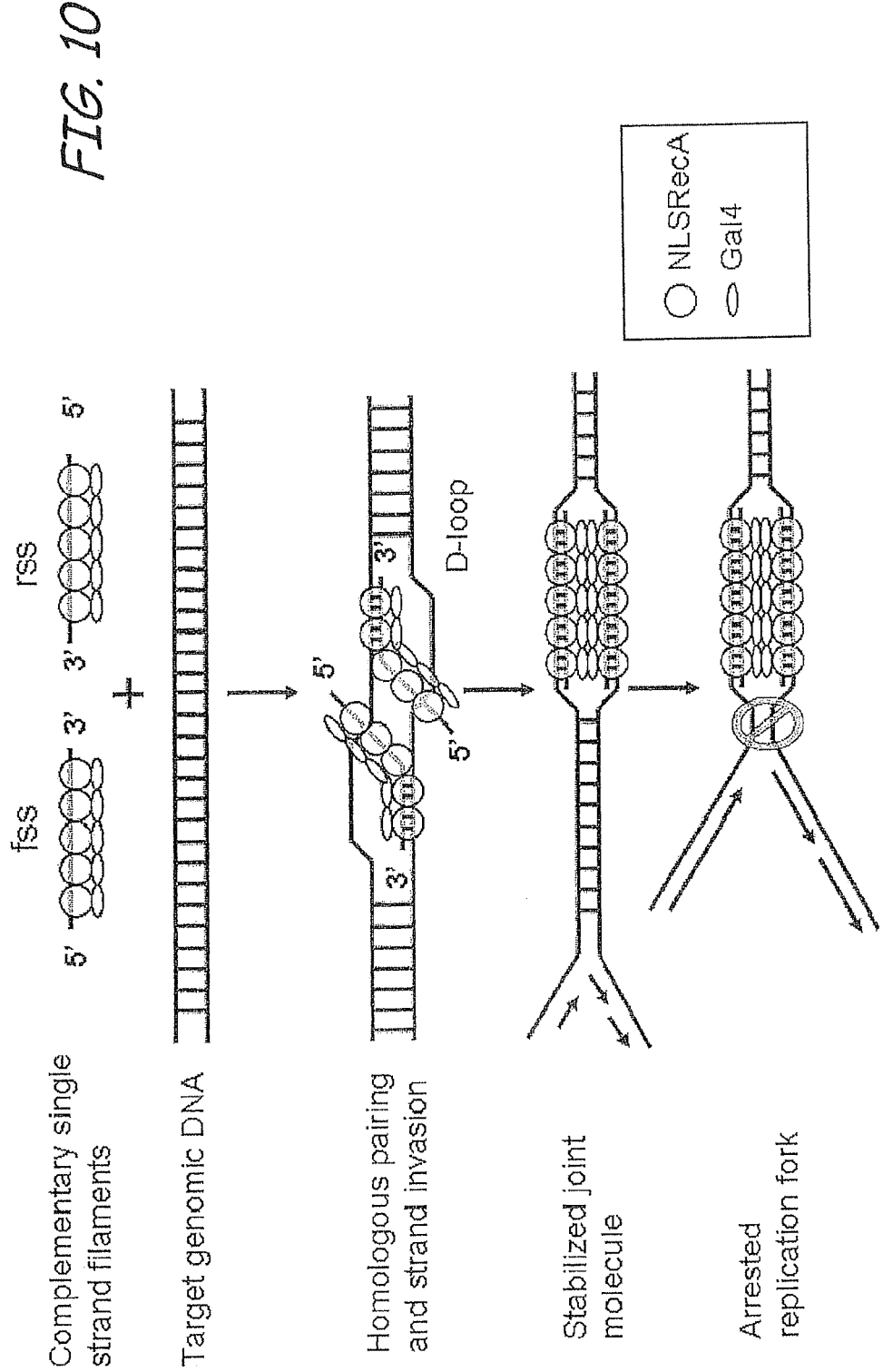

```
                        SEQUENCE LISTING

<160> NUMBER OF SEQ ID NOS: 8

<210> SEQ ID NO 1
<211> LENGTH: 12
<212> TYPE: PRT
<213> ORGANISM: Unknown
<220> FEATURE:
<223> OTHER INFORMATION: mammalian

<400> SEQUENCE: 1

Pro Pro Lys Lys Lys Arg Lys Val Glu Asp Pro Lys
1               5                   10

<210> SEQ ID NO 2
<211> LENGTH: 147
<212> TYPE: PRT
<213> ORGANISM: Unknown
<220> FEATURE:
```

<223> OTHER INFORMATION: mammalian

<400> SEQUENCE: 2

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Glu Glu Ser Ser Asn Lys Gly Gln Arg Gln Leu
    130                 135                 140

Thr Val Ser
145
```

<210> SEQ ID NO 3
<211> LENGTH: 528
<212> TYPE: PRT
<213> ORGANISM: artificial
<220> FEATURE:
<223> OTHER INFORMATION: Synthesized

<400> SEQUENCE: 3

```
Met Pro Pro Lys Lys Arg Lys Val Glu Asp Pro Lys Met Ala Ile
1               5                   10                  15

Asp Glu Asn Lys Gln Lys Ala Leu Ala Ala Ala Leu Gly Gln Ile Glu
            20                  25                  30

Lys Gln Phe Gly Lys Gly Ser Ile Met Arg Leu Gly Glu Asp Arg Ser
        35                  40                  45

Met Asp Val Glu Thr Ile Ser Thr Gly Ser Leu Ser Leu Asp Ile Ala
    50                  55                  60

Leu Gly Ala Gly Gly Leu Pro Met Gly Arg Ile Val Glu Ile Tyr Gly
65                  70                  75                  80

Pro Glu Ser Ser Gly Lys Thr Thr Leu Thr Leu Gln Val Ile Ala Ala
                85                  90                  95

Ala Gln Arg Glu Gly Lys Thr Cys Ala Phe Ile Asp Ala Glu His Ala
            100                 105                 110

Leu Asp Pro Ile Tyr Ala Arg Lys Leu Gly Val Asp Ile Asp Asn Leu
        115                 120                 125

Leu Cys Ser Gln Pro Asp Thr Gly Glu Gln Ala Leu Glu Ile Cys Asp
    130                 135                 140

Ala Leu Ala Arg Ser Gly Ala Val Asp Val Ile Val Val Asp Ser Val
145                 150                 155                 160

Ala Ala Leu Thr Pro Lys Ala Glu Ile Glu Gly Glu Ile Gly Asp Ser
                165                 170                 175

His Met Gly Leu Ala Ala Arg Met Met Ser Gln Ala Met Arg Lys Leu
            180                 185                 190
```

```
Ala Gly Asn Leu Lys Gln Ser Asn Thr Leu Leu Ile Phe Ile Asn Gln
        195                 200                 205

Ile Arg Met Lys Ile Gly Val Met Phe Gly Asn Pro Glu Thr Thr Thr
    210                 215                 220

Gly Gly Asn Ala Leu Lys Phe Tyr Ala Ser Val Arg Leu Asp Ile Arg
225                 230                 235                 240

Arg Ile Gly Ala Val Lys Glu Gly Asn Val Val Gly Ser Glu Thr
            245                 250                 255

Arg Val Lys Val Lys Asn Lys Ile Ala Ala Pro Phe Lys Gln Ala
                260                 265                 270

Glu Phe Gln Ile Leu Tyr Gly Gly Ile Asn Phe Tyr Gly Glu Leu
            275                 280                 285

Val Asp Leu Gly Val Lys Glu Lys Leu Ile Glu Lys Ala Gly Ala Trp
    290                 295                 300

Tyr Ser Tyr Lys Gly Glu Lys Ile Gly Gln Gly Lys Ala Asn Ala Thr
305                 310                 315                 320

Ala Trp Leu Lys Asp Asn Pro Glu Thr Ala Lys Glu Ile Glu Lys Lys
                325                 330                 335

Val Arg Glu Leu Leu Ser Asn Pro Asn Ser Thr Pro Asp Phe Ser
            340                 345                 350

Val Asp Ser Glu Gly Val Ala Glu Thr Asn Glu Asp Phe Ala Ser
            355                 360                 365

Met Lys Leu Leu Ser Ser Ile Glu Gln Ala Cys Asp Ile Cys Arg Leu
    370                 375                 380

Lys Lys Leu Lys Cys Ser Lys Glu Lys Pro Lys Cys Ala Lys Cys Leu
385                 390                 395                 400

Lys Asn Asn Trp Glu Cys Arg Tyr Ser Pro Lys Thr Lys Arg Ser Pro
                405                 410                 415

Leu Thr Arg Ala His Leu Thr Glu Val Glu Ser Arg Leu Glu Arg Leu
            420                 425                 430

Glu Gln Leu Phe Leu Leu Ile Phe Pro Arg Glu Asp Leu Asp Met Ile
        435                 440                 445

Leu Lys Met Asp Ser Leu Gln Asp Ile Lys Ala Leu Leu Thr Gly Leu
    450                 455                 460

Phe Val Gln Asp Asn Val Asn Lys Asp Ala Val Thr Asp Arg Leu Ala
465                 470                 475                 480

Ser Val Glu Thr Asp Met Pro Leu Thr Leu Arg Gln His Arg Ile Ser
                485                 490                 495

Ala Thr Ser Ser Ser Glu Glu Ser Ser Asn Lys Gly Gln Arg Gln Leu
            500                 505                 510

Thr Val Ser Ala Ala Ala Leu Glu His His His His His His
        515                 520                 525

<210> SEQ ID NO 4
<211> LENGTH: 1584
<212> TYPE: DNA
<213> ORGANISM: Artificial
<220> FEATURE:
<223> OTHER INFORMATION: synthesized

<400> SEQUENCE: 4
atgccaccta aaagaagag aaaggtagaa gaccccaaga tggctatcga cgaaaacaaa      60
cagaaagcgt tggcggcagc actgggccag attgagaaac aatttggtaa aggctccatc    120
atgcgcctgg gtgaagaccg ttccatggat gtggaaacca tctctaccgg ttcgctttca    180
```

```
ctggatatcg cgcttggggc aggtggtctg ccgatgggcc gtatcgtcga aatctacgga    240
ccggaatctt ccggtaaaac cacgctgacg ctgcaggtga tcgccgcagc gcagcgtgaa    300
ggtaaaacct gtgcgtttat cgatgctgaa cacgcgctgg acccaatcta cgcacgtaaa    360
ctgggcgtcg atatcgataa cctgctgtgc tcccagccgg acaccggcga gcaggcactg    420
gaaatctgtg acgccctggc gcgttctggc gcagtagacg ttatcgtcgt tgactccgtg    480
gcggcactga cgccgaaagc ggaaatcgaa ggcgaaatcg cgactctca catgggcctt    540
gcggcacgta tgatgagcca ggcgatgcgt aagctggcgg gtaacctgaa gcagtccaac    600
acgctgctga tcttcatcaa ccagatccgt atgaaaattg gtgtgatgtt cggtaacccg    660
gaaaccacta ccggtggtaa cgcgctgaaa ttctacgcct ctgttcgtct cgacatccgt    720
cgtatcggcg cggtgaaaga gggcgaaaac gtggtgggta cgaaacccg cgtgaaagtg    780
gtgaagaaca aaatcgctgc gccgtttaaa caggctgaat ccagatcct ctacggcgaa    840
ggtatcaact tctacggcga actggttgac ctgggcgtaa agagaagct gatcgagaaa    900
gcaggcgcgt ggtacagcta caaaggtgag aagatcggtc agggtaaagc gaatgcgact    960
gcctggctga agataaaccc ggaaaccgcg aaagagatcg agaagaaagt acgtgagttg   1020
ctgctgagca acccgaactc aacgccggat ttctctgtag atgatagcga aggcgtagca   1080
gaaactaacg aagattttgc tagcatgaag ctactgtctt ctatcgaaca agcatgcgat   1140
atttgccgac ttaaaaagct caagtgctcc aaagaaaaac cgaagtgcgc caagtgtctg   1200
aagaacaact gggagtgtcg ctactctccc aaaaccaaaa ggtctccgct gactagggca   1260
catctgacag aagtggaatc aaggctagaa agactggaac agctatttct actgattttt   1320
cctcgagaag accttgacat gatttttgaaa atggattctt tacaggatat aaaagcattg   1380
ttaacaggat tatttgtaca agataatgtg aataaagatg ccgtcacaga tagattggct   1440
tcagtggaga ctgatatgcc tctaacattg agacagcata gaataagtgc gacatcatca   1500
tcggaagaga gtagtaacaa aggtcaaaga cagttgactg tatcggcggc cgcactcgag   1560
caccaccacc accaccacca ccac                                          1584
```

<210> SEQ ID NO 5
<211> LENGTH: 381
<212> TYPE: PRT
<213> ORGANISM: Artificial
<220> FEATURE:
<223> OTHER INFORMATION: synthesized

<400> SEQUENCE: 5

```
Met Pro Pro Lys Lys Arg Lys Val Glu Asp Pro Lys Met Ala Ile
1               5                   10                  15

Asp Glu Asn Lys Gln Lys Ala Leu Ala Ala Leu Gly Gln Ile Glu
                20                  25                  30

Lys Gln Phe Gly Lys Gly Ser Ile Met Arg Leu Gly Glu Asp Arg Ser
            35                  40                  45

Met Asp Val Glu Thr Ile Ser Thr Gly Ser Leu Ser Leu Asp Ile Ala
        50                  55                  60

Leu Gly Ala Gly Gly Leu Pro Met Gly Arg Ile Val Glu Ile Tyr Gly
65                  70                  75                  80

Pro Glu Ser Ser Gly Lys Thr Thr Leu Thr Leu Gln Val Ile Ala Ala
                85                  90                  95

Ala Gln Arg Glu Gly Lys Thr Cys Ala Phe Ile Asp Ala Glu His Ala
            100                 105                 110
```

Leu Asp Pro Ile Tyr Ala Arg Lys Leu Gly Val Asp Ile Asp Asn Leu
    115                 120                 125

Leu Cys Ser Gln Pro Asp Thr Gly Glu Gln Ala Leu Glu Ile Cys Asp
130                 135                 140

Ala Leu Ala Arg Ser Gly Ala Val Asp Val Ile Val Val Asp Ser Val
145                 150                 155                 160

Ala Ala Leu Thr Pro Lys Ala Glu Ile Glu Gly Glu Ile Gly Asp Ser
                165                 170                 175

His Met Gly Leu Ala Ala Arg Met Met Ser Gln Ala Met Arg Lys Leu
            180                 185                 190

Ala Gly Asn Leu Lys Gln Ser Asn Thr Leu Leu Ile Phe Ile Asn Gln
        195                 200                 205

Ile Arg Met Lys Ile Gly Val Met Phe Gly Asn Pro Glu Thr Thr Thr
    210                 215                 220

Gly Gly Asn Ala Leu Lys Phe Tyr Ala Ser Val Arg Leu Asp Ile Arg
225                 230                 235                 240

Arg Ile Gly Ala Val Lys Glu Gly Glu Asn Val Val Gly Ser Glu Thr
                245                 250                 255

Arg Val Lys Val Lys Asn Lys Ile Ala Ala Pro Phe Lys Gln Ala
            260                 265                 270

Glu Phe Gln Ile Leu Tyr Gly Glu Gly Ile Asn Phe Tyr Gly Glu Leu
        275                 280                 285

Val Asp Leu Gly Val Lys Glu Lys Leu Ile Glu Lys Ala Gly Ala Trp
    290                 295                 300

Tyr Ser Tyr Lys Gly Glu Lys Ile Gly Gln Gly Lys Ala Asn Ala Thr
305                 310                 315                 320

Ala Trp Leu Lys Asp Asn Pro Glu Thr Ala Lys Glu Ile Glu Lys Lys
                325                 330                 335

Val Arg Glu Leu Leu Leu Ser Asn Pro Asn Ser Thr Pro Asp Phe Ser
            340                 345                 350

Val Asp Asp Ser Glu Gly Val Ala Glu Thr Asn Glu Asp Phe Ala Ser
        355                 360                 365

Ala Ala Ala Leu Glu His His His His His His
    370                 375                 380

<210> SEQ ID NO 6
<211> LENGTH: 1137
<212> TYPE: DNA
<213> ORGANISM: Artificial
<220> FEATURE:
<223> OTHER INFORMATION: synthesized

<400> SEQUENCE: 6
atgccaccta aaagaagag aaaggtagaa gaccccaaga tggctatcga cgaaaacaaa      60
cagaaagcgt tggcggcagc actgggccag attgagaaac aatttggtaa aggctccatc    120
atgcgcctgg gtgaagaccg ttccatggat gtggaaacca tctctaccgg ttcgctttca    180
ctggatatcg cgcttggggc aggtggtctg ccgatgggcc gtatcgtcga aatctacgga    240
ccggaatctt ccgtaaaaac cacgctgacg ctgcaggtga tcgccgcagc gcagcgtgaa    300
ggtaaaacct gtgcgtttat cgatgctgaa cacgcgctgg acccaatcta cgcacgtaaa    360
ctgggcgtcg atatcgataa cctgctgtgc tcccagccgg acaccggcga gcaggcactg    420
gaaatctgtg acgccctggc gcgttctggc gcagtagacg ttatcgtcgt tgactccgtg    480
gcggcactga cgccgaaagc ggaaatcgaa ggcgaaatcg gcgactctca catgggcctt    540

```
gcggcacgta tgatgagcca ggcgatgcgt aagctggcgg gtaacctgaa gcagtccaac      600
acgctgctga tcttcatcaa ccagatccgt atgaaaattg gtgtgatgtt cggtaacccg      660
gaaaccacta ccggtggtaa cgcgctgaaa ttctacgcct ctgttcgtct cgacatccgt      720
cgtatcggcg cggtgaaaga gggcgaaaac gtggtgggta gcgaaacccg cgtgaaagtg      780
gtgaagaaca aaatcgctgc gccgtttaaa caggctgaat tccagatcct ctacggcgaa      840
ggtatcaact tctacggcga actggttgac ctgggcgtaa aagagaagct gatcgagaaa      900
gcaggcgcgt ggtacagcta caaaggtgag aagatcggtc agggtaaagc gaatgcgact      960
gcctggctga aagataaccc ggaaaccgcg aaagagatcg agaagaaagt acgtgagttg     1020
ctgctgagca acccgaactc aacgccggat ttctctgtag atgatagcga aggcgtagca     1080
gaaactaacg aagattttgc ggccgcactc gagcaccacc accaccacca ccaccac       1137

<210> SEQ ID NO 7
<211> LENGTH: 62
<212> TYPE: DNA
<213> ORGANISM: Artificial
<220> FEATURE:
<223> OTHER INFORMATION: primer

<400> SEQUENCE: 7
catatgccac ctaaaaagaa gagaaaggta gaagacccca agatggctat cgacgaaaac      60
aa                                                                    62

<210> SEQ ID NO 8
<211> LENGTH: 32
<212> TYPE: DNA
<213> ORGANISM: Artificial
<220> FEATURE:
<223> OTHER INFORMATION: primer

<400> SEQUENCE: 8
gatcgcggcc gcaaaatctt cgttagtttc tg                                   32
```

METHODS AND COMPOSITIONS FOR TARGETED GENE MODIFICATION

CROSS REFERENCE TO RELATED APPLICATIONS

This application is a continuation of pending international application PCT/US2010/004236, filed on Aug. 3, 2010 entitled "METHODS AND COMPOSITIONS FOR TARGETED GENE MODIFICATION", which claims priority to U.S. Provisional No. 61/230,784 filed Aug. 3, 2009 entitled "METHODS AND COMPOSITIONS FOR TARGETED GENE MODIFICATION", which are both hereby incorporated by reference herein.

STATEMENT OF GOVERNMENT LICENSE RIGHTS

The U.S. Government may have certain rights in the invention through National Institute of Health funding to JJE for R21 Development of Animal Models and Related Biological Materials for Research, "Use of RecA to promote gene targeting".

TECHNICAL FIELD

The technical field relates to targeted genome modification including, but not limited to, targeted insertion, targeted deletion, targeted gene inactivation and targeted mutagenesis.

BACKGROUND

A major area of interest in biology and medicine is the targeted alteration of genomic nucleotide sequences. Such alterations include insertion, deletion and replacement of endogenous chromosomal nucleic acid sequences.

SUMMARY

Compositions and methods that will provide targeted alteration of genomic sequences are disclosed. Certain fusion proteins that safely and efficiently deliver exogenous sequences to the intended site to achieve the desired effect are described and also exemplified with working examples.

Past attempts have been made by others to alter genomic sequences in cultured cells by taking advantage of the natural phenomenon of homologous recombination. See, for example, Capecchi (1989) *Science* 244:1288-1292; U.S. Pat. Nos. 6,528,313 and 6,528,314. If an exogenous polynucleotide has sufficient homology to the genomic region containing the sequence to be altered, it is possible for part or all of the sequence of the exogenous polynucleotide to replace the genomic sequence by homologous recombination. However, the frequency of homologous recombination under these circumstances is extremely low. Moreover, the frequency of insertion of the exogenous polynucleotide at genomic locations that lack sequence homology exceeds the frequency of homologous recombination by several orders of magnitude.

Thus, previous attempts to replace particular sequences have involved contacting a cell ex vivo with an exogenous polynucleotide (also referred to as donor DNA) comprising sequences bearing homology to a targeted chromosomal region), followed by selection of cells ex vivo in which the donor DNA molecule had undergone homologous recombination into the genome. The success rate of these methods is low, due to poor efficiency of homologous recombination and a high frequency of non-specific insertion of the donor DNA into regions of the genome other than the target site.

Because of these known problems with both the efficiency and specificity of existing methods for targeted recombination, there remains a need for specific, high-efficiency methods and compositions for gene targeting. Besides making gene targeting more readily available and practical, such improved methods and compositions would also reduce side effects resulting from non-targeted insertions. See, e.g., Hacien-Bey-Abina et al. (2003) *Science* 302:415-419.

The RecA protein is the prototype of a family of prokaryotic and eukaryotic proteins that catalyze genetic recombination (i.e., exchange of DNA sequence information between two DNA molecules). RecA and its homologues participate in the repair of double-stranded DNA breaks by catalyzing the synapsis of a single-stranded DNA molecule with homologous sequences in a double-stranded DNA to form a heteroduplex molecule. Branch migration in the heteroduplex can result in the transfer of sequence information from the single-stranded DNA to the double-stranded molecule, as occurs in the processes of recombination and gene conversion.

The remarkable and diverse activities of RecA have led researchers to examine the use of this protein, and its homologues, for stimulating homologous recombination and gene targeting in eukaryotes. In tobacco, expression of bacterial RecA containing a nuclear localization signal (NLS-RecA) increased resistance to mytomycin C-induced DNA-crosslinking and also increased somatic intrachromosomal recombination (recombination between homologous chromosomes) by ten-fold. Reiss et al. (1996) *Proc. Natl. Acad. Sci. USA* 93:3094-3098. In a separate study in tobacco, expression of NLS-RecA was found to stimulate sister chromatid exchange 2.4-fold over wild-type levels. Reiss et al. (2000) *Proc. Natl. Acad. Sci. USA* 97:3358-3363.

In mammalian cells, overexpression of NLS-RecA was reported to stimulate gene targeting via homologous recombination 10-fold. Shcherbakova et al. (2000) *Mutation Res.* 459:65-71. In human cells, overexpression of the human RecA homologue RAD51 was able to stimulate recombination by only 2 to 3-fold over wild type levels. Yanez et al. (1999) *Gene Ther.* 6:1282-1290. Another study showed that direct injection of preformed RecA-coated nucleoprotein filaments into zebrafish embryos could correct a mutant form of the enhanced green fluorescent protein (eGFP), albeit at a low frequency. Cui et al. (2003) *Marine Biotechnol.* 5:174-184. In similar injection experiments in zebrafish embryos, another group showed that Rad52, a member of the Rad51 epistasis group, could promote single-strand annealing and low level oligonucleotide-mediated gene disruption. Takahashi et al. (2005) *Nucleic Acids Res.* 33:e120. Other publications relating to RecA include, e.g., U.S. Pat. No. 7,229,767. A recent disclosure described the use of molecular tethers for targeted insertion of transposon vectors, wherein the tether comprises a DNA-binding domain that binds a target site in the vector, see U.S. Patent Publication No. 2007/0031380. Other publications relating to transposons include, for example, U.S. Pat. Nos. 6,498,458, 7,160,682, and 7,527,966.

Conventional tools used to perform reverse genetics and create targeted modification of specific genes are limited to a few species and require sophisticated and labor intensive technologies that typically involve cloning or engineering of embryonic stem cells. To address these limitations, innovative technologies were developed that can be used to modify specific chromosomal regions by direct injection of protein-nucleic acid complexes into fertilized zygotes. A modified version of the bacterial RecA protein is described that is able to promote homologous or non-homologous recombination and insertion of exogenous DNA into specific genomic locations for gene modification. This modified version of RecA functions at frequencies several orders of magnitude greater than previous reports. This is a highly active form of RecA that functions in vertebrates and is expected to function in animals and plants generally. The modification and use of RecA is an unexpected and surprising result that was not expected to function as it does, i.e., to promote homologous recombination.

BRIEF DESCRIPTION OF THE DRAWINGS

FIG. 1 shows the amino acid sequence of a NLS/RecA/Gal4 fusion protein (SEQ ID NO:3).

FIG. 2 shows the nucleotide sequence encoding a NLS/RecA/Gal4 fusion protein (SEQ ID NO:4).

FIG. 3 shows the amino acid sequence of a NLS/RecA fusion protein (SEQ ID NO:5).

FIG. 4 shows the nucleotide sequence encoding a NLS/RecA fusion protein (SEQ ID NO:6).

FIG. 5 is an illustration of three types of RecA fusion proteins.

FIG. 8 depicts site-specific insertion of exogenous DNA. As depicted, cssDNA-NLS-RecA-Gal4 filaments directed site-specific insertion of GFP DNA. Panel A: Two regions of the gol gene were amplified, denatured, and coated with NLS-RecA-Gal4 protein to make ssDNA-NLS-RecA-Gal4 filaments. Filaments were injected with foreign DNA containing a splice acceptor (SA) followed by the green fluorescent protein (GFP) in three reading frames and a poly adenylation signal (pA). Panel B: PCR amplification of junction fragments between the foreign DNA and the endogenous gol locus were obtained from DNA isolated from individual embryos. Bands marked with a star were sequence-verified as junction fragments. Panel C: Junction fragment map of insertions into the gol locus showing insertion of exogenous DNA near ends of the regions complementary to the junction fragments.

FIG. 9 depicts targeted mutation for creation of a transgenic animal. The gol locus in the zebrafish germline was targeted and modified. A testcross between a gol targeted founder and gol$^{b1}$ homozygotes produced offspring that fail to complement the b1 allele (right) and its sibling with normal pigment (left).

FIG. 10 depicts a model for gene targeting by cssDNA-NLSRecAGal4. Both forward and reverse single strand (fss and rss)-NLSRecAGal4 filaments are co-injected into zebrafish embryos. The RecA homology search activity guides the filaments to the targeted region. The cssDNA-NLSRecAGal4 filaments undergoes homologous pairing and strand invasion, which causes the formation of D-loops on the target chromosome. The structure is stabilized by the Gal4 dimerization domains between the complementary filaments. This compact DNA joint molecule is theorized to block replication fork progression, leading to a double strand break (DSB).

DETAILED DESCRIPTION

Nucleic acids coated with certain fusion proteins were shown to be targeted to specific target sites. Double stranded exogenous nucleic acid sequences were incorporated into the host cell at the target sites, and expressed by the cells. Animals thus transfected continuously expressed the gene and passed the genetic alterations to offspring. This method is very simple and powerful compared to conventional technologies, which are limited to a few species and require sophisticated and labor intensive techniques.

It was discovered that the pairing activity of RecA-DNA filaments could be utilized to target biochemical activities to specific chromosomal sites. Various filaments with chimeric RecA proteins were tested with various genes. The vertebrate animal model was the zebrafish. In this model, site-specific disruption of a gene is demonstrated by inducing loss of heterozygosity (LOH) at the golden locus in zebrafish after injection at the 1-cell stage. LOH is visible by a mosaic pigmentation and was verified by direct DNA analysis. The results reported herein demonstrate that DNA filaments, of various sizes, coated with the fusion proteins are able to cause site-directed mutations and targeted chromosomal deletions in zebrafish that are transmitted to subsequent generations. Further, co-injection of an exogenous nucleic acids with the fusion protein promotes the insertion of the exogenous nucleic acids into targeted genomic locations, likely through the non-homologous end joining pathway.

Without being limited to a particular theory, a model is presented whereby the Gal4 domain of NLSRecAGal4 promotes the dimerization of complementary single strand (css) filaments after the filaments find their target. The model provides for a complex that creates a steric block to replication, resulting in a stalled replication fork and either repair of the locus or chromosomal breakage.

Data herein provides evidence that proteinaceous fusion molecules can be specifically targeted to a target site in a host chromosome and create a break. This break can be exploited to create mutants, discover gene function, insert exogenous genes, and other purposes. Examples 1 and 2 details such a fusion molecule, specifically, a NLS domain-RecA domain-Gal4 domain molecule or an NLS domain-RecA domain, and DNA constructs for making them. These fusion molecules retain nucleoprotein filament-forming function (Example 3). In Example 4, the zebrafish model was used to demonstrate disruption of specific gene sites. Double-stranded DNA probes complementary to various sites in the gol locus were denatured into single strands and formed into filaments with a NLS/RecA/Gal4 proteinaceous fusion molecule. Both 1300 base pair (bp) and 60 bp probes directed to distinct sites in gol were successfully used. The probes were not integrated into the host cell DNA.

Figure 7:
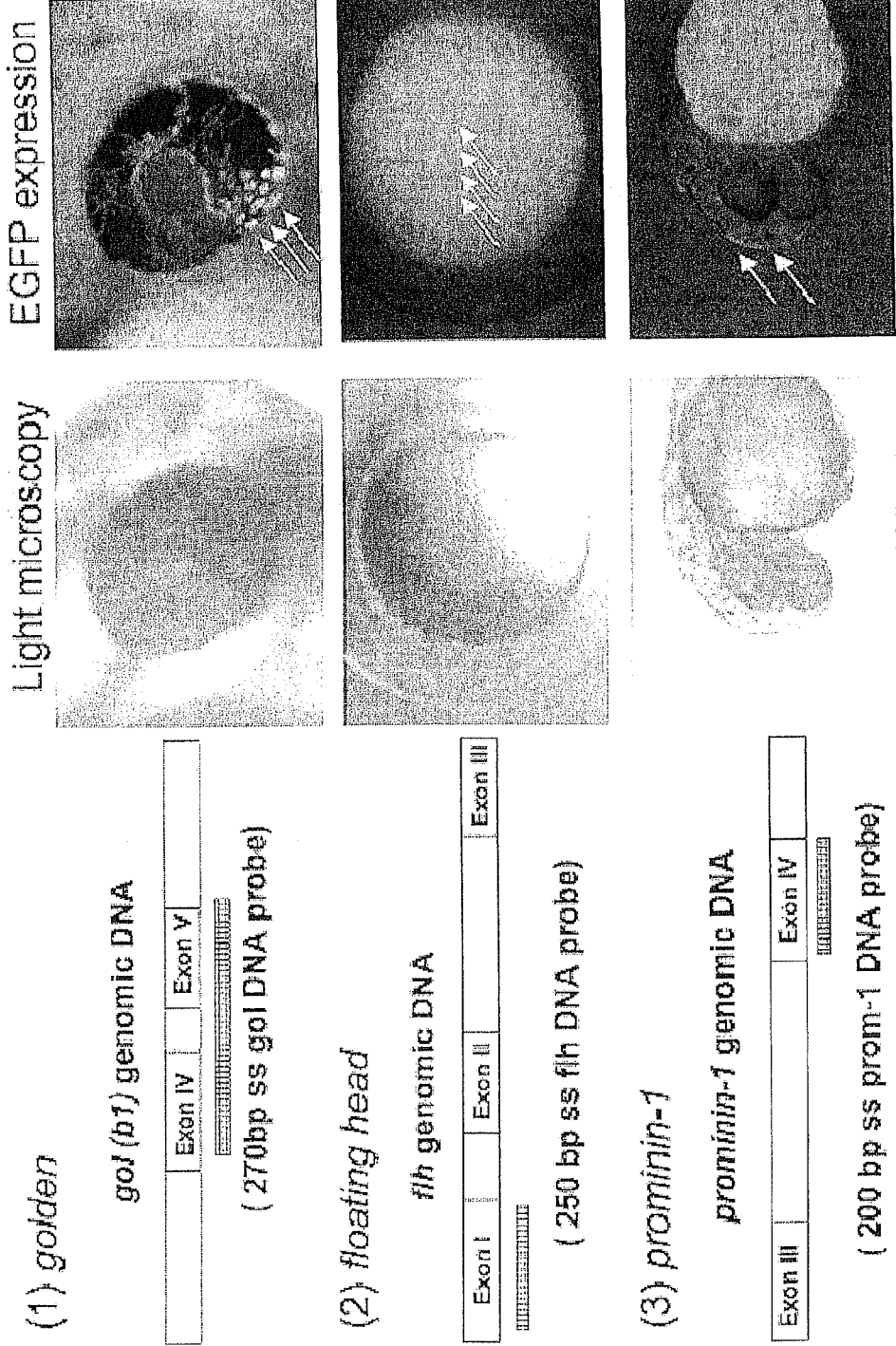
FIG. 7 depicts results that show, for three different genes, that gene expression is a result of site specific integration. As depicted, expression of an EGFP reporter gene is consistent with site specific integration into the gol, flh, and prominin-1 loci. Single-stranded NLS-RecA-Gal4 filaments complementary to the (1) gol, (2) flh, and (3) prominin-1 loci were co-injected with the EGFP reporter gene cassette. EGFP expression consistent with targeting gene expression was observed in 5-19% of the injected embryos. For the gol gene, expression was observed in the eye, for the flh gene in the notochord, and for the prominin-1 gene in the dorsal diencephalon.

Further data showed that exogenous DNA could then be integrated at specific sites and that the method was generally applicable to genes and not limited to gol. In Example 5, targeted insertion events were demonstrated by the tissue-specific expression of enhanced green fluorescent protein (EGFP) gene after co-injection with ssDNA-NLS-RecA-Gal4 filaments complementary to the gol, prominin1, and floating head (flh) loci (FIG. 7). The expression was observed in the absence of an exogenous promoter, i.e., the insertion site was chosen so as to take advantage of native promoters and cellular machinery. Analysis of the insertion sites showed them to be in the targeted gene, and within about 500 bp of the probe's target site. Finally, transfection of the germline and progeny that expressed the exogenous genes was demonstrated (Example 6). Biological mechanisms are detailed below.

Other experiments were performed with a gol-mcherry-gol replacement construct, which was able to target the gol genomic locus. The gol gene exons are designated E1 through E9. The targeting construct contained the mcherry (M) gene. Injection of this replacement construct with NLSRecAGal4 resulted in red fluorescent sectors in the eye. Furthermore, a junction fragment was recovered after nested PCR amplification indicative of homologous recombination between the gol replacement vector and the endogenous gol gene.

Embodiments of the invention thus include a fusion molecule with a recombinase domain and a DNA-binding domain. The fusion molecule may include a nuclear localization signal or otherwise be transported into the cell and nucleus. Systems may include probes and exogenous DNA for insertion into a host cell. These features are detailed herein.

Practice of the present disclosure employs, unless otherwise indicated, standard methods and conventional techniques in the fields of cell biology, developmental biology, reproductive biology, molecular biology, biochemistry, cell culture, recombinant DNA and related fields as are within the skill of the art. Such techniques are described in the literature and thereby available to those of skill in the art. See, for example, Alberts, B. et al., "Molecular Biology of the Cell," 5$^{th}$ edition, Garland Science, New York, N.Y., 2008; Voet, D. et al. "Fundamentals of Biochemistry: Life at the Molecular Level," 3$^{rd}$ edition, John Wiley & Sons, Hoboken, N.J., 2008; Sambrook, J. et al., "Molecular Cloning: A Laboratory Manual," 3$^{rd}$ edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," 4$^{th}$ edition, John Wiley & Sons, Somerset, N.J., 2000; and the series "Methods in Enzymology," Academic Press, San Diego, Calif.

Fusion Molecules

The methods and compositions for targeted genome modification disclosed herein involve, in certain embodiments, the use of fusion molecules. For the purposes of the present disclosure, a fusion molecule is a non-naturally-occurring molecule that contains at least two domains joined to each other within a single molecule, such that the two domains are not found together in a naturally-occurring molecule. The domains can be naturally-occurring or synthetic. The domains can be the same chemical type of molecule, or can be different chemical types of molecules. The term proteinaceous fusion molecule refers to a fusion molecule having at least two polypeptide domains. Since it has polypeptide domains it is "proteinaceous", and it may further comprise non-protein features, e.g., polymeric linkers. The term polypeptide domain refers to: a set of peptides joined together that collectively and independently accomplish a biological function. Examples of domains that satisfy this definition are zinc fingers, the calcium-binding EF hand domain of calmodulin, peptide sequences that exhibit specific binding to a predetermined target, NLS, DNA-binding sequences, and portions of proteins that perform the function of the wildtype protein (e.g., a derivative of RecA). Polypeptide domains can thus, for example, be mixed-and-matched by genetic engineering between one protein and another to make chimeric proteins.

In certain embodiments, a proteinaceous fusion molecule includes at least two domains selected from the group consisting of a first domain that is a DNA-binding domain; e.g., a DNA-binding protein or a functional fragment of a DNA-binding protein, a second domain that comprises a polypeptide sequence having recombinase activity, and a third domain that comprises a nuclear localization signal. These domains may be in any order, e.g., NLS-recombinase-DNA binding or DNA-binding-NLS-recombinase. The domains may be separated by linkers that are peptidic or made of other materials.

In certain embodiments, each of the fusion molecule domains corresponds to a distinct polypeptide sequence; for example a polypeptide DNA-binding domain such as Gal4 and polypeptide sequences from RecA having recombinase activity. However, it is also possible for the fusion molecules to possess non-polypeptide domains. For example, the DNA-binding domain can comprise a polymer, a peptide spacer, a triplex-forming nucleic acid, a polyamide, a minor groove binder, an intercalating agent, an antibiotic and/or a nucleic acid.

Fusion molecules, including fusion proteins and nucleic acids encoding them, are constructed by methods of cloning and biochemical conjugation that are well-known to those of skill in the art. Fusion proteins (and nucleic acids encoding them) may be designed such that the translational reading frame is preserved among the components of the fusion.

Fusions between polypeptide sequences possessing recombinase activity, on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. In other embodiments, a chemical linker is used to connect synthetically or recombinantly produced domains. Such flexible linkers are known to persons of skill in the art. For example, poly(ethylene glycol) linkers are available from Shearwater Polymers, Inc. (Huntsville, Ala.). These linkers optionally have amide linkages, sulfhydryl linkages, or heterofunctional linkages.

Methods and compositions for making fusions between a minor groove binder and a polypeptide have been described. Mapp et al. (2000) *Proc. Natl. Acad. Sci. USA* 97:3930-3935.

With respect to fusion polypeptides, the term "operatively linked" refers to the fact that each of the components performs the same function in linkage to the other component as it would if it were not so linked.

A functional fragment of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, either genetic or biochemical. See, for example, Fields et al. (1989) *Nature* 340:245-246; U.S. Pat. No. 5,585,245 and PCT WO 98/44350. Accordingly, embodiments include fusion molecules with a functional fragment of one or more of a recombinase, RecA, NLS, Gal4, and polypeptide DNA-binding domains.

In certain embodiments, a fusion between a polypeptide DNA-binding domain and polypeptide sequences possessing recombinase activity is encoded by a fusion nucleic acid. In such cases, the nucleic acid can be cloned into intermediate vectors for transformation into prokaryotic or eukaryotic cells for replication and/or expression. Intermediate vectors for storage or manipulation of the fusion nucleic acid or production of fusion protein can be prokaryotic vectors, (e.g., plasmids), shuttle vectors, insect vectors, or viral vectors for example. A fusion nucleic acid can also cloned into an expression vector, for administration to a bacterial cell, fungal cell, protozoal cell, plant cell, or animal cell, e.g., a mammalian cell or a human cell. Vectors for replication, expression, storage and/or manipulation of cloned nucleic acid sequences are well-known in the art. See, e.g., Sambrook, supra, and Ausubel, supra.

Thus, expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

Linker domains can be included between polypeptide domains, e.g., between a DNA-binding domain and polypeptide sequences having recombinase activity. Such linkers can be polypeptide sequences, such as poly-glycine sequences of from 1 to about 200 amino acids. Linker domains can comprise flexible amino acid subsequences which are synthesized as part of a recombinant fusion protein. For example, a linker domain can comprise amino acid sequence with a plurality of amino acids, e.g, from 1 to 20; artisans will immediately appreciate that all the ranges and values within the explicitly stated ranges are contemplated, e.g., 2, or 10, or from 3 to 11. Alternatively, flexible linkers can be rationally designed using computer programs capable of modeling both DNA-binding sites and the peptides themselves (Desjarlais & Berg (1993) *Proc. Natl. Acad. Sci. USA* 90:2256-2260; Desjarlais et al. (1994) *Proc. Natl. Acad. Sci. USA* 91:11099-11103) or by phage display methods. Methods for obtaining sequences that mediate non-covalent linkage between polypeptide domains have also been described. Wang et al. (1999) *Proc. Natl. Acad Sci. USA* 96:9568-9573.

Nuclear Localization Signals

Fusion molecules, as disclosed herein, also optionally comprise nuclear localization signals ("NLS"). As used herein, the term "nuclear localization signal" means an amino acid sequence known to, in vivo, direct a protein disposed in the cytoplasm of a cell across the nuclear membrane and into the nucleus of the cell. A nuclear localization signal can also target the exterior surface of a cell. Thus, a single nuclear localization signal can direct the entity with which it is associated to the exterior of a cell and to the nucleus of a cell. Such sequences can be of any size and composition, for example between 4 and 400 amino acids; artisans will immediately appreciate that all the ranges and values within the explicitly stated ranges are contemplated, for example more than 25, 25, 15, 12, 10, 8, 7, 6, 5 or 4 amino acids.

NLS are peptidic groups that signal importation of a protein into the nucleus. Examples of NLS are SV40 large T-antigen, nucleoplasmin, HIV-1 Rev, and hnRNPA1 (M9), see Escriou et al., NLS bioconjugates for targeting therapeutic genes to the nucleus, Advanced Drug Delivery Reviews, 55 (2003) 295-306. Several peptides have been derived from the SV40 T antigen. These include a short NLS or long NLS's. Other NLS peptides have been derived from M9 protein, nucleoplasmin, and c-myc.

DNA-Binding Domains

In certain embodiments, the compositions and methods disclosed herein involve fusions between a DNA-binding domain and a domain having recombinase activity. Any DNA-binding domain known in the art can be used as part of a fusion molecule. A DNA-binding domain can comprise any molecular entity capable of sequence-specific binding to chromosomal DNA. Binding can be mediated by electrostatic interactions, hydrophobic interactions, or any other type of chemical interaction. Examples of moieties which can comprise part of a DNA-binding domain include, but are not limited to, minor groove binders, major groove binders, antibiotics, intercalating agents, peptides, polypeptides, peptide nucleic acids, polyamides, oligonucleotides, and polynucleotides. An example of a DNA-binding nucleic acid is a triplex-forming oligonucleotide.

Embodiments include fusion molecules with a DNA-binding domain that are directed to techniques and treatments for gene conversion, homology-independent gene targeting, homologous recombination, targeted mutagenesis, genetic diseases, transgenic animals, expression vectors, and administration into plants.

Minor groove binders include substances which, by virtue of their steric and/or electrostatic properties, interact preferentially with the minor groove of double-stranded nucleic acids. Certain minor groove binders exhibit a preference for particular sequence compositions. For instance, netropsin, distamycin and CC-1065 are examples of minor groove binders which bind specifically to AT-rich sequences, particularly runs of A or T. WO 96/32496.

Polyamide DNA-binding domains are described, for example, in U.S. Pat. No. 6,555,692. Peptide nucleic acids are described, for example, in U.S. Pat. Nos. 5,539,082; 5,773, 571; 6,395,474; 6,451,968 and 7,378,485. See also Nielsen et al. (1991) *Science* 254:1497-1500.

Many antibiotics are known to exert their effects by binding to DNA. Binding of antibiotics to DNA is often sequence-specific or exhibits sequence preferences. Actinomycin, for instance, is a relatively GC-specific DNA binding agent.

Polypeptide DNA binding domains are found, for example, in proteins involved in DNA replication, DNA repair, recombination and transcription. Defined regions within the polypeptide sequence of various transcription factors have been shown to be responsible for sequence-specific binding to DNA. These regions include, but are not limited to, motifs known as leucine zippers, helix-loop-helix (HLH) domains, helix-turn-helix domains, zinc fingers, beta-sheet motifs, steroid receptor motifs, bZIP domains homeodomains, AT-hooks and others. The amino acid sequences of these motifs are known and, in some cases, amino acids that are critical for sequence specificity have been identified. See, for example, Pabo et al. (1992) *Ann. Rev. Biochem.* 61:1053-1095 and references cited therein. Exemplary well-characterized DNA-binding domains include those for LexA, Gal4 and zif268. Webster et al., (1988) Cell 52: 169-178.

Peptide sequences involved in specific DNA recognition, such as those found in transcription factors, can be obtained through recombinant DNA cloning and expression techniques or by chemical synthesis, and can be attached to other components of a fusion molecule by methods known in the art.

In addition to naturally-occurring DNA-binding domains such as those described above, non-naturally-occurring, engineered DNA-binding domain can also be used. In this regard, the zinc finger DNA-binding domain is useful, inasmuch as it is possible to engineer zinc finger proteins to bind to any DNA sequence of choice. A zinc finger binding domain comprises one or more zinc finger structures. Miller et al. (1985) *EMBO J* 4:1609-1614; Rhodes (1993) *Scientific American* February: 56-65; U.S. Pat. No. 6,453,242. Typically, a single zinc finger is about 30 amino acids in length and contains four zinc-coordinating amino acid residues. Structural studies have demonstrated that the canonical ($C_2H_2$) zinc finger motif contains two beta sheets (held in a beta turn which generally contains two zinc-coordinating cysteine residues) packed against an alpha helix (generally containing two zinc coordinating histidine residues).

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). Non-canonical zinc fingers can also include those in which an amino acid other than cysteine or histidine is substituted for one of these zinc-coordinating residues. See e.g., WO 02/057293 (Jul. 25, 2002) and US 2003/0108880 (Jun. 12, 2003).

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. Consequently, zinc finger binding domain can be engineered to have a novel binding specificity, compared to a naturally-occurring zinc finger protein. Engineering methods include, but are not limited to, rational design and various types of empirical selection methods. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Patent Application Publication Nos. 2002/0165356; 2004/0197892; 2007/0154989; 2007/0213269; and International Patent Application Publication Nos. WO 98/53059 and WO 2003/016496.

Exemplary selection methods, including phage display, interaction trap, hybrid selection and two-hybrid systems, are disclosed in U.S. Pat. Nos. 5,789,538; 5,925,523; 6,007,988; 6,013,453; 6,140,466; 6,200,759; 6,242,568; 6,410,248; 6,733,970; 6,790,941; 7,029,847 and 7,297,491; as well as U.S. Patent Application Publication Nos. 2007/0009948 and 2007/0009962; WO 98/37186; WO 01/60970 and GB 2,338,237.

Additional methods for design of sequence-specific zinc finger DNA-binding domains have been described by Maeder et al. (2008) *Mol. Cell* 31:294-301.

Enhancement of binding specificity for zinc finger binding domains has been described, for example, in U.S. Pat. No. 6,794,136 (Sep. 21, 2004). Additional aspects of zinc finger engineering, with respect to inter-finger linker sequences, are disclosed in U.S. Pat. No. 6,479,626 and U.S. Patent Application Publication No. 2003/0119023. See also Moore et al. (2001a) *Proc. Natl. Acad. Sci. USA* 98:1432-1436; Moore et al. (2001b) *Proc. Natl. Acad. Sci. USA* 98:1437-1441 and WO 01/53480.

Zinc finger DNA-binding domains, engineered to bind a DNA sequence of choice, are commercially available (CompoZr™, Sigma-Aldrich, St. Louis, Mo.). Fusions between a recombinase domain and a zinc finger DNA-binding domain have been described by Akopian et al. (2003) *Proc. Natl. Acad Sci. USA* 100:8688-8691.

All of the references cited in this section, entitled "DNA Binding Domains," are hereby incorporated by reference herein in their entireties for the purposes of disclosing art-recognized DNA-binding domains and methods for the design, selection and engineering of zinc finger DNA-binding domains.

In general, Gal4 is used as an example of a DNA-binding domain. Similarly, RecA is used as an example of a recombinase, with a fusion protein of the two being an exemplary fusion protein. One of the utilities of the NLS-RecA-Gal4 fusion protein is its ability like RecA to coat single-stranded DNA and find homologous regions in a genome to the RecA filament. By doing this, the RecA part of NLS-RecA-Gal4 brings the activity associated with the Gal4 DNA binding domain into the targeted chromosomal region. The Gal4 DNA binding motif contains both a metal coordination center and a dimerization motif. Both of these activities are like required for NLS-RecA-Gal4 fusion protein coated DNA to promote chromosomal breaks by potentially creating stalled replication forks. Other mechanisms are envisioned as well.

Using this ability of RecA fusion proteins, different activities can be carried to distinct chromosomal locations by substituting the Gal4 domain with other proteins or motifs. For example, a nuclease could be substituted for Gal4. In this case the RecA-coated filament would bring the nuclease, via its attachment to RecA, to a specific chromosomal site. Several recent reports have highlighted the use of zinc finger nucleases to modify specific chromosomal regions by their ability to induce double strand breaks (Bibikova et al., 2002; Porteus and Baltimore, 2003; Urnov et al., 2005; Wright et al., 2005). The specificity of this technique relies on the observation that the restriction endonuclease, FokI, is only active as a dimer. Consequently, this system requires that the FokI-zinc fingers bind two distinct sites. The FokI-induced double strand breaks can be repaired from an exogenously supplied plasmid DNA that contains a region of homology. If the exogenously supplied DNA contains a change relative to the chromosomal target, this change can be incorporated into the repaired chromosome. This technique appears to function well in a variety of systems and has been used efficiently to modify chromosomes in *Drosophila* (Bibikova et al., 2002), tobacco (Wright et al., 2005), and human cells (Porteus and Baltimore, 2003; Urnov et al., 2005). Because the engineering of zinc fingers can require significant selection, the widespread use of this technique may be limited. The homology searching function of RecA can substitute for the zinc fingers in this system. Either chimeric RecA-FokI proteins or RecA coated filaments that bind FokI could induce specific double strand breaks at specific chromosomal sites. Other nucleases such as I-sce-I and EcoRI could also be used.

Other activities that could replace the Gal4 domain include different DNA binding motifs such as zinc fingers and helix-turn-helix proteins. This would further promote distinct activities and the ability to site specifically modify a chromosome.

Techniques include introduction of a fusion protein with a DNA-binding domain that is not specifically bound to a DNA. Trivial binding events are not specific binding events. Specific binding, as that term is commonly used in the biological arts, generally refers to a molecule that binds to a target with a relatively high affinity compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and specifically binding protein-receptor interactions; while such molecules may bind tissues besides their targets from time to time, such binding is said to lack specificity and is not specific binding. Thus a DNA-binding domain will not exhibit specific binding to a nucleic acid unless a sequence specifically recognized by the domain is present.

Recombinases

The term recombinase refers to a genetic recombination enzyme that enzymatically catalyzes, in a cell, the joining of relatively short pieces of DNA between two relatively longer DNA strands. Recombinases include Cre recombinase, Hin recombinase, RecA, RAD51, Tre, and FLP. Cre recombinase is a Type I topoisomerase from P1 bacteriophage that catalyzes site-specific recombination of DNA between loxP sites. Hin recombinase is a 21 kD protein composed of 198 amino acids that is found in the bacteria *Salmonella*. Hin belongs to the serine recombinase family of DNA invertases in which it relies on the active site serine to initiate DNA cleavage and recombination. RAD51 is a human gene. The protein encoded by this gene is a member of the RAD51 protein family which assist in repair of DNA double strand breaks. RAD51 family members are homologous to the bacterial RecA and yeast Rad51. Tre recombinase is an experimental enzyme that in lab tests has successfully removed DNA inserted by HIV from infected cells. The enzyme was derived from Cre recombinase through selective mutation for the purposes of identifying HIV markers, which are not bounded by loxP sites and therefore disallow attempts at Cre-Lox recombination. FLP refers to Flippase recombination enzyme (FLP or Flp) derived from the 2µ plasmid of the baker's yeast *Saccharomyces cerevisiae*.

RecA is known for its recombinase activity to catalyze strand exchange during the repair of double-strand breaks by homologous recombination (McGrew and Knight, 2003) Radding, et al., 1981; Seitz et al., 1998). RecA has also been shown to catalyze proteolysis, e.g., of the LexA and λ repressor proteins, and to possess DNA-dependent ATPase activity. After a double-strand break occurs from ionizing radiation or some other insult, exonucleases chew back the DNA ends 5' to 3', thereby exposing one strand of the DNA (Cox, 1999; McGrew and Knight, 2003). The single-stranded DNA becomes stabilized by single-strand binding protein (SSB). After binding of SSB, RecA binds the single-stranded (ss) DNA and forms a helical nucleoprotein filament (referred to as a filament or a presynaptic filament). During DNA repair, the homology-searching functions of RecA direct the filament to homologous DNA and catalyze homologous base pairing and strand exchange. This results in the formation of DNA heteroduplex. After strand invasion, DNA polymerase elongates the ssDNA based on the homologous DNA template to repair the DNA break, and crossover structures or Holliday junctions are formed. RecA also shows a motor function that participates in the migration of the crossover structures (Campbell and Davis, 1999).

Recombinase activity comprises a number of different functions. For example, polypeptide sequences having recombinase activity are able to bind in a non-sequence-specific fashion to single-stranded DNA to form a nucleoprotein filament. Such recombinase-bound nucleoprotein filaments are able to interact in a non-sequence-specific manner with a double-stranded DNA molecule, search for sequences in the double-stranded molecule that are homologous to sequences in the filament, and, when such sequences are found, displace one of the strands of the double-stranded molecule to allow base-pairing between sequences in the filament and complementary sequences in one of the strands of the double stranded molecule. Such steps are collectively denoted "synapsis."

RecA and RecA-like proteins (called Rad51 in non-bacterial species) have been examined for stimulating gene targeting and homologous recombination in a variety of eukaryotic systems. In tobacco cells, expression of bacterial RecA containing a nuclear localization signal (NLS) increases the repair of mitomycin C-induced DNA damage by homologous recombination and somatic intrachromosomal recombination (recombination between homologous chromosomes) from three to ten fold (Reiss et al., 1996). Expression of NLSRecA in tobacco can also stimulate sister chromatid exchange 2.4-fold over wild-type levels (Reiss et al., 2000). In somatic mammalian cells, overexpression of NLSRecA stimulates gene targeting by homologous recombination 10-fold (Shcherbakova et al., 2000). However, in human cells, overexpression of a human homologue of RecA, hRAD51, only stimulates recombination 2 to 3-fold over wild type levels under the antibiotic selection (Yanez and Porter, 1999). In zebrafish, a mutant form of the enhanced green fluorescent protein (EGFP) was corrected at low frequency by injecting ssDNA-RecA filaments directly (Cui et al., 2003). Rad52, a member of the Rad51 epistasis group, also promotes single-strand annealing and low level gene disruption in zebrafish using mutated oligonucleotides (Takahashi and Dawid, 2005). Taken together, these studies indicate that ectopic expression of RecA or Rad51 results in a modest stimulation of homologous recombination but does not increase levels enough to be useful for gene targeting.

Thus recombinase activities include, but are not limited to, single-stranded DNA-binding, synapsis, homology searching, duplex invasion by single-stranded DNA, heteroduplex formation, ATP hydrolysis and proteolysis. The prototypical recombinase is the RecA protein from *E. coli*. See, for example, U.S. Pat. No. 4,888,274. Prokaryotic RecA-like proteins have also been described in *Salmonella, Bacillus* and *Proteus* species. A thermostable RecA protein, from *Thermus aquaticus*, has been described in U.S. Pat. No. 5,510,473. A bacteriophage T4 homologue of RecA, the UvsX protein, has been described. RecA mutants, having altered recombinase activities, have been described, for example, in U.S. Pat. Nos. 6,774,213; 7,176,007 and 7,294,494. Plant RecA homologues are described in, for example, U.S. Pat. Nos. 5,674, 992; 6,388,169 and 6,809,183. RecA fragments containing recombinase activity have been described, for example, in U.S. Pat. No. 5,731,411. Mutant RecA proteins having enhanced recombinase activity such as, for example, RecA803 have been described. See, for example, Madiraju et al. (1988) Proc. Natl. Acad. Sci. USA 85:6592-6596.

A eukaryotic homologue of RecA, also possessing recombinase activity, is the Rad51 protein, first identified in the yeast Saccharomyces cerevisiae. See Bishop et al., (1992) Cell 69: 439-56 and Shinohara et al, (1992) Cell: 457-70 Aboussekhra, et al., (1992) Mol. Cell. Biol. 72, 3224-3234. Basile et al., (1992) Mol. Cell. Biol. 12, 3235-3246. Plant Rad51 sequences are described in U.S. Pat. Nos. 6,541,684; 6,720,478; 6,905,857 and 7,034,117. Another yeast protein that is homologous to RecA is the Dmc1 protein. RecA/Rad51 homologues in organisms other than *E. coli* and *S. cerevisiae* have been described. Morita et al. (1993) *Proc. Natl. Acad. Sci. USA* 90:6577-6580; Shinohara et al. (1993) *Nature Genet.* 4:239-243; Heyer (1994) *Experientia* 50:223-233; Maeshima et al. (1995) *Gene* 160:195-200; U.S. Pat. Nos. 6,541,684 and 6,905,857.

Herein, "RecA" or "RecA protein" refers to a family of RecA-like recombination proteins having essentially all or most of the same functions, particularly: (i) the ability to position properly oligonucleotides or polynucleotides on their homologous targets for subsequent extension by DNA polymerases; (ii) the ability topologically to prepare duplex nucleic acid for DNA synthesis; and, (iii) the ability of RecA/oligonucleotide or RecA/polynucleotide complexes efficiently to find and bind to complementary sequences. The best characterized RecA protein is from *E. coli*; in addition to the original allelic form of the protein a number of mutant RecA-like proteins have been identified, for example, RecA803. Further, many organisms have RecA-like strand-transfer proteins including, for example, yeast, drosophila, mammals including humans, and plants. These proteins include, for example, Rec1, Rec2, Rad51, Rad51B, Rad51C, Rad51D, Rad51E, XRCC2 and DMC1. An embodiment of the recombination protein is the RecA protein of *E. coli*. Alternatively, the RecA protein can be the mutant RecA-803 protein of *E. coli*, a RecA protein from another bacterial source or a homologous recombination protein from another organism.

Additional descriptions of proteins having recombinase activity are found, for example, in Fugisawa et al. (1985) *Nucl. Acids Res.* 13:7473; Hsieh et al. (1986) *Cell* 44:885; Hsieh et al. (1989) *J. Biol. Chem.* 264:5089; Fishel et al. (1988) *Proc. Natl. Acad. Sci. USA* 85:3683; Cassuto et al. (1987) *Mol. Gen. Genet.* 208:10; Ganea et al. (1987) *Mol. Cell Biol.* 7:3124; Moore et al. (1990) *J. Biol. Chem.*:11108; Keene et al. (1984) *Nucl. Acids Res.* 12:3057; Kimiec (1984) *Cold Spring Harbor Symp.* 48:675; Kimeic (1986) *Cell* 44:545; Kolodner et al. (1987) *Proc. Natl. Acad. Sci. USA* 84:5560; Sugino et al. (1985) *Proc. Natl. Acad, Sci. USA* 85: 3683; Halbrook et al. (1989) *J. Biol. Chem.* 264:21403; Eisen et al. (1988) *Proc. Natl. Acad. Sci. USA* 85:7481; McCarthy et al. (1988) *Proc. Natl. Acad. Sci. USA* 85:5854; and Lowenhaupt et al. (1989) *J. Biol. Chem.* 264:20568, which are incorporated herein by reference. See also Brendel et al. (1997) J. Mol. Evol. 44:528 541.

Examples of proteins having recombinase activity include recA, recA803, uvsX, and other recA mutants and recA-like recombinases (Roca (1990) *Crit. Rev. Biochem. Molec. Biol.* 25:415), sep1 (Kolodner et al. (1987) *Proc. Natl. Acad. Sci. U.S.A.* 84:5560; Tishkoff et al. (1991) *Molec. Cell. Biol.* 11:2593), RuvC (Dunderdale et al. (1991) *Nature* 354:506), DST2, KEM1 and XRN1 (Dykstra et al. (1991) *Molec. Cell.* *Biol.* 11:2583), STPa/DST1 (Clark et al. (1991) *Molec. Cell. Biol.* 11:2576), HPP-1 (Moore et al. (1991) *Proc. Natl. Acad. Sci. U.S.A.* 88:9067), other eukaryotic recombinases (Bishop et al. (1992) *Cell* 69:439; and Shinohara et al. (1992) *Cell* 69:457); incorporated herein by reference.

In vitro-evolved proteins having recombinase activity have been described in U.S. Pat. No. 6,686,515. Further publications relating to recombinases include, for example, U.S. Pat. Nos. 7,732,585, 7,361,641, 7,144,734. For a review of recombinases, see Cox (2001) *Proc. Natl. Acad. Sci. USA* 98:8173-8180.

Methods for Forming Nucleoprotein Filaments

In certain embodiments, a fusion molecule as disclosed herein is contacted with a nucleic acid to form a nucleoprotein filament, or "filament". The term filament, in the context of forming a structure with a recombinase, is a term known to artisans in these fields. The nucleoprotein filament so formed can then be, e.g., contacted with another nucleic acid or introduced into a cell. Methods for forming nucleoprotein filaments, wherein the filaments comprise polypeptide sequences having recombinase activity and a nucleic acid, are well-known in the art. See, e.g., Cui et al. (2003) *Marine Biotechnol.* 5:174-184 and U.S. Pat. Nos. 4,888,274; 5,763, 240; 5,948,653 and 7,199,281, the disclosures of which are incorporated by reference for the purposes of disclosing exemplary techniques for binding recombinases to nucleic acids to form nucleoprotein filaments.

In general, a molecule having recombinase activity is contacted with a linear, single-stranded nucleic acid. The linear, single-stranded nucleic acid may be a probe. The preparation of such single stranded nucleic acids are known. The reaction mixture typically contains a magnesium ion. Optionally, the reaction mixture is buffered and optionally also contains ATP, dATP or a nonhydrolyzable ATP analogue, such as, for example, γ-thio-ATP (ATP-γ-S) or γ-thio-GTP (GTP-γ-S). Reaction mixtures can also optionally contain an ATP-generating system. Double-stranded DNA molecules can be denatured (e.g., by heat or alkali) either prior to, or during, filament formation. Optimization of the molar ratio of recombinase to nucleic acid is within the skill of the art. For example, a series of different concentrations of recombinase can be added to a constant amount of nucleic acid, and filament formation assayed by mobility in an agarose or acrylamide gel. Because bound protein retards the electrophoretic mobility of a polynucleotide, filament formation is evidenced by retarded mobility of the nucleic acid. Either maximum degree of retardation, or maximum amount of nucleic acid migrating with a retarded mobility, can be used to indicate optimal recombinase:nucleic acid ratios. Protein-DNA association can also be quantitated by measuring the ability of a polynucleotide to bind to nitrocellulose.

Exogenous Sequences

The methods and compositions set forth herein can be used for targeted integration of exogenous sequences (also referred to herein as donor sequences) into a region of interest in the genome of a cell. Targeted integration of an exogenous sequence can occur by both homology-dependent and homology-independent mechanisms. The data provided herein show that broad applicability for these techniques across species and for broad incorporation of DNAs generally. Accordingly, embodiments include insertion of DNAs to treat the various conditions described herein, as well as therapies to insert wild-type non-defective DNAs into cells to replace defective nucleic acid sequences. Thus embodiments include exogenous nucleic acids directed to techniques and treatments for gene conversion, homology-independent gene targeting, homologous recombination, targeted mutagenesis, genetic diseases, transgenic animals, expression vectors, and administration into plants.

Exemplary exogenous sequences include, but are not limited to, cDNAs, promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

Protein expression constructs optionally include, e.g., cDNAs and transcriptional control sequences in operative linkage with cDNA sequences. Transcriptional control sequences include promoters, enhancers and insulators. Additional transcriptional and translational regulatory sequences which can be included in expression constructs include, e.g., internal ribosome entry sites, sequences encoding 2A peptides and polyadenylation signals. For optimal expression of one or more proteins encoded by exogenous sequences integrated into a genome, the chromosomal integration site should be compatible with high-level transcription of the integrated sequences, preferably in a wide range of cell types and developmental states. However, it has been observed that transcription of integrated sequences varies depending on the integration site due to, among other things, the chromatin structure of the genome at the integration site. Accordingly, genomic target sites that support high-level transcription of integrated sequences are desirable. Non-limiting examples of chromosomal regions that do not encode an essential gene and support high-level transcription of sequences integrated therein include the murine Rosa26 locus (and its human homologue), the human CCR5 locus and the AAV P1 integration site on human chromosome 19. Additional genomic target sites supporting high-level transcription of integrated sequences can be identified as regions of open chromatin as described, for example in U.S. Patent Application Publications 2002/0064802 (May 30, 2002) and 2002/0081603 (Jun. 27, 2002).

Cleavage enzyme recognition sites include, for example, sequences recognized by restriction endonucleases, homing endonucleases and/or meganucleases. Targeted integration of a cleavage enzyme recognition site (by either homology-dependent or homology-independent mechanisms) is useful for generating cells whose genome contains only a single site that can be cleaved by a particular enzyme. Contacting such cells with an enzyme that recognizes and cleaves at the single site facilitates subsequent targeted integration of exogenous sequences (by either homology-dependent or homology-independent mechanisms) and/or targeted mutagenesis at the site that is cleaved.

For certain embodiments, it is desirable that an integration site is not present in an essential gene (e.g., a gene essential for cell viability), so that inactivation of said essential gene does not result from integration of the exogenous sequences. On the other hand, if the intent is to disable gene function (i.e., create a gene "knock-out") targeted integration of an exogenous sequence to disrupt an endogenous gene is an effective method. In these cases, the exogenous sequence can be any sequence capable of blocking transcription of the endogenous gene or of generating a non-functional translation product, for example a short patch of amino acid sequence, which is optionally detectable (see above). In certain embodiments, the exogenous sequences can comprise a marker gene (described above), allowing selection of cells that have undergone targeted integration. In certain embodiments, it will also be desirable that integration of exogenous sequences not result in ectopic activation of one or more cellular genes (e.g., oncogenes). On the other hand, in the case of integration of promoter and/or enhancer sequences, ectopic expression may be desired.

In certain embodiments, targeted integration is used to insert a RNA expression construct, e.g., sequences responsible for regulated expression of micro RNA, siRNA or shRNA. Promoters, enhancers and additional transcription regulatory sequences, as described above, can also be incorporated in a RNA expression construct Probes The data presented herein shows that a probe may be associated with a nucleoprotein filament to direct the filament with specificity to a target on a host cell chromosome. A target refers to a predetermined molecule, tissue, or location that the user intends to bind with the probe. A probe, in the context of a nucleoprotein filament, refers to a nucleic acid with complementarity to a target nucleic acid sequence. Artisans are familiar with methods for identifying sites of interest and developing probes. Probes may be chosen as suited to the recombinase chosen. The size of the probe may, accordingly be chosen. Examples include probes with 60 bp or 1300 bp, or with a length in the range of about 10 and about 10,000 residues; artisans will immediately appreciate that all the ranges and values within the explicitly stated ranges are contemplated, e.g., from about 40 to about 5,000, from about 60 to about 1300, from about 10 to about 3000, at least 10, at least about 30.

The probes may be chosen with the degree of specificity intended. As demonstrated herein, exogenous sequences may be placed with a high degree of reproducible accuracy. The sequences may be placed in the targeted gene. The specificity of placement may be measured in basepairs (bp) by comparing the most upstream point of the probe to the most upstream point of the inserted exogenous sequence, with the difference between these two points being the distance from the probe to the site of insertion. Accordingly, exogenous nucleic acids may be placed, and probes may be designed for placement, with a predetermined specificity; for example, between about 200 to about 2000 bp. Artisans will immediately appreciate that all the ranges and values within the explicitly stated ranges are contemplated, e.g., less than about 500 bp, less than about 1000 bp, less than about 5000 bp, or from about 500 to less than about 5000 bp. A predetermined specificity may be measured in vitro using the zebrafish animal model and following the procedures in the Examples, with directly injected zebrafish embryos incorporating an exogenous DNA within the stated range with 90% accuracy as measured for the embryos that are successfully transfected.

Embodiments include probes directed to techniques and treatments for gene conversion, homology-independent gene targeting, homologous recombination, targeted mutagenesis, genetic diseases, transgenic animals, expression vectors, and administration into plants.

Applications

Because recombinases are strongly conserved, among both eukaryotes and prokaryotes, and because the recombination-promoting activity of the fusion proteins disclosed herein does not depend upon the presence of a binding site for the sequence-specific DNA-binding domain present in the fusion protein, the disclosed methods and compositions will be widely applicable in many species. These include, but are not limited to, prokaryotes, eukaryotes, plants, metazoans, vertebrates, mammals and humans. Plants include monocotyledonous and dicotyledonous species. Exemplary plants include *Arabadopsis*. Exemplary metazoans include fruit flies (*Drosophila*), roundworms (*Caenorhabditis*). Exemplary vertebrates include frogs (e.g., *Xenopus*) fish (e.g., *Danio*). Exemplary mammals include bovines, porcines, ovines, caprines, equines, felines, canines, murines, and humans.

The methods and compositions disclosed herein will find use in both research and therapeutic applications, as will now be described.

Gene Conversion

In certain embodiments, introduction, into a cell, of a fusion molecule comprising a recombinase domain and a sequence-specific DNA-binding domain leads to an overall, genome-wide, increase in recombinational events, which can be manifested as gene conversion or loss of heterozygosity. Selection of a recombinational event of interest allows the isolation of novel sequences, including, for example, different alleles or haplotypes of genomic sequences, mutant sequences, wild-type sequences, insertions, deletions or rearrangements.

The DNA cleavage activity of a recombinase domain can be targeted by formation of a nucleoprotein filament containing a fusion molecule comprising the recombinase domain, as disclosed herein, and a sequence homologous to a genomic sequence of interest. Such fusion molecules, when introduced into a cell, can facilitate targeted mutagenesis in a genomic region of interest resulting from cleavage in the region of interest followed by non-homologous end-joining. Such mutations can result, for example, in gene knock-outs, e.g., for functional genomics or target validation.

Targeted DNA cleavage, mediated either by a fusion molecule as disclosed herein or by a nucleoprotein filament as disclosed herein, conducted in the absence of an exogenous polynucleotide (preferably in S or $G_2$ phase), can also stimulate recombination between homologous chromosomes.

Homology-Independent Gene Targeting

Integration of exogenous sequences at a region of interest in a genome, when the exogenous sequences lack homology to the region of interest, is facilitated by introducing into a cell, along with the exogenous sequences, a nucleoprotein filament made up of sequences homologous to the region of interest coated with fusion molecules comprising a recombinase domain and a sequence-specific DNA-binding domain. Inclusion of the sequence-specific DNA-binding domain in the fusion protein increases the frequency of recombination observed compared to instances in which a nucleoprotein filament is formed using a recombinase alone. It is not necessary that a target sequence, or binding site, for the sequence-specific DNA-binding domain be present in either the exogenous sequence or the genomic region of interest.

Without wishing to be bound by any particular theory, a possible explanation for the ability of nucleoprotein filaments comprising the fusion proteins disclosed herein to stimulate gene targeting is that the recombinase portion of the fusion protein catalyzes double-stranded breaks in genomic DNA homologous to the nucleotide sequence of the DNA component of the filament. It is well-known that double-stranded breaks in cellular DNA stimulate cellular repair mechanisms, by several thousand-fold, in the vicinity of the cleavage site, facilitating both homology-dependent (see below) and homology-independent integration of exogenous sequences. See, for example, Rouet et al. (1994) *Mol. Cell. Biol.* 14:8096-8106; Choulika et al. (1995) *Mol. Cell. Biol.* 15:1968-1973; Donoho et al. (1998) *Mol. Cell. Biol.* 18:4070-4078; Johnson et al. (2001) *Biochem. Soc. Trans.* 29:196-201; and Yanez et al. (1998) *Gene Therapy* 5:149-159.

Targeted non-homology-dependent integration, as described above, can be used, e.g., for purposes of cell engineering and/or protein overexpression. Embodiments include donor sequences that lack homology to the host DNA and/or that lack homology to the intended site of insertion. For instance, the donor nucleic acid may be designed or chosen to lack homology to nucleic acids at or near the site targeted by the probe, e.g., within 0 to 500,000 bp of the probe; artisans will immediately appreciate that all the ranges and values within the explicitly stated ranges are contemplated, e.g., within about 100,000 bp. The lack of homology can be, for example, having no more than 50% sequence identity and/or lacking in specific hybridization at low stringency. The lack of homology can further include a criterion of having no more than 9 bp identity. Further criteria for non-homology may be inferred from the following discussion of homologous recombination. Embodiments include cells, in vitro cells, cells treated ex vivo for reincorporation into the host animal (e.g., human), in vivo cells, animals, transgenic animals, and synthetic DNA modified with non-homologous donor DNA, as well as systems and methods for producing the same as disclosed herein.

Homologous Recombination

Also described herein are methods of facilitating homologous recombination between a chromosomal locus and an exogenous nucleic acid bearing sequences that are homologous to the chromosomal locus (e.g., gene targeting). Such mechanisms can result either in the replacement of a genomic sequence (e.g., a region of interest in a cellular genome) with a homologous non-identical sequence or in the insertion, into a genome, of exogenous sequences not normally present in that genome (provided that the sequences not normally present in the genome are linked, in the exogenous nucleic acid, with sequences that are homologous to a region of interest in the genome). Embodiments include cells, in vitro cells, cells treated ex vivo for reincorporation into the host animal (e.g., human), in vivo cells, animals, transgenic animals, and synthetic DNA modified with homologous donor DNA, as well as systems and methods for producing the same as disclosed herein.

The disclosed methods for targeted recombination involve the introduction, into a cell, of an exogenous nucleic acid comprising sequences homologous to the region of interest, along with a fusion molecule comprising a recombinase domain and a sequence-specific DNA-binding domain. The fusion molecules have been described above and optionally comprise a nuclear localization signal. The exogenous nucleic acid sequence, also referred to herein as a "donor sequence," can be introduced into the cell prior to, concurrently with, or subsequent to, introduction of the fusion molecule.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. Similarly, two alleles of a gene are homologous, non-identical sequences, as are two haplotypes of a particular genomic locus.

Embodiments include an exogenous, or donor, nucleic acid that contains substantial homology, which is sufficient homology to a genomic sequence to support homologous recombination (or homology-directed repair) between it and the genomic sequence to which it bears homology: approximately 25, 50 100, 200, 500, 750, 1,000, 1,500, 2,000 nucleotides or more of sequence homology between a donor and a genomic sequence (or any integral value between 10 and 2,000 nucleotides, or more) will generally support homologous recombination therebetween. Donor sequences can range in length, for example, from 10 to 10,000 nucleotides (or any integral value of nucleotides therebetween) or longer. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present. Alternatively, a donor sequence can contain a non-homologous sequence flanked by two regions of homology, or a homologous sequence flanked by two regions of non-homology. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequences in the region of interest.

Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present; artisans will immediately appreciate that all the ranges and values within the explicitly stated values are contemplated.

Thus, in certain embodiments, the degree of homology between two sequences (e.g. a genomic locus and an exogenous nucleic acid) is substantial to allow homologous recombination therebetween. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., a donor polynucleotide) of between 20 and 10,000 nucleotides or nucleotide pairs can be used.

Techniques for determining nucleic acid and amino acid sequence identity and homology are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.).

Another method of establishing percent identity is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed in which default parameters are used for the scoring table (for example, gap open penalty of 12, gap extension penalty of one, and a gap of six). From the data generated, the "Match" value reflects sequence identity.

Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the World Wide Web at ncbi.nlm.gov/cgi-bin/-BLAST. With respect to sequences described herein, the range of desired degrees of sequence identity is approximately 80% to 100% and any integer value therebetween. Typically the percent identities between sequences are at least 70-75%, alternatively 80-82%, alternatively 85-90%, 92% or more, 95% or more, 98% or more, or 99% or more.

Alternatively, the degree of sequence similarity between polynucleotides can be determined by hybridization of polynucleotides under conditions that allow formation of stable duplexes between homologous regions, followed by assay for double-stranded nucleic acid (e.g., hyperchromicity, binding to hydroxyapatite, or digestion with single-stranded-specific nuclease(s), and size determination of the digested fragments). Two nucleic acid, or two polypeptide sequences are substantially homologous to each other when the sequences exhibit at least about 70%-75%, alternatively 80-82%, alternatively 85%-90%, 92% or more, 95% or more, 98% or more, or 99% or more sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; Nucleic Acid Hybridization: A Practical Approach, editors B. D. Hames and S. J. Higgins, (1985) Oxford; Washington, D.C.; IRL Press.

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a homologous or identical target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then, by selection of appropriate conditions, the probe and the reference sequence selectively hybridize, or anneal, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, polyethylene glycol), hybridization reaction temperature and time parameters and wash conditions.

The exogenous, donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus).

In additional embodiments, the ends of an exogenous donor nucleic acid molecule can be modified in ways that make it a more suitable substrate for recombination. For example, an exogenous nucleic acid molecule for integration into a genome, by either a homology-dependent or a non-homology-dependent mechanism, can contain 3'-protruding single-stranded ends ("3' overhangs"). Methods for generating such ends (e.g., treating linear double-stranded DNA with 5'-specific exonucleases, such as λ exonuclease or T7 exonuclease) are known in the art.

Ancillary Methods for Enhancing Recombination Frequency

Methods and compositions are also provided that enhance levels of targeted recombination including, but not limited to, the use of cDNAs and/or engineered transcription factors to increase expression of genes involved in homologous recombination, such as, for example, members of the RAD52 epistasis group (e.g., Rad50, Rad51, Rad51B, Rad51C, Rad51D, Rad52, Rad54, Rad54B, Mre11, XRCC2, XRCC2, XRCC3), genes whose products interact with the aforementioned gene products (e.g., BRCA1, BRCA2) and/or genes in the NBS1 complex. When homologous recombination is desired, similar methods can be used, in combination with the methods and compositions disclosed herein, to repress expression of genes involved in non-homologous end joining (e.g., Ku70/80, XRCC4, poly(ADP ribose) polymerase, DNA ligase 4). See, for example, Yanez et al. (1998) *Gene Therapy* 5:149-159; Hoeijmakers (2001) *Nature* 411:366-374; Johnson et al. (2001) *Biochem. Soc. Trans.* 29:196-201; Tauchi et al. (2002) *Oncogene* 21:8967-8980. Methods for activation and repression of gene expression using fusions between a zinc finger binding domain and a functional domain are disclosed, for example, in U.S. Pat. Nos. 6,534,261; 6,824,978 and 6,933,113. Additional repression methods include the use of antisense oligonucleotides and/or small interfering RNA (siRNA or RNAi) targeted to the sequence of the gene to be repressed.

Additional proteins involved in gene conversion and recombination-related chromatin remodeling, which can be used in the aforementioned methods and compositions, include histone acetyltransferases (e.g., Esa1p, Tip60), histone methyltransferases (e.g., Dot1p), histone kinases and histone phosphatases.

The p53 protein has been reported to play a central role in repressing homologous recombination. See, for example, Valerie et al., (2003) *Oncogene* 22:5792-5812; Janz, et al. (2002) *Oncogene* 21:5929-5933. For example, the rate of homologous recombination in p53-deficient human tumor lines is 10,000-fold greater than in primary human fibroblasts, and there is a 100-fold increase in homologous recombination in tumor cells with a non-functional p53, compared to those with functional p53. Mekeel et al. (1997) *Oncogene* 14:1847-1857. In addition, overexpression of p53 dominant-negative mutants leads to a 20-fold increase in spontaneous recombination. Bertrand et al. (1997) *Oncogene* 14:1117-1122. Analysis of different p53 mutations has revealed that the roles of p53 in transcriptional transactivation and G1 cell cycle checkpoint control are separable from its involvement in homologous recombination. Saintigny et al. (1999) *Oncogene* 18:3553-3563; Boehden et al. (2003) *Oncogene* 22:4111-4117. Accordingly, downregulation of p53 activity can serve to increase the efficiency of targeted homologous recombination using the methods and compositions disclosed herein. Any method for downregulation of p53 activity can be used, including but not limited to cotransfection and overexpression of a p53 dominant negative mutant or targeted repression of p53 gene expression according to methods disclosed, e.g., in U.S. Pat. No. 6,534,261.

Further increases in efficiency of targeted recombination can be achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding such a protein into the cell or by activating expression of the gene encoding the protein in the cell. Cell-cycle arrest is also achieved by inhibiting the activity of cyclins and CDKs, for example, using RNAi methods (e.g., U.S. Pat. No. 6,506,559) or by inhibiting the expression of one or more genes involved in cell-cycle progression such as, for example, cyclin and/or CDK.

Targeted homology-dependent integration, as described above, can be used, e.g., for purposes of cell engineering and/or protein overexpression or to replace a wild-type sequence with a mutant sequence (or vice versa).

Targeted Mutagenesis

Any of the methods disclosed herein can be used for targeted mutagenesis by, for example, insertion of a sequence into a gene so as to disrupt the gene, introduction of a deletion, introduction of a point mutation or replacement of a gene by a non-functional allele. Such targeted mutagenesis can be used for a number of purposes. For example, targeted mutagenesis of genes encoding viral receptors (e.g., the CCR5 and CXCR4 receptors for HIV) can be used to render the receptors unable to bind to virus, thereby preventing new infection and blocking the spread of existing infections. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors can also be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Bimaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomaviruses (HPVs), and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses.

In similar fashion, the genome of an infecting bacterium can be mutagenized by one or more of the methods disclosed herein, to block or ameliorate bacterial infections.

Targeted DNA cleavage and targeted recombination, as disclosed herein, can be used to alter non-coding sequences (e.g., regulatory sequences such as promoters, enhancers, initiators, terminators, splice sites) to alter the levels of expression of a gene product. Such methods can be used, for example, for therapeutic purposes, functional genomics and/or target validation studies.

In additional embodiments utilizing the compositions and methods described herein, genes encoding HLA proteins involved in graft rejection can be cleaved, mutagenized or altered by recombination, in either their coding or regulatory sequences, so that their expression is blocked or they express a non-functional product. For example, by inactivating the gene encoding the common beta subunit gene (beta2-microglobulin), HLA class I null stein cells can be generated from any donor, thereby reducing the need for closely matched donor/recipient MHC haplotypes during stem cell grafting.

Genetic Diseases

The disclosed methods for targeted recombination (both homology-dependent and non-homology-dependent) can be used to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods of targeted recombination disclosed herein.

Exemplary genetic diseases include, but are not limited to, achondroplasia, achromatopsia, acid maltase deficiency, acquired immunodeficiencies, adenosine deaminase deficiency (OMIM No. 102700), adrenoleukodystrophy, aicardi syndrome, alpha-I antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, Fanconi's anemia, fibrodysplasia ossificans progressive, fragile X syndrome, galactosemis, Gaucher's disease, generalized gangliosidoses (e.g., GM1), hemochromatosis, hemoglobinopathies (e.g., sickle cell anemia, the hemoglobin C mutation in the $6^{th}$ codon of beta-globin, alpha-thalassemia, beta-thalassemia), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, lysosomal storage diseases (e.g., Gaucher's disease, GM1, Fabry disease and Tay-Sachs disease), Marfan syndrome, Moebius syndrome, mucopolysaccahidosis (e.g. Hunter's disease, Hurler's disease), nail patella syndrome, nephrogenic diabetes insipdius, neurofibromatosis, Neimann-Pick disease, osteogenesis imperfecta, porphyria, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

In many of these cases, a region of interest comprises a mutation, and the exogenous, or donor nucleic acid comprises the corresponding wild-type sequence. Similarly, a wild-type genomic sequence can be replaced by a mutant sequence, if such is desirable. For example, overexpression of an oncogene can be reversed either by mutating the gene or by replacing its control sequences with sequences that support a lower, non-pathologic level of expression. As another example, the wild-type allele of the ApoAI gene can be replaced by the ApoAI Milano allele, to treat atherosclerosis. Indeed, any pathology dependent upon a particular genomic sequence, in any fashion, can be corrected or alleviated using the methods and compositions disclosed herein.

In certain cases, alteration of a genomic sequence in a pluripotent cell (e.g., a hematopoietic stem cell) is desired. Methods for mobilization, enrichment and culture of hematopoietic stem cells are known in the art. See for example, U.S. Pat. Nos. 5,061,620; 5,681,559; 6,335,195; 6,645,489 and 6,667,064. Treated stem cells can be returned to a patient for treatment of various diseases including, but not limited to, SCID and sickle-cell anemia.

The genome of totipotent stem cells can also be altered by the use of the methods and compositions disclosed herein. Totipotent stem cells are described, for example, in U.S. Pat. Nos. 5,843,780; 6,200,806 and 7,029,913. Totipotent stem cells can be cultured (e.g., U.S. Pat. Nos. 6,602,711 and 7,005,252) and differentiated into various types of pluripotent cells (e.g., U.S. Pat. Nos. 6,280,718; 6,613,568 and 6,887,706), which can also be used in the practice of the disclosed methods.

Similarly, the genomes of induced pluripotent stem cells (iPS cells) can also be modified according to the disclosed methods and compositions. Induced pluripotent stem cells are described, for example, in Yu et al. (2007) *Science* 318: 1917-1920 and Dimos et al. (2008) *Science* 321:1218-1221.

Accordingly, embodiments of the invention include direction of a proteinaceous fusion molecule, a probe, and an exogenous nucleic acid to an animal (includes human or non-human, mammalian, and vertebrate) to treat the animal. The exogenous nucleic acid expresses a protein that provides a therapeutic effect. In other cases, the offending genetic basis for the disease is deleted. The method may be performed without a vector, e.g., without a virus, and without a transposon.

Transgenic Animals

The disclosed methods and compositions can be used for generation of transgenic livestock and large mammals, as disclosed, for example, in U.S. Pat. No. 7,199,218, and U.S. Ser. No. 12/504,364 filed Jul. 16, 2009 (U.S. Pub. No 2010/0146655, Methods And Materials For Producing Transgenic Animals) the disclosures of which are hereby incorporated herein by reference for all purposes including the purposes of describing methods for making transgenic animals, methods for targeted genome alteration, and uses of transgenic animals. In all cases, the present specification controls in case of conflict with documents incorporated by reference.

Transgenic artiodactyls can be made (e.g., pigs, sheep, goats, and cows). The nucleated cells of the transgenic artiodactyls provided herein contain a nucleic acid construct described herein. As used herein, "transgenic artiodactyl" includes founder transgenic artiodactyls as well as progeny of the founders, progeny of the progeny, and so forth, provided that the progeny retain the nucleic acid construct. For example, a transgenic founder animal can be used to breed additional animals that contain the nucleic acid construct.

Tissues obtained from the transgenic artiodactyls (e.g., transgenic pigs) and cells derived from the transgenic artiodactyls (e.g., transgenic pigs) also are provided herein. As used herein, "derived from" indicates that the cells can be isolated directly from the animal or can be progeny of such cells. For example, brain, lung, liver, pancreas, heart and heart valves, muscle, kidney, thyroid, corneal, skin, blood vessels or other connective tissue can be obtained from a transgenic artiodactyl (e.g., transgenic pig). Blood and hematopoietic cells, Islets of Langerhans, beta cells, brain cells, hepatocytes, kidney cells, and cells from other organs and body fluids, for example, also can be derived from transgenic artiodactyls (e.g., transgenic pigs). Organs and cells from transgenic pigs can be transplanted into a human patient. For example, islets from transgenic pigs can be transplanted to human diabetic patients.

Various techniques known in the art can be used to introduce nucleic acid constructs into non-human animals to produce founder lines, in which the nucleic acid construct is integrated into the genome. Such techniques include, without limitation, pronuclear microinjection (U.S. Pat. No. 4,873,191), retrovirus mediated gene transfer into germ lines (Van der Putten et al. (1985) *Proc. Natl. Acad. Sci. USA* 82, 6148-1652), gene targeting into embryonic stem cells (Thompson et al. (1989) *Cell* 56, 313-321), electroporation of embryos (Lo (1983) *Mol. Cell. Biol.* 3, 1803-1814), sperm mediated gene transfer (Lavitrano et al. (2002) *Proc. Natl. Acad. Sci. USA* 99, 14230-14235; Lavitrano et al. (2006) *Reprod Fert. Develop.* 18, 19-23), and in vitro transformation of somatic cells, such as cumulus or mammary cells, or adult, fetal, or embryonic stem cells, followed by nuclear transplantation (Wilmut et al. (1997) *Nature* 385, 810-813; and Wakayama et al. (1998) Nature 394, 369-374). Pronuclear microinjection, sperm mediated gene transfer, and somatic cell nuclear transfer are particularly useful techniques.

Typically, in pronuclear microinjection, a nucleic acid construct described herein is introduced into a fertilized egg; 1 or 2 cell fertilized eggs are used as the pronuclei containing the genetic material from the sperm head and the egg are visible within the protoplasm. Pronuclear staged fertilized eggs can be obtained in vitro or in vivo (i.e., surgically recovered from the oviduct of donor animals). In vitro fertilized eggs can be produced as follows. For example, swine ovaries can be collected at an abattoir, and maintained at 22-28° C. during transport. Ovaries can be washed and isolated for follicular aspiration, and follicles ranging from 4-8 mm can be aspirated into 50 mL conical centrifuge tubes using 18 gauge needles and under vacuum. Follicular fluid and aspirated oocytes can be rinsed through pre-filters with commercial TL-HEPES (Minitube, Verona, Wis.). Oocytes surrounded by a compact cumulus mass can be selected and placed into TCM-199 Oocyte Maturation Medium (Minitube, Verona, Wis.) supplemented with 0.1 mg/mL cysteine, 10 ng/mL epidermal growth factor, 10% porcine follicular fluid, 50 μM 2-mercaptoethanol, 0.5 mg/ml cAMP, 10 IU/mL each of pregnant mare serum gonadotropin (PMSG) and human chorionic gonadotropin (hCG) for approximately 22 hours in humidified air at 38.7° C. and 5% $CO_2$. Subsequently, the oocytes can be moved to fresh TCM-199 maturation medium which will not contain cAMP, PMSG or hCG and incubated for an additional 22 hours. Matured oocytes can be stripped of their cumulus cells by vortexing in 0.1% hyaluronidase for 1 minute.

Mature oocytes can be fertilized in 500 µl MINITUBE PORCPRO IVF MEDIUM SYSTEM (Minitube, Verona, Wis.) in Minitube 5-well fertilization dishes. In preparation for in vitro fertilization (IVF), freshly-collected or frozen boar semen can be washed and resuspended in PORCPRO IVF Medium to $4 \times 10^5$ sperm. Sperm concentrations can be analyzed by computer assisted semen analysis (SPERMVISION, Minitube, Verona, Wis.). Final in vitro insemination can be performed in a 10 µl volume at a final concentration of approximately 40 motile sperm/oocyte, depending on boar. Incubate all fertilizing oocytes at 38.7° C. in 5.0% $CO_2$ atmosphere for 6 hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

Linearized nucleic acid constructs can be injected into one of the pronuclei then the injected eggs can be transferred to a recipient female (e.g., into the oviducts of a recipient female) and allowed to develop in the recipient female to produce the transgenic animals. In particular, in vitro fertilized embryos can be centrifuged at 15,000×g for 5 minutes to sediment lipids allowing visualization of the pronucleus. The embryos can be injected with approximately 5 picoliters of the transposon/transposase cocktail using an Eppendorf FEMTOJET injector and can be cultured until blastocyst formation (~144 hours) in NCSU 23 medium (see, e.g., WO/2006/036975). Rates of embryo cleavage and blastocyst formation and quality can be recorded.

Embryos can be surgically transferred into uteri of asynchronous recipients. For surgical embryo transfer, anesthesia can be induced with a combination of the following: ketamine (2 mg/kg); tiletamine/zolazepam (0.25 mg/kg); xylazine (1 mg/kg); and atropine (0.03 mg/kg) (all from Columbus Serum). While in dorsal recumbency, the recipients can be aseptically prepared for surgery and a caudal ventral incision can be made to expose and examine the reproductive tract. Typically, 100-200 (e.g., 150-200) embryos can be deposited into the ampulla-isthmus junction of the oviduct using a 5.5-inch TOMCAT® catheter. After surgery, real-time ultrasound examination of pregnancy can be performed using an ALOKA 900 ULTRASOUND SCANNER (Aloka Co. Ltd, Wallingford, Conn.) with an attached 3.5 MHz trans-abdominal probe. Monitoring for pregnancy initiation can begin at 23 days post fusion and can be repeated weekly during pregnancy. Recipient husbandry can be maintained as normal gestating sows.

In somatic cell nuclear transfer, a transgenic artiodactyl cell (e.g., a transgenic pig cell) such as an embryonic blastomere, fetal fibroblast, adult ear fibroblast, or granulosa cell that includes a nucleic acid construct described above, can be introduced into an enucleated oocyte to establish a combined cell. Oocytes can be enucleated by partial zona dissection near the polar body and then pressing out cytoplasm at the dissection area. Typically; an injection pipette with a sharp beveled tip is used to inject the transgenic cell into an enucleated oocyte arrested at meiosis 2. In some conventions, oocytes arrested at meiosis 2 are termed "eggs." After producing a porcine embryo (e.g., by fusing and activating the oocyte), the porcine embryo is transferred to the oviducts of a recipient female, about 20 to 24 hours after activation. See, for example, Cibelli et al. (1998) *Science* 280, 1256-1258 and U.S. Pat. No. 6,548,741. For pigs, recipient females can be checked for pregnancy approximately 20-21 days after transfer of the embryos.

Standard breeding techniques can be used to create animals that are homozygous for the target nucleic acid from the initial heterozygous founder animals. Homozygosity may not be required, however. Transgenic pigs described herein can be bred with other pigs of interest.

Once transgenic animals have been generated, expression of a target nucleic acid can be assessed using standard techniques. Initial screening can be accomplished by Southern blot analysis to determine whether or not integration of the construct has taken place. For a description of Southern analysis, see sections 9.37-9.52 of Sambrook et al., 1989, *Molecular Cloning, A Laboratory Manual*, second edition, Cold Spring Harbor Press, Plainview; N.Y. Polymerase chain reaction (PCR) techniques also can be used in the initial screening. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example *PCR Primer: A Laboratory Manual*, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis (1992) *Genetic Engineering News* 12, 1; Guatelli et al. (1990) *Proc. Natl. Acad. Sci. USA* 87, 1874-1878; and Weiss (1991) *Science* 254, 1292-1293. At the blastocyst stage, embryos can be individually processed for analysis by PCR, Southern hybridization and splinkerette PCR (see, e.g., Dupuy et al. *Proc Natl Acad Sci USA* (2002) 99(7):4495-4499).

Expression of a nucleic acid sequence encoding a polypeptide in the tissues of transgenic pigs can be assessed using techniques that include, without limitation, Northern blot analysis of tissue samples obtained from the animal, in situ hybridization analysis, Western analysis, immunoassays such as enzyme-linked immunosorbent assays, and reverse-transcriptase PCR (RT-PCR).

Administration

The fusion molecules, nucleoproteins and/or nucleic acids disclosed herein can be administered directly to a subject for therapeutic or prophylactic applications such as those described herein. Subjects can be animals or plants. In particular, plant subjects can be monocotyledonous or dicotyledonous. Animal subjects can be vertebrates, in particular mammals (e.g., livestock, pets), in particular primates, in particular humans.

In general, and in view of the discussion herein, reference to the introduction of a fusion protein into a subject can mean either that a fusion protein itself is introduced or that a nucleic acid encoding a fission protein is introduced in a form that can be expressed in the subject.

With respect to the introduction of nucleic acids and nucleoprotein filaments into cells, any of the well-known procedures for introducing nucleic acids into cells can also be used for introduction of nucleoprotein filaments. For example, methods of non-viral delivery of nucleic acids and nucleoprotein filaments include, but are not limited to, electroporation, lipofection, microinjection, biolistics, virosomes, liposomes, immunoliposomes, polycation or lipid:nucleic acid conjugates, polybrene, protoplast fusion, calcium phosphate-mediated transfection, DEAE-dextran-mediated transfection, naked DNA, artificial virions, and agent-enhanced uptake of DNA. Lipofection is described in e.g., U.S. Pat. Nos. 5,049, 386, 4,946,787; and 4,897,355) and lipofection reagents are available commercially (e.g., Transfectam™, Lipofectamine® and Lipofectin™). Cationic and neutral lipids that are suitable for efficient receptor-recognition lipofection of polynucleotides include those of Felgner, WO 91/17424 and WO 91/16024. Delivery can be to cells (in vitro or ex vivo administration) or target tissues (in vivo administration). See also Sambrook et al., supra and Ausubel et al., supra.

In the case of introduction of a fusion protein and an exogenous nucleic acid, the exogenous nucleic acid may be present in molar excess, as measured by the moles of fusion protein and moles of DNA strands of exogenous nucleic acid. For instance, the exogenous DNA fragment may be present in a molar concentration that exceeds the molar concentration of the fusion protein, with the excess optionally being at least 2-fold or between about 2-fold and 500-fold; artisans will immediately appreciate that all ranges and values between the explicitly stated values are contemplated, e.g., 10-fold or from about 5-fold to about 50-fold.

Expression Vectors

Nucleic acids can be cloned into various types of vectors for transformation into prokaryotic or eukaryotic cells for replication and/or expression, as is known in the art.

To obtain expression of, for example, a fusion protein, a nucleic acid encoding the fusion protein can be inserted into an expression vector that contains a promoter to direct transcription. Suitable bacterial and eukaryotic promoters are well known in the art and described, e.g., in Sambrook et al., Molecular Cloning, A Laboratory Manual (2nd ed. 1989; $3^{rd}$ ed., 2001); Kriegler, Gene Transfer and Expression: A Laboratory Manual (1990); and Ausubel et al., supra. Bacterial expression systems are available in, e.g., *E. coli, Bacillus* sp., and *Salmonella* (Palva et al. (1983) *Gene* 22:229-235). Kits for such expression systems are commercially available. Eukaryotic expression systems for mammalian cells, yeast, and insect cells are well known in the art and are also commercially available.

Nucleic acids can be incorporated into vectors. Vectors most often contain one or more expression cassettes that comprise one or more expression control sequences, wherein an expression control sequence is a DNA sequence that controls and regulates the transcription and/or translation of another DNA sequence or mRNA, respectively. Expression control sequences include, for example, promoter sequences, transcriptional enhancer elements, start codons, stop codons, and any other nucleic acid elements required for RNA polymerase binding, initiation, or termination of transcription. A wide range of expression control sequences is well known in the art and is commercially available. A transcriptional unit in a vector may thus comprise an expression control sequence operably linked to an exogenous nucleic acid sequence. For example, a DNA sequence is operably linked to an expression-control sequence, such as a promoter when the expression control sequence controls and regulates the transcription and translation of that DNA sequence. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

Administration, Carriers, Pharmaceutical Compositions

Administration of therapeutically effective amounts of the compositions disclosed herein is by any of the routes normally used for introducing macromolecules into ultimate contact with the tissue to be treated. Fusion molecules, or their encoding nucleic acids, or nucleoprotein filaments, are administered in any suitable manner, optionally in formulation with pharmaceutically acceptable carriers. Multiple compositions can be administered concurrently or separately by the same or different routes. Suitable methods for administering such compositions are available and are well-known to those of skill in the art, and, although more than one route can be used to administer a particular composition, a particular route can often provide a more immediate and more effective reaction than another route.

Pharmaceutical compositions are determined in part by the particular substance being administered, as well as by the particular method used to administer the substance. Accordingly, there are a wide variety of suitable formulations of pharmaceutical compositions. See, e.g., Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The pharmaceutical compositions of the present disclosure can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of the disclosed methods, compositions can be administered, for example, by intravenous infusion, orally, topically, intraperitoneally, intravesically or intrathecally. Formulations can be presented in unit-dose or multi-dose sealed containers, such as ampoules and vials. Administration can be accomplished via single or divided doses. Injection solutions and suspensions can be prepared from sterile lyophilates, powders, granules, and tablets.

Appropriate dosages will depend upon the desired effect, the size and/or weight of the subject, and the general health of the subject, and can be determined by dose escalation over several treatment sessions. The size of the dose can also be influenced by the existence, nature, and extent of any adverse side-effects that accompany administration.

The disclosed therapeutic compositions can include pharmaceutically acceptable materials, compositions or vehicles, such as a liquid or solid filler, diluent, excipient, solvent or encapsulating material, i.e., carriers. These carriers are involved in transporting the subject chemical from one organ, or region of the body, to another organ, or region of the body. Each carrier should be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in therapeutic compositions.

Administration into Plants

For delivery of polynucleotides and nucleoproteins into plant cells, nucleic acids can be cloned into intermediate vectors for transformation into prokaryotic or eukaryotic (e.g., plant) cells for replication and/or expression. Intermediate vectors for storage or manipulation of the nucleic acid or production of protein can be prokaryotic vectors, (e.g., plasmids), shuttle vectors, insect vectors, or viral vectors for example. Nucleic acids can also cloned into an expression vector, for administration to a bacterial cell, fungal cell, protozoal cell, or plant cell.

Plant expression vectors and reporter genes are generally known in the art. See, e.g., Gruber et al. (1993) in *Methods of Plant Molecular Biology and Biotechnology*, Bernard R. Glick and John E. Thompson, eds., CRC Press, Boca Raton, Fla. Such systems include in vitro and in vivo recombinant DNA techniques, and can utilize any other synthetic or natural recombination method. See, e.g., Transgenic Plants: A Production System for Industrial and Pharmaceutical Proteins, Owen and Pen eds., John Wiley & Sons, 1996; Transgenic Plants, Galun and Breiman eds., Imperial College Press, 1997; and Applied Plant Biotechnology, Chopra, Malik, and Bhat eds., Science Publishers, Inc., 1999.

The promoter used to direct expression of the nucleic acid of choice depends on the particular application. For example, a strong constitutive promoter is typically used for expression and purification. In contrast, when a protein is to be used in vivo, either a constitutive or an inducible promoter can be used, depending on the particular function of the encoded protein. In addition, a weak promoter can be used, when low but sustained levels of protein are required. The promoter typically can also include elements that are responsive to transactivation, e.g., hypoxia response elements and small molecule control systems such as tet-regulated systems and the RU-486 system. See, e.g., Gossen et al. (1992) *Proc. Natl. Acad. Sci USA* 89:5547-5551; Oligino et al. (1998) *Gene Ther.* 5:491-496; Wang et al. (1997) *Gene Ther.* 4:432-441; Neering et al. (1996) *Blood* 88:1147-1155; and Rendahl et al. (1998) *Nature Biotechnol.* 16:757-761.

Promoters suitable for use in plant expression systems include, but are not limited to, viral promoters such as the 35S RNA and 19S RNA promoters of cauliflower mosaic virus (CaMV) (Brisson et al. (1984) *Nature* 310:511-514) and the coat protein promoter of tobacco mosaic virus (TMV) (Takamatsu et al. (1987) *EMBO J.* 6:307-311); plant promoters such as the promoter for the gene encoding the small subunit of ribulose-1,5-bis-phosphate carboxylase (RUBISCO) (Coruzzi et al. (1984) *EMBO J.* 3:1671-1680; Broglie et al. (1984) *Science* 224:838-843; and plant heat shock promoters, e.g. soybean hsp17.5-E or hsp17.3-B (Gurley et al. (1986) *Cell. Biol.* 6:559-565). Other examples of promoters that can be used for expression in plant cells include promoters from tumor-inducing plasmids of *Agrobacterium tumefaciens*, such as the nopaline synthase (NOS) and octopine synthase promoters; bacterial T-DNA promoters such as mas and ocs promoters; or the figwort mosaic virus 35S promoter.

In certain embodiments, the cauliflower mosaic virus (CaMV) 35S promoter is used. The caulimorvirus family has provided a number of exemplary promoters for transgene expression in plants, in particular, the (CaMV) 35S promoter. See, e.g., Kay et al. (1987) *Science* 236:1299. Additional promoters from this family such as the figwort mosaic virus promoter, the Commelina yellow mottle virus promoter, and the rice tungro baciliform virus promoter have been described in the art, and can also be used in the methods and compositions disclosed herein. See, e.g., Sanger et al. (1990) *Plant Mol. Biol.* 14:433-443; Medberry et al. (1992) *Plant Cell* 4:195-192; Yin et at (1995) *Plant J.* 7:969-980.

Plant promoters can be modified, if desired, to affect their regulatory responsiveness. For example, the CaMV 35S promoter can be joined to the portion of the RUBISCO gene that represses the expression of RUBISCO in the absence of light, to create a promoter that is active in leaves, but not in roots. Constitutive plant promoters such as actin and ubiquitin, having general expression properties known in the art, can also be used. See, e.g., McElroy et al. (1990) *Plant Cell* 2:163-171; Christensen et al. (1992) *Plant Mol. Biol.* 18:675-689.

Additionally, depending on the desired tissue, expression can be targeted to the endosperm, aleurone layer, embryo (or its parts such as scutellum and cotyledons), pericarp, stem, leaves tubers, roots, etc. Examples of known tissue-specific promoters include the tuber-directed class I patatin promoter, the promoters associated with potato tuber ADPGPP genes, the soybean promoter of beta-conglycinin (7S protein) which drives seed-directed transcription, and seed-directed promoters from the zein genes of maize endosperm. See, e.g., Bevan et al. (1986) *Nucleic Acids Res.* 14:4625-4638; Muller et al. (1990) *Mol. Gen. Genet.* 224:136-146; Bray (1987) *Planta* 172:364-370; and Pedersen et al. (1982) *Cell* 29:1015-1026. Additional seed-specific promoters include the phaseolin and napin promoters.

Recombinant constructs can also include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding beta-glucuronidase (Jefferson (1987) *Plant Molec Biol. Rep.* 5:387-405), luciferase (Ow et al. (1986) *Science* 234:856-859), and the B and C1 gene products that regulate anthocyanin pigment production (Goff et al. (1990) *EMBO J.* 9:2517-2522).

Other elements optionally present in expression vectors include a replicon that functions in *E. coli* (or in another prokaryotic, plant or insect host cell), a selective marker that functions in a prokaryotic host, e.g., a gene encoding antibiotic resistance, to permit selection of bacteria that harbor recombinant plasmids, and unique restriction sites in nonessential regions of the vector to allow insertion of recombinant sequences.

Transformation systems for plants as known in the art. See, e.g., Weissbach & Weissbach, Methods for Plant Molecular Biology, Academic Press, NY, Section VIII, pp. 421-463 (1988); and Grierson & Corey, Plant Molecular Biology, 2d Ed., Blackie, London, Ch. 7-9 (1988). For example, *Agrobacterium* is often successfully employed to introduce nucleic acids into plants. Such transformation preferably uses binary *Agrobacterium* T-DNA vectors which can be used to transform dicotyledonous plants, monocotyledonous plants and plant cells. Bevan (1984) *Nuc. Acid Res.* 12:8711-8721; Horsch et al. (1985) *Science* 227:1229-1231; Bevan et al. (1982) *Ann. Rev. Genet.* 16:357-384; Rogers et al. (1986) *Methods Enzymol.* 118:627-641; and Hernalsteen et al. (1984) *EMBO J.* 3:3039-3041. In embodiments that utilize the *Agrobacterium* system for transforming plants, the recombinant DNA constructs typically comprise at least the right-hand T-DNA border sequence flanking the DNA sequences to be transformed into the plant cell. In preferred embodiments, the sequences to be transferred are flanked by the right- and left-hand T-DNA border sequences. The design and construction of such T-DNA based transformation vectors are well known to those skilled in the art.

Other gene transfer and transformation methods include, but are not limited to, protoplast transformation through calcium-, polyethylene glycol (PEG)- or electroporation-mediated uptake of naked DNA. (see, e.g., Paszlcowski et al. (1984) *EMBO J.* 3:2717-2722; Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276); electroporation of plant tissues (e.g., D'Halluin et al. (1992) *Plant Cell* 4:1495-1505); microinjection, silicon carbide-mediated DNA uptake (e.g., Kaeppler et al. (1990) *Plant Cell Reporter* 9:415-418), microprojectile bombardment (e.g., Klein et al. (1988) *Proc. Nat. Acad. Sci. USA* 85:4305-4309; and Gordon-Kamm et al. (1990) *Plant Cell* 2:603-618); direct gene transfer, in vitro protoplast transformation, plant virus-mediated transformation, liposome-mediated transformation, and ballistic particle acceleration (e.g., Paszkowski et al. (1984) *EMBO J.* 3:2717-2722; U.S. Pat. Nos. 4,684,611; 4,407,956; 4,536,475; Crossway et al. (1986) *Biotechniques* 4:320-334; Riggs et al. (1986) *Proc. Natl. Acad. Sci USA* 83:5602-5606; Hinchee et al. (1988) *Biotechnology* 6:915-921; and U.S. Pat. No. 4,945,050).

A wide variety of host cells, plants and plant cell systems can be used, including, but not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*).

Exogenous sequences can also be expressed in seeds (for example, canola, corn, soybean, rice and barley seed) using seed-based production techniques, and expression products can be recovered during seed germination, if desired. See, e.g., PCT Publication Numbers WO 99/40210; WO 99/16890; WO 99/07206; U.S. Pat. No. 5,866,121; and U.S. Pat. No. 5,792,933; and all references cited therein.

In additional embodiments, fusion molecules (e.g., fusion proteins) are administered directly to target plant cells (rather than introducing a nucleic acid encoding a fusion protein). In certain in vitro situations, target cells are cultured in a medium containing a fusion molecule as disclosed herein. An important factor in the administration of polypeptide compounds in plants is ensuring that the polypeptide has the ability to traverse a cell wall. However, proteins, viruses, toxins, ballistic methods and the like have the ability to translocate polypeptides across a plant cell wall.

For example, "plasmodesmata" is the term given to explain cell-to-cell transport of endogenous and viral proteins and ribonucleoprotein complexes (RNPCs) in plants. Examples of viruses which can be linked to a fusion molecule for facilitating its uptake into plant cells include, tobacco mosaic virus (Oparka et al. (1997) *Plant J.* 12:781-789); rice phloem thioredoxin (Ishiwatari et al. (1998) *Planta* 205:12-22); and potato virus X (Cruz et al. (1998) *Plant Cell* 10:495-510). Other suitable chemical moieties that provide enhanced cellular uptake can also be linked, either covalently or non-covalently, to fusion molecules to facilitate penetration of a plant cell. Toxin molecules also have the ability to transport polypeptides across cell walls.

Particle-mediated delivery techniques (e.g., ballistic injection) as described above regarding nucleic acids can also be used to introduce polypeptides into a plant cell.

Nucleic Acids

Certain embodiments are directed to nucleic acids. As used herein, the term nucleic acid refers to both RNA and DNA, including siRNA, shRNA, miRNA, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). An isolated nucleic acid refers to a nucleic acid that is separated from other nucleic acid bases that are present in a genome, including nucleic acids that normally flank one or both sides of a nucleic acid sequence in a vertebrate genome (e.g., nucleic acids that flank a gene). A conservatively substituted nucleic acid refers to the substitution of a nucleic acid codon with another codon that encodes the same amino acid and also refers to nucleic acids that encode conservatively substituted amino acids, as described herein with respect to polypeptides. Significantly, the combination of potential codons for a polypeptide of only about six residues is manageably small.

The nucleic acid sequences set forth herein are intended to represent both DNA and RNA sequences, according to the conventional practice of allowing the abbreviation "T" stand for "T" or for "U", as the case may be, for DNA or RNA. Polynucleotides are nucleic acid molecules of at least three nucleotide subunits. Polynucleotide analogues or polynucleic acids are chemically modified polynucleotides or polynucleic acids. In some embodiments, polynucleotide analogues can be generated by replacing portions of the sugar-phosphate backbone of a polynucleotide with alternative functional groups. Morpholino-modified polynucleotides, referred to herein as "morpholinos," are polynucleotide analogues in which the bases are linked by a morpholino-phosphorodiamidate backbone (see, e.g., U.S. Pat. Nos. 5,142,047 and 5,185,444). In addition to morpholinos, other examples of polynucleotide analogues include analogues in which the bases are linked by a polyvinyl backbone, peptide nucleic acids (PNAs) in which the bases are linked by amide bonds formed by pseudopeptide 2-aminoethyl-glycine groups, analogues in which the nucleoside subunits are linked by methylphosphonate groups, analogues in which the phosphate residues linking nucleoside subunits are replaced by phosphoroamidate groups, and phosphorothioated DNAs, analogues containing sugar moieties that have 2' O-methyl group). Polynucleotides of the invention can be produced through the well-known and routinely used technique of solid phase synthesis. Alternatively, other suitable methods for such synthesis can be used (e.g., common molecular cloning and chemical nucleic acid synthesis techniques). Similar techniques also can be used to prepare polynucleotide analogues such as morpholinos or phosphorothioate derivatives. In addition, polynucleotides and polynucleotide analogues can be obtained commercially. For oligonucleotides, examples of pharmaceutically acceptable compositions are salts that include, e.g., (a) salts formed with cations such as sodium, potassium, ammonium, etc.; (b) acid addition salts formed with inorganic acids, for example, hydrochloric acid, hydrobromic acid (c) salts formed with organic acids e.g., for example, acetic acid, oxalic acid, tartaric acid; and (d) salts formed from elemental anions e.g., chlorine, bromine, and iodine.

Kits

Another aspect of this disclosure relates to kits for carrying out the administration of a fusion molecule, the administration of a nucleic acid encoding a fusion polypeptide, the administration of a nucleoprotein comprising a fusion molecule, or the administration of a nucleoprotein and a nucleic acid. In one embodiment, the kit comprises a nucleoprotein comprising a nucleic acid that is complementary or homologous to a nucleotide sequence of interest, optionally formulated in a pharmaceutical carrier. In another embodiment, the kit comprises a nucleoprotein comprising a nucleic acid that is complementary or homologous to a nucleotide sequence of interest, and at least one nucleic acid for insertion into a genome in the vicinity of the sequence of interest, formulated as appropriate, in one or more separate pharmaceutical preparations. The nucleoprotein and the nucleic acid can be formulated together in a single preparation or can be supplied as separate preparations. Kits may include components and/or instructions for embodiments as set forth herein, including the section entitled Additional Description.

Various publications are cited herein. These publications, including all patent applications, patents, and journal articles, are hereby incorporated herein by reference for all purposes; in the case of conflict, the present specification is controlling.

EXAMPLES

Example 1

Construction of NLS/RecA/Gal4 Fusion Molecule

A full-length RecA protein, fused at its N-terminus with a nuclear localization signal (NLS) and at its C-terminus to the Gal4 DNA-binding domain (NLS/RecA/Gal4) was constructed by fusing the full-length sequence encoding bacterial RecA and the yeast Gal4 DNA binding domain. Sequences were amplified with the proofreading polymerase Pfx50 (Invitrogen, Carlsbad, Calif.) from pBEU14 RecA (Uhlin and Clark, 1981) and pGBT9 Gal4 plasmids (Clontech, Mountain View, Calif.). The N-terminus of RecA was fused with a nuclear localization signal (NLS) from SV40 Large T Antigen to promote nuclear targeting (Keller et al., 2003). NLS in 5' terminal of each fusion protein was added using the following primer: 5'-CATATGCCACCTAAAAAGAA-GAGAAAGGTAGAAGACCCCAAG ATGGCTATCGAC-GAAAACAA-3' (SEQ ID NO: 7). The NLS had the amino acid sequence PPKKKRKVEDPK (SEQ ID NO:1). The Gal4 DNA-binding domain contained amino acids 1 to 147 of the Gal4 protein and had the amino acid sequence MKLLSS-IEQACDICRLKKLKCSKEKPKCAKCLKN-NWECRYSPKTKRSPLTRAHL TEVESRLERLEQLFL-LIFPREDLDMILKMDSLQDIKALLTGLFVQDNVNKD AVTD RLASVETDMPLTLRQHRISATSS-SEESSNKGQRQLTVS (SEQ ID NO:2). The NLS/RecA/Gal4 fusion protein also contained a His$_s$ tag at carboxy terminus (521-528 amino acids) to aid in purification. The complete amino acid sequence of the fusion protein is shown in FIG. 1 (SEQ ID NO:3). The nucleotide sequence encoding the NLS/RecA/Gal4 fusion protein is given in FIG. 2 (SEQ ID NO:4).

The fusion protein was expressed in *E. coli* BL21(DE3) pLysS_Cam$^+$. Protein blot analysis of the lysates using a goat-anti-RecA antibody showed that the 58 kD fusion protein was abundantly expressed following induction with 1 mM IPTG for 2 hours or 16 hours. The protein was purified from lysates of induced cells using a Ni$^+$ column.

Example 2

Construction of NLS/RecA

A NLS/RecA fusion was also constructed by as above for NLS/RecA/Gal4 except the following primer following 3' primer was used: 5'-GATCGCGGCCGCAAAATCTTCGT-TAGTTTCTG-3', (SEQ ID NO:8). The amino acid sequence of the NLS/RecA fusion protein is shown in FIG. 3, (SEQ ID NO:5). The nucleotide sequence encoding the NLS/RecA fusion protein is given in FIG. 4, (SEQ ID NO:6).

Example 3

Formation of Nucleoprotein Filaments with Fusion Molecules

To test whether the fusion molecules retained the RecA-mediated ability to form nucleoprotein filaments on single-stranded DNA, an in vitro reaction, containing the nonhydrolyzable ATP analogue ATP-γ-S, was used. Stasiak et al. (1994) *Experientia* 50:192-203, Baliga et al. (1995) *Proc. Natl. Acad. Sci. USA* 92:10393-10397. 10~20 ng of dsDNA (~250 bp) from the floating head gene in zebrafish diluted in water into 4.0 μl. This DNA was not exposed to Ethidium Bromide (EtBr). dsDNA was denatured by heating to 95° C. in a temperature cycler (MASTERCYCLER EPGRADIENT S, Eppendorf, Hamburg, Germany) for 12 minutes and chilled on ice for two minutes. Then was added 0.8 μl of coating buffer (100 mM TrisOAc, pH 7.5; 500 mM NaOAc; 10 mM DTT, 10 mM Mg(OAc)$_2$), 0.6 μl of 16.2 mM ATPγS (from Sigma), and 100-200 ng of RecA, NLS-RecA or NLS-RecA-Gal4 into 4.0 μl cssDNA probes. Water was then added to a 7.0 ul reaction volume that was incubated immediately at 37° C. for 30 minutes to make DNA-RecA filaments.

The ability of NLS-RecA-Gal4 protein was tested for its ability to coat single stranded (ss) DNA. An in vitro reaction with purified protein, single stranded DNA, and a non-hydrolysable form of ATP, ATP-γ-S was used to test coating activity. For this, complementary (c), denatured ssDNA (cssDNA) corresponding to the flh locus was used (250 nucleotides for each strand). Following coating, the DNA was analyzed on a standard agarose gel for mobility shift. RecA efficiently coated cssDNA, resulting in a predicted mobility shift of the single-stranded DNA after electrophoresis. In contrast, incubation with an equivalent amount of BSA instead of RecA did not result in a mobility shift of the DNA (data not shown). Similar to native RecA, the NLS-RecA-Gal4 protein also coated the cssDNA and caused a mobility shift, indicating that the NLS-RecA-Gal4 fusion protein retained the ability to bind cssDNA. However, the much of the coated cssDNA often failed to migrate into the agarose gel, suggesting the formation of higher order structures between the NLS-RecA-Gal4 filaments. These complexes could be a result of the dimerization domain in the Gal4 DNA-binding region.

Example 4

Figure 6:
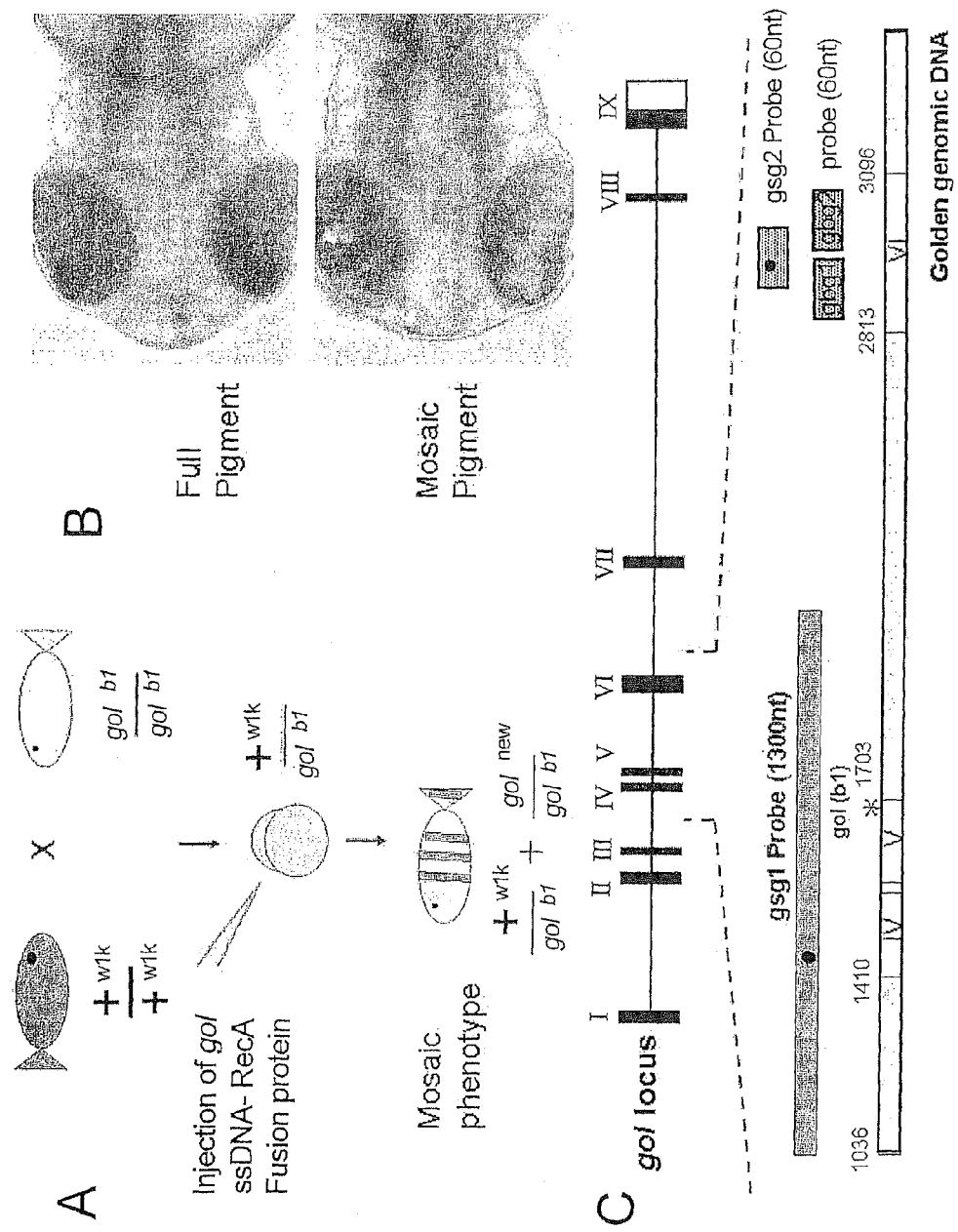
FIG. 6 depicts results that show that injection of complementary ssDNA-NLS-RecAGal4 filament leads to site-specific insertion. As depicted, this filament causes loss of herterozygosity (LOH) in heterozygous gol embryos, resulting in mosaic eye pigmentation. Panel A: Genotype of the embryos used for injection. All embryos were injected under the one-cell stage. Panel B: Dorsal views of eyes at 3 dpf showing wild type pigmentation patterns in a non-injected embryo (upper panel) and mutant patterns (bottom panel) by injected gol oligonucleotides-NLS-RecA-Gal4 targeting filaments. Injection of targeting filament results in loss of heterozygosity at the gol locus. Panel C: Four gol targeting probes coated by NLS-RecA-Gal4 are designed to target either exon4/5 or exon6 region. Gsg1 and gsg2 probes carry stop codon mutation within the DNA probes which show by filled circle. Gbg1 and gbg2 probes are 60 nt in length and synthesized to adjacent genomic DNA sequences. These two probes do not contain mutations.

Fusion Proteins for Targeted Gene Disruption cssDNA RecA filaments produced with different RecA fusion proteins stimulated targeted gene disruption of chromosomal regions homologous to the ssDNA Design of RecA filament experiments. Different RecA fusion proteins were tested for the ability to induce loss of heterozygosity (LOH) at specific loci in zebrafish. A fusion from the N- to C-termini between the SV40 nuclear localization signal (NLS) from SV40 Large T Antigen, RecA and the DNA-binding domain of Gal4, NLS-RecA-Gal4 protein (FIG. 5, panel A), had marked activity to induce LOH at a specific locus in zebrafish. The NLS sequence was present to enhance nuclear targeting of ssDNA-RecA filaments. The activity of the NLS-RecA-Gal4 recombinant protein was compared to NLS-RecA that lacked the Gal4 domain (FIG. 5, panel B). The Gal4 DNA binding region contained both a dimerization and metal-binding/DNA recognition domain that may contribute to the observed activity to induce LOH at specific loci. For this reason, the activity of NLS-RecA-Gal4 was compared to an NLS-RecA-Gal4 fusion protein that lacked the dimerization domain of Gal4 but retains the DNA-binding domain, termed NLS-RecA-Gal4ΔDD (FIG. 5, Panel C). cssDNA-RecA filaments complementary to the golden (gol) locus were injected into one-cell stage zebrafish embryos that were heterozygous for the $gol^{b1}$ allele (FIG. 6, panel A). Following injection, embryos were examined for LOH at the gol locus at 3 days post fertilization (dpf).

The gol locus was targeted for several reasons. First, the gol locus is required in a cell-autonomous manner for pigmentation (Streisinger et al., 1989), providing a direct relationship between phenotype and genotype and allowing individual cells to be examined for pigment production. Pigmentation of zebrafish embryos is visible from day 2 of development (Feitsma et al., 2008). Second, homozygous recessive gol mutants are viable but lack dark pigmentation in the retinal epithelial cells and the melanocytes. gol heterozygotes display normal or wild type levels of pigmentation (FIG. 6, Panel B). LOH in gol heterozygous embryos results in clear patches in the eye that lack pigmentation (FIG. 6, panel B) (Moore et al., 2006). This allows for rapid screening of a visible phenotype in a mutated gene that is not essential for embryogenesis. Third, the gene corresponding to the gol mutation, named slc24a5, is cloned and the genomic region containing the gol locus is well characterized (Lamason et al., 2005).

Results

A 1300 bp piece of DNA complementary to a region spanning from intron 3 to intron 5 of gol gene that contained a mutated exon 4 was used (called gol-1300 in FIG. 6, Panel C). The mutation in exon 4 results in a premature stop codon and was designed to replace an endogenous HgaI restriction enzyme recognition site in exon 4 to create a restriction fragment length polymorphism (RFLP) if it were recombined into the endogenous gol locus. The 1300 bp DNA was denatured and coated with NLS-RecA-Gal4 to produce cssgol-1300-NLS-RecA-Gal4 filaments. Following injection of these filaments into golb1 heterozygous embryos, 2.9% of the injected embryos displayed LOH at the gol locus as displayed by loss of pigmentation in patches of the retinal epithelium (Table I). As a control, the NLS-RecA-Gal4 protein was mixed with gol-1300 that was not denatured and injected into golb1 heterozygous embryos. This condition did not show detectable levels of LOH at the gol locus. These results indicated that the cssgol-1300-NLS-RecA-Gal4 filaments were able to mutate the wild type copy of gol. We expect that the frequency at which this occurs is double of what was detected as disruption of the golb1 allele will not lead to a detectable phenotype. Analysis of DNA isolated from embryos containing mosaic patterns of pigmentation did not show a RFLP (data not shown). This result indicated that the single stranded DNA in the filament was not substituted into the chromosomal DNA, i.e., the LOH observed at the gol locus was not induced by homologous DNA replacement.

Smaller cssgol-NLS-RecA-Gal4 filaments were also tested and also found to induce LOH at the gol locus. 60 bp oligos were designed that were complementary to exon 6, named ssgolex6m-60 sense (s) and ssgolex6m-60 antisense (a) (FIG. 6). Similar to the gol-1300 fragment, the oligos were designed to contain stop codons located in the center of the 60 bp sequence and create a RFLP if the oligos were in replaced by recombination with the endogenous gol gene. The RFLP would be detected as a change from an endogenous AfeI to artificial HindIII restriction site. When the 60 bp oligos were coated with NLS-RecA-Gal4 protein, mixed together and injected into gol heterozygous embryos, LOH was observed in 2.5% of the injected embryos as missing pigmentation in the eyes, similar to the frequency observed with the cssgol-1300-NLS-RecA-Gal4 filaments. Again, analysis of DNA isolated from embryos displaying LOH at the gol locus following injection of cssgolex6m-60-NLS-RecA-Gal4 filaments did not reveal a RFLP (data not shown). These results indicated that cssgol-NLS-RecA-Gal4 filaments as short at 60 bp are able to mutate the targeted gene, but are not induced by recombination.

To rule out that the induced LOH observed was a result of recombination of the cssDNA-NLS-RecA-Gal4 filaments, css oligos without stop codon were tested for the ability to promote LOH at the gol locus. For this, two adjacent pairs of short css gol oligos, named golex6-60-1 and -2, were designed complementary to exon 6 in the gol gene without point mutations (FIG. 6, Panel B). Injection of either complementary pair of golex6-60-1 or -2-NLS-RecA-Gal4 filaments into gol heterozygous embryos resulted in LOH at a frequency similar to the cssgolex6m-60-NLS-RecA-Gal4 filaments (FIG. 6, Panel B and Table I). This frequency was not enhanced by injection of both cssgolex6-60-1 and -2-NLS-RecA-Gal4 filaments and was dependent upon the NLS-RecA-Gal4 (Table I). These data support further that the cssDNA-NLS-RecA-Gal4 filaments promote LOH at the gol locus by a mechanism independent from recombination resulting in gene replacement.

A test was made to determine if both complementary ssDNA-NLS-RecA-Gal4 filaments were required to induce LOH. Injection of either sense or antisense ssgolex6m-60-NLS-RecA-Gal4 filaments alone into golb1 heterozygous embryos does not induce detectable LOH at the gol locus (Table I). Furthermore, when non-paired but adjacent filaments produced with NLS-RecA-Gal4 (either ssgolex6-60-1 sense with ssgolex6-60-2 antisense or ssgolex6-60-1 antisense with ssgolex6-60-2 sense) were injected into gol heterozygous embryos, the LOH was not observed (Table I). These results show that complementary ssDNA NLS-RecA-Gal4 filaments are required for high frequency induction of LOH at the gol locus.

To further test whether 5' phosphate group and 3'OH group are required for this gene targeting event, two modified pair of gsg2 oligos were synthesized and injected with NLSRecA-Gal4. One is the 5'-amino modified C6 group (5'AmC6)

which blocks the phosphate group on 5' end of oligos. 5' AmC6 was proved no effect for the binding ability of RecA protein, although it impaired the train formation of RecA filament (a concatenated form of RecA filament which can link up to at least 50 oligonucleotides) (Simonson et al., 1994). The other one is the inverted deoxythymidine 3' end modifier (3' InvdT) which blocks the 3' hydroxyl group of oligos and inhibits the DNA polymerase driven primer extension from the 3' end (Dames et al., 2007). As shown in Table I, injection by either 5'AmC6 or 3'InvdT oligos with NLSRecAGal4, both remain the activity to induce the LOH event in gol locus under consistent ratio without compromise, no matter which end is blocked.

Finally, to confirm the gene targeting specificity caused by the activity of RecA homologous searching, complementary non-gol oligos were designed with the same 60 nt length for the control experiment. This pair of non-specific probes was unable to cause the same LOH phenotype in gol locus as gol oligo-NLS-RecA-Gal4 filaments (Table I). This result shows the requirement of probe-directed specificity in this NLS-RecA-Gal4 assay.

Example 5

Site-Specific Insertion of an Exogenous Gene

The above data indicated that the cssDNA-NLS-RecA-Gal4 promoted LOH at the gol locus. Without being bound to a specific theory, it is believed that this effect was mediated by double-strand breaks (DSBs) in the targeted region. This example indicates that the DSB created by NLS-RecA-Gal4 filaments can be used to promote insertion of supplied exogenous DNA into specific loci. Without being bound to a specific theory, it is believed that NLSRecAGal4-filaments cause DSBs in target regions and then exogenous linear DNA can be incorporated into the site of the break during repair by the Non-homologous end joining (NHEJ) pathway. In this example, targeted insertion events were demonstrated by the tissue-specific expression of EGFP gene after co-injection with ssDNA-NLS-RecA-Gal4 filaments complementary to the gol, prominin1, and floating head (flh) loci (FIG. 7). The prominin1 gene was selected as a previously uncharacterized gene and for its specific expression in the dorsal diencephalon and retina during embryonic development. The genes were inserted without promoters, so that expression requires site-specific site insertion that engages endogenous promoters that provide for gene expression.

In order to follow the site-specific targeting event of gene expression driven by endogenous promoter, the strategy for targeting is similar to create gene targeting event as the one used in gol gene disruption as already described. For this, 200 to 300 bp of the target region of the gene is simply amplified by PCR, the amplification product is denatured by heating, and the single strands are coated by NLSRecAGal4 with additional co-injection with a linear fragment of DNA containing an EGFP reporter (FIG. 8). This type of tissue-specific EGFP expression was observed for 5 to 19% of the injected embryos from different targeting gene (Table II). In all cases very little off-target expression was observed (data not shown).

For the experiments shown here, the reporter gene is used as a cassette with a splice acceptor followed by EGFP in all three frames followed by polyA transcription terminal sequence without any promoter sequence (FIG. 8, Panel A). Since these reporter genes could insert in either direction, expression would be expected to observed in only 1 out of 6 insertions into the targeted gene. Therefore, it is believed that mutagenic load at the targeted locus may be at least 6-fold higher than what it can be observed by EGFP expression after injection. The expression of EGFP in this example is a marker to indicate the gene disruption event in wild type fish. Compared with heterozygous fish, homozygous wild type fish lack LOH phenotype for selection. Consequently, this EGFP insertion method will allow pre-screening by targeting event to grow to adulthood. This method is assumed will not only create mutations at specific loci but also allow following the expression of the endogenous locus.

Molecular evidence of targeting and insertion events was analyzed. Two regions of the gol gene (FIG. 8, Panel A) and one region of each flh and prominin1 gene were targeted (data not shown, but similar results were found). As shown below, highly specific targeted insertions were made into two distinct regions of the gol gene by choosing two different cssDNA-NLS-RecA-Gal4 filaments. In this example, the location between the two different probes is about 1 kb (FIG. 8, Panel A). Junction fragments were amplified between the exogenously supplied EGFP reporter DNA and the endogenous locus by PCR analysis. This analysis showed insertion into the gol locus at two distinct sites (FIG. 8, Panel B). These amplification products were verified by DNA sequencing and showed the correct sequences from the junction of endogenous locus and the exogenously supplied DNA. The junctions were found near the ends of the ssDNA filaments in many cases (FIG. 8, Panel C). As shown in FIG. 8, Panel C, the site of insertion was within about 500 bases of the probe. Accordingly, insertion may be made within about 500 base pairs of an intended site by choice of a probe Example 6

Co-Injection of Gol ssDNA-NLS-RecA-Gal4 Filaments with an Exogenous Gene Results in Mutations that Transmit through the Germline to the Next Generation Embryos displaying EGFP expression in the eye (FIG. 7) were selected after co-injection of gol cssDNA-NLS-RecA-Gal4 filaments with the EGFP reporter gene (FIG. 8) to grow to adulthood. Gol$^{b1}$ homozygous fish were used to make a complementation testcross with these founder F0 fish. Out of 21 F0 adults screened, only two F0 fish produced offspring that failed to complement the b1 allele (FIG. 9). These results demonstrate that this method can be used to target genes, screen fish, and transmit to germline. The germline of these two founder fish is highly mosaic, with 0.7 and 3.7% of the offspring from the two founders showing failure to complement the b1 allele (Table II). One of the F0 founders was injected with ssDNA-NLS-RecA-Gal4 filaments corresponding to probe A, and the other was injected with probe B filaments (FIG. 8). The recovery of two independent insertions at the gol locus using different probes shows that this method can be used to target any gene in the genome. Although the fluorescence from the EGFP reporter gene did not show in non-complementing offspring, the reason might be consequent with at least a 5-fold less possibility of in-frame EGFP expression event than gene disruption caused by DNA deletion or insertion in the gol locus.

Theories of Action

As per the Examples, it has been demonstrated that complementary (c) ssDNA-NLS-RecA-Gal4 filaments targeted to the gol locus are able to induce loss of heterozyogocity at this locus after injection into zebrafish embryos. This activity requires both the Gal4 DNA binding/dimerization domains in NLS-RecA-Gal4 and complementarity between the filaments. Without being bound to a particular theory, a model is proposed herein for this activity where the cssDNA-NLS-RecA-Gal4 filaments target the gol locus by creating arrested replication forks that result in double stranded breaks (DSBs) (FIG. 10).

The NLS-RecA-Gal4 protein is able to coat ssDNA (FIG. 8). When this DNA-protein complex is injected into the zebrafish embryos, the NLS signal apparently guides the complex into the nucleus of the embryonic cells. The activity of RecA in the filaments promotes a homology search to find homologous chromosomal DNA. Once the chromosomal target is located by homologous pairing, the cssDNA-NLS-RecA-Gal4 filaments initiate DNA strand invasion. During the stand invasion and strand exchange steps, the ssDNA filament will apparently invade and unwind its homologous double-stranded genomic DNA, resulting in the formation of D-loop structures. Due to the dimerization domain in Gal4, NLS-RecA-Gal4 is proposed to form a dimer and stabilize the complex of forward single strand (fss)-NLS-RecA-Gal4 and reverse single strand (rss)-NLS-RecA-Gal4 filaments on the targeting genomic region (FIG. 10). Because the ssDNA-RecA filament disassembles upon ATP hydrolysis (Sigurdsson et al., 2002), a non-hydrolytic form of ATP was used, ATPγS, for making stable cssDNA-NLS-RecA-Gal4 filaments. It has been noted that some proteins that tightly bind DNA, such as mutated transcription machinery, can impede replication fork progression on chromosomes, causing stalled or collapsed replication forks (Michel et al., 2001; Aguilera and Gomez-Gonzalez, 2008). Arrested replication forks can increase the stress on the chromosome, causing the formation of DNA DSB and replication fork collapse (Michel et al, 1997).

Arrested replication forks can be processed in repair-independent and repair-dependent manners. If this replication fork is not repaired, the free DNA fragment can be lost, causing a large deletion. Alternatively, the free DNA fragment may move to a different genomic region, resulting in a chromosomal translocation (Michel et al., 2001). A large deletion or translocation can cause a deficient haploid allele during meiosis in which the resulting phenotype can be detected by a complementation test or a single-generation haploid screening (Imai et al., 2000).

Arrested replication forks can be repaired by a variety of mechanisms that would be also consistent with our Preliminary Studies. Stalled replication forks can often trigger cell cycle arrest and stimulate DSB repair mechanism by either the HR or the NHEJ pathway. If the arrested replication fork is close to the telomere, one end of the double strand break (not from the two end double strand break) created by replication fork collapse can be repaired by break-induced replication (BIR) pathway (Smith et al., 2007; Llorente et al., 2008). During this process, the end of the chromosome is repaired by a form of homologous recombination using the sister chromosome as a template. This results in a long tract of LOH.

Two-end DSBs can also be made upon a replication fork collapse (Shrivastav et al., 2008). The two-end DSBs result by resolution of a Holliday junction (HJ) molecule after a "chicken foot" intermediate structure forms by regression of replication fork during the initiation of repair (Lundin et al., 2002). It has been shown that RecA and RecG protein are able to promote DNA replication fork regression for the DNA repair (Robu et al., 2001 and 2004). Either HR or NHEJ pathway can be used to repair this kind of two-end DNA DSB (Shrivastav et al., 2008).

Arrested replication forks are also a target for nuclease digestion, resulting in the formation of DSB (Michel, et al., 2001). For example in a Bacteriophage T4 model, T4 Endonuclease VII cleaves of arrested replication forks induced from an antitumor drug-topoisomerase complex (Hong and Kreuzer, 2003). In yeast, Mus81 and Mms4/Eme1 form a heterodimeric structure-specific endonuclease that can cleave branched DNA structures formed by Holliday junctions at stalled replication forks (Boddy et al., 2001; Lundin et al., 2002). This kind of DSB creates a shorter cleft than ones caused by replication fork collapse. Consequently, a short DSB is more efficiently paired by either the classical HR or the NHEJ pathway.

Therefore, in this model it is proposed that a cssDNA-NLS-RecA-Gal4 complex or other NLS-recombinase-DNA binding fusion protein can be used to induce targeted gene disruption by blockage of the DNA replication fork progression. This results in site-specific DSB that are repaired by either the endogenous HR or NHEJ pathway. The homologous searching activity of RecA can provide target specificity and the Gal4 dimerization domain may stabilize the complementary joint molecular complex in the targeted region of chromosome. This DNA-protein complex may also stack with other cssDNA-NLS-RecA-Gal4 filaments and form a high order structure to increase the strength of blockage of DNA replication fork. The arrested replication fork can either cause replication fork collapse or promote the accessibility of DNA endonucleases to induce DNA DSBs. This kind of targeted DSB is different from those randomly induced by stalled replication forks from chemical inhibition of replication (Feitsma et al., 2008) or mutant DNA binding proteins (Michel et al., 2001). Based on the results described herein and the proposed model, it is expected to promote the site-specific gene mutation by induction of DSB during the resolution of stalled replication forks. If the DSB is not repaired, large deletions and translocations are to be expected. If repaired by the NHEJ pathway, predominantly small deletions or insertions at the repair site will be observed. If exogenous DNA is also supplied, it will be inserted into the DSB during its repair by the NHEJ pathway.

Additional Description

Embodiments of the invention include a method, kit, use, or system comprising a fusion protein or proteinaceous fusion molecule that comprises a polypeptide possessing recombinase activity and a polypeptide DNA-binding domain. Another embodiment is the system assembled to be free of any DNA fragment that specifically binds to the polypeptide DNA-binding domain and/or further comprising an exogenous DNA that is not specifically bound to the fusion protein. The embodiments may be further comprising a single-stranded nucleic acid that forms a nucleoprotein filament by specifically binding to the polypeptide possessing recombinase activity. The recombinase may be a recombinase as set forth herein, e.g., RecA, recA803, uvsX, recA mutants, recA-like recombinases, RuvC, DST2, KEM1 and XRN1, STPa/DST1, and HPP-1. The polypeptide DNA-binding domain may be as set forth in this disclosure, e.g., may be chosen from the group consisting of Gal4, a nuclease, a zinc finger nuclease, a zinc finger, and a helix-turn-helix protein. The fusion molecule may further comprise a nuclear localization sequence (NLS). The exogenous DNA may comprise a DNA marker gene sequence. The exogenous DNA may encode a polypeptide to be expressed by a cell that receives the system. The exogenous DNA may be a marker for identification after insertion into a chromosome of a host cell that receives the system. The fusion molecule may further comprise a synthetic linker, optionally disposed between the polypeptide possessing recombinase activity and the polypeptide DNA-binding domain, for example a polyethylene oxide. The fusion protein may comprise RecA and/or Gal4.

Embodiments include a method, kit, use, or system for transfection of a target locus of a cell with an exogenous DNA fragment comprising: a fusion molecule that comprises a polypeptide possessing recombinase activity and a polypeptide DNA-binding domain, a single stranded DNA fragment with substantial homology to the locus (a probe), the fragment specifically binding to the polypeptide possessing recombinase activity to thereby form a filament, and an exogenous DNA fragment that is not specifically bound to the fusion protein, optionally wherein said exogenous DNA encodes a polypeptide for expression by the cell. The system of may be free of any DNA fragment that specifically binds to the polypeptide DNA-binding domain. The system may be provided wherein the exogenous DNA fragment is present in a molar concentration that exceeds the molar concentration of the fusion protein, with the excess optionally being at least 2-fold or between about 2-fold and 500-fold; artisans will immediately appreciate that all ranges and values between the explicitly stated values are contemplated, e.g., 10-fold or from about 5-fold to about 50-fold. The exogenous DNA fragment may encode a polypeptide for cellular expression and/or be free of a promoter sequence. The exogenous DNA fragment may encode a polypeptide for cellular expression and optionally include an expression cassette. The recombinase may be a recombinase as set forth herein. The polypeptide DNA-binding domain may be chosen from the group consisting of Gal4, a nuclease, a zinc finger nuclease, a zinc finger, and a helix-turn-helix protein. The fusion protein may further comprise a nuclear localization sequence (NLS). The exogenous DNA may be provided wherein it comprises a DNA marker gene sequence, encodes a polypeptide to be expressed by a cell that receives the system, or is a marker for identification after insertion into a chromosome of a host cell that receives the system. The fusion protein may further comprise a synthetic linker, optionally disposed between the polypeptide possessing recombinase activity and the polypeptide DNA-binding domain, for example a polyethylene oxide.

Embodiments include a method, kit, use, or system for transfecting a cell comprising exposing the cell to the system of any of 12-21 wherein a user chooses a target site in a chromosome of the cell, forms the filament, and administers the filament and the exogenous DNA to the cell, wherein the exogenous DNA is effectively placed within less than about 5000 basepairs of the target site; artisans will immediately appreciate that all the ranges and values within the explicitly stated ranges are contemplated, e.g., 0-5000, about 100 to about 1000, about 0 to about 500, less than 2000.

Embodiments include a method, kit, use, or system for transfection of a cell with an exogenous and substantially homologous DNA fragment comprising: a fusion molecule that comprises a polypeptide possessing recombinase activity and a polypeptide DNA-binding domain, a double stranded DNA fragment with at least one portion having a sequence of at least about 20 residues that has substantial homology to the locus, with the double stranded DNA fragment being free of specific biding to the fusion protein. The double-stranded DNA fragment may have at least two sequences of at least 20 residues that have substantial homology to the locus. The substantial homology may be an identity. The system may be free of any DNA fragment that specifically binds to the polypeptide DNA-binding domain. The system may be provided wherein the double-stranded DNA fragment is present in a molar concentration that exceeds the molar concentration of the fusion protein, with the excess optionally being at least 2-fold or between about 2-fold and 500-fold; artisans will immediately appreciate that all ranges and values between the explicitly stated values are contemplated, e.g., 10-fold or from about 5-fold to about 50-fold. The exogenous DNA fragment may encode a polypeptide for cellular expression. Thee polypeptide possessing recombinase may be a recombinase as set forth herein. The polypeptide DNA-binding domain may be as set forth herein, for example, chosen from the group consisting of Gal4, a nuclease, a zinc finger nuclease, a zinc finger, and a helix-turn-helix protein. The fusion protein may further comprise a nuclear localization sequence (NLS). The double-stranded DNA may comprises a DNA marker gene sequence, encode a polypeptide to be expressed by a cell that receives the system, or a marker for identification after insertion into a chromosome of a host cell that receives the system. The fusion protein may further comprise a synthetic linker, optionally disposed between the polypeptide possessing recombinase activity and the polypeptide DNA-binding domain, for example a polyethylene oxide. The homology may comprise homologous sequences located at the termini of the nucleic acid and/or internally in the first nucleic acid. Embodiments may include the case wherein the double-stranded DNA molecule has protruding single-stranded 3' ends. The polypeptide DNA-binding domain may comprise a Gal4 DNA-binding domain.

Embodiments include a method, kit, use, or system for targeted mutagenesis at or near a region of interest in a cellular nucleic acid sequence, the method comprising: (a) providing a nucleic acid molecule having homology to the region of interest; (b) binding a fusion molecule to the nucleic acid, wherein the fusion molecule comprises: (i) polypeptide sequences having RecA/Rad51 activity, and (ii) polypeptide sequences comprising a sequence-specific DNA-binding domain; and (c) introducing the protein-bound nucleic acid into the cell. The cellular nucleic acid sequence may be in a chromosome. The nucleic acid molecule may be DNA. The DNA may be single-stranded. The DNA may be double-stranded. The nucleic acid molecule may be RNA. The fusion molecule comprises polypeptide sequences having RecA activity. The sequence-specific DNA-binding domain may comprise a Gal4 DNA-binding domain. The fusion protein may further comprise a nuclear localization sequence (NLS). The targeted mutagenesis may be performed so that it results in conversion of a mutant sequence to a wild-type sequence. The targeted mutagenesis may be performed so that it results in conversion of a first allele/haplotype to a second allele/haplotype. The targeted mutagenesis may be performed to result in conversion of a wild-type sequence to a mutant sequence. The mutation may be selected from the group consisting of a point mutation, an insertion, a deletion, a translocation, and an inversion.

Embodiments include a method, kit, use, or system for targeted homologous recombination between a sequence of interest in cellular DNA and an exogenous double-stranded nucleic acid, the method comprising: (a) providing a linear double-stranded nucleic acid containing one or more regions homologous to the sequence of interest; (b) binding a fusion protein to the nucleic acid, wherein the fusion protein comprises: (i) polypeptide sequences having RecA/Rad51 activity, and (ii) polypeptide sequences comprising a sequence-specific DNA-binding domain and (c) introducing the protein-bound nucleic acid into the cell. The nucleic acid of step (a) may contain the regions homologous to the sequence of interest at both of its ends. Each of the regions of homology may be at least 10, 20, or 50 nucleotides in length. One or more regions homologous to the sequence of interest may be located internally in the nucleic acid of step (a). Further, the entire exogenous nucleic acid may be integrated into the cellular DNA. The cellular DNA may be, for example, in a chromosome, in an episome, comprised of sequences that encode a protein. The exogenous nucleic acid may further comprises regulatory sequences. The fusion protein may be provided so that it comprises polypeptide sequences having RecA activity. The sequence-specific DNA-binding domain may comprise the Gal4 DNA-binding domain. The fusion protein may further comprise a nuclear localization sequence (NLS). The nucleic acid of step (a) may be provided so that it does not contain a recognition site for a recombinase, transposase or integrase. The nucleic acid of step (a) may be free of any transposon or a viral genome. The recombination may be engineered so that it results in conversion of a mutant sequence to a wild-type sequence. The recombination may result in conversion of a first allele/haplotype to a second allele/haplotype. The recombination may result in conversion of a wild-type sequence to a mutant sequence. The mutation may be selected from, for example, the group consisting of a point mutation, an insertion, a deletion, a translocation and an inversion.

An embodiment is a fusion protein comprising: (a) polypeptide sequences having RecA/Rad51 activity, and (b) polypeptide sequences comprising a sequence-specific DNA-binding domain. The fusion protein may further comprise a nuclear localization sequence (NLS). Alternatively, the fusion molecule may be placed directly in the cell as described herein.

Embodiments include a method, kit, use, or system for stimulating gene conversion in a cell, the method comprising introducing, into the cell, a fusion molecule as set forth herein. An example is a proteinaceous fusion molecule comprising: (a) RecA; (b) a NLS; and (c) Gal4; wherein said gene conversion does not require hydrolysis of ATP.

Embodiments include a method, kit, use, or system for transfecting a cell comprising exposing the cell to an embodiment of such a system as set forth herein. Embodiments include a method, kit, use, or system for transfecting a cell comprising exposing the cell to the system as already described. Examples of cells are a vertebrate cell, a mammalian cell, a porcine cell, a human cell, a plant cell and a stem cell. Embodiments include a transgenic animal formed by the methods or systems described, e.g., a pig or artiodactyl or mini-pig, goat, rabbit, or mouse. The method, kit, use, or system may be free of a transposon and/or a viral genome. The materials may be provided in a pharmaceutically acceptable form or with a pharmaceutically acceptable excipient. The fusion molecules may be used to make therapeutic proteins in vitro or in vivo.

An embodiment is a method of transfecting a cell comprising introducing into the cell: an exogenous nucleic acid and a nucleoprotein filament of a proteinaceous fusion molecule and a nucleic acid probe complementary to a target site of DNA of the cell, wherein the fusion protein comprises a recombinase domain that contributes to the filament, and a DNA-binding domain, wherein the exogenous nucleic acid is incorporated into the DNA of the cell and expressed by the cell. An embodiment is a purified composition for transfection of exogenous DNA into chromosomal DNA of a cell, the composition comprising a nucleoprotein filament of a probe and a proteinaceous fusion molecule, wherein the probe comprises double-stranded denatured DNA complementary to a chromosomal DNA site, and the fusion molecule comprises a recombinase domain and a DNA-binding domain, wherein the composition is free of DNA sequences that specifically bind to the DNA-binding domain. An embodiment is a method of treating a genetic disease in an animal comprising introducing into a cell of the animal: an exogenous nucleic acid and a nucleoprotein filament of a proteinaceous fusion molecule and a nucleic acid probe complementary to a target site of DNA of the cell, wherein the fusion molecule comprises a recombinase domain that contributes to the filament, and a DNA-binding domain at the time of the introduction, wherein the exogenous nucleic acid is expressed by the cell to provide a therapeutic protein to the animal to treat the disease, the method is performed without a viral vector and without a transposon vector, and the cell is transfected by a method chosen from the group consisting of in vitro, in vivo, and ex vivo. The exogenous nucleic acid may be double-stranded DNA and may also be free of promoter sequences. The nucleic acid probe may be provided so that it comprises complementary single strand DNA (cssDNA) and the DNA-binding domain is not specifically bound to DNA at the time of the introduction. The exogenous nucleic acid site of insertion may be provided to be within about 1000 bases of the target site. Systems are provided with an efficiency of transfecting the cell of at least about 1%, as measured by an in vitro test with direct injection. The recombinase may be, or comprise RecA, or a functional fragment thereof. The DNA-binding domain may comprise Gal4. The recombinase may be a recombinase set forth herein, e.g., chosen from the group consisting of Cre recombinase, Hin recombinase, Tre recombinase, flippase recombination enzyme, uvsX, RuvC, DST2, KEM1 and XRN1, STPa/DST1, and HPP-1. The DNA-binding domain may comprise a polypeptide that specifically binds to DNA and is chosen from the group consisting of minor groove binders, major groove binders, antibiotics, intercalating agents, polyamides, and a polypeptide sequence of a transcription factor, nuclease, zinc finger nucleases, zinc fingers, and helix-turn-helix proteins. The fusion molecule may be chosen from the group consisting of SEQ ID NO:3, SEQ ID NO:5, and conservative substitutions thereof. The nuclear localization signal may be, e.g., an SV40 family member. The fusion molecule may comprise a synthetic non-peptide linker. The probe may be directed to a mutation in the cell DNA, and the exogenous nucleic acid comprises a wild-type sequence corresponding to the mutation. The exogenous nucleic acid may be non-homologous relative to the cell DNA. The fusion molecule may further comprise a nuclear localization signal domain. Cells may be transfected with the systems or methods, e.g., a vertebrate cell, a mammalian cell, a porcine cell, a human cell, a plant cell, and a stem cell. A transgenic animal may be formed by such methods, e.g., from progeny of a germline cell transfected by the method or systems; e.g., a pig or artiodactyl or mini-pig, goat, rabbit, or mouse. The method of introduction may be, e.g., chosen from the group consisting of electroporation, liposome, nuclear transplantation, Pronuclear microinjection, and somatic cell nuclear transfer. The probe may be directed to, for example, a mutated DNA of the animal that contributes to the disease.

TABLE I

Injection of complementary ssDNA-NLSRecAGal4 results in loss of heterozygocity at the gol (b1) locus

| | RecA type | Probe* | Dosage | Total | Total living | Normal dev. | Gol eye clones | |
|---|---|---|---|---|---|---|---|---|
| Injection | NLSRecAGal4 | css gsg1 | 45pg | 292 | 241 | N.D | 7/241 | 2.9% |
| | NLSRecAGal4 | ds gsg1 | 45pg | 284 | 237 | N.D | 0/237 | 0% |
| | NLSRecAGal4 | ss gsg2-F | 80pg | 155 | 136 | N.D | 0/136 | 0% |
| | NLSRecAGal4 | ss gsg2-R | 80pg | 258 | 224 | N.D | 0/224 | 0% |
| | NLSRecAGal4 | css gsg2 | 80pg | 278 | 201 | N.D | 5/201 | 2.5% |
| | No | css gbg1 | 160pg | 74 | 65 | 58 | 0/58 | 0% |
| | No | css gbg2 | 160pg | 227 | 208 | 150 | 0/150 | 0% |
| | No | ss gbg1F + gbg2R | 160pg | 75 | 68 | 68 | 0/68 | 0% |
| | No | ss gbg2F + gbg1R | 160pg | 82 | 71 | 70 | 0/70 | 0% |
| | No | css gbg1 + gbg2 | 160pg | 597 | 379 | 342 | 0/342 | 0% |
| | NLSRecAGal4 | css gbg1 | 160pg | 260 | 188 | 144 | 6/144 | 4.2% |
| | NLSRecAGal4 | css gbg2 | 160pg | 139 | 135 | 107 | 3/107 | 2.8% |
| | NLSRecAGal4 | ss gbg1F + gbg2R | 160pg | 222 | 197 | 190 | 0/190 | 0% |
| | NLSRecAGal4 | ss gbg2F + gbg1R | 160pg | 147 | 129 | 129 | 0/129 | 0% |
| | NLSRecAGal4 | css gbg1 + gbg2 | 160pg | 979 | 745 | 591 | 20/591 | 3.4% |
| | RecA | css gbg1 + gbg2 | 160pg | 317 | 233 | 206 | 0/206 | 0% |
| | NLSRecA | css gbg1 + gbg2 | 160pg | 301 | 253 | 220 | 0/220 | 0% |
| | NLSRecAGal4ΔDD | css gbg1 + gbg2 | 160pg | 396 | 341 | 296 | 3/296 | 1.0% |
| | NLSRecAGal4 | css flh oligos | 160pg | 298 | 268 | 255 | 0/255 | 0% |
| | NLSRecAGal4 | css prim oligos | 160pg | 411 | 314 | 300 | 0/300 | 0% |
| | NLSRecAGal4 | css vegfa oligos | 160pg | 542 | 337 | 307 | 0/307 | 0% |
| | NLSRecAGal4 | css 5'AmC6-gbg2 | 160pg | 152 | 109 | 67 | 2/67 | 3.0% |
| | NLSRecAGal4 | css 3'InvdT-gbg2 | 160pg | 393 | 318 | 236 | 9/236 | 3.8% |
| Non-injection | | | | 471 | 438 | N.D | 0/438 | 0% |

*ss: single strand DNA probe; ds: double strand DNA probe; css: complementary single strand DNA probe; gsg: gol probe with stop codon in the middle; gbg: gol probe without stop codon; 5'AmC6: 5'Amino modifier C6 block; 3'InvdT: 3'Inverted dT block
N.D: non-determination

TABLE II

NLSRecAGal4 directed somatic reporter gene expression into the golden, floating head and prominin-1

| | | Somatic reporter gene expression | | | Germline complementation test | |
|---|---|---|---|---|---|---|
| Targeting Gene | Probe type | Total embryos | Surviving | Fluorescence | Founder (%) | gol progeny (%) |
| golden | gol probe I (gol270bp) | 791* | 649 | 33 (5.1%) | 1/13 (7.7%) | 34/919 (3.7%) |
| | gol probe II (gol300bp) | 207 | 165 | 14 (8.5%) | 1/8 (12.5%) | 1/139 (0.7%) |
| floating head | flh250bp | 216 | 212 | 18 (8.5%) | | |
| prominin-I | prim200bp | 162 | 154 | 29 (18.8%) | | |

*Data were collected from three individual experiments

The invention claimed is:

1. A method of placing an exogenous nucleic acid into DNA of a cell comprising introducing into the cell:
   (i) an exogenous nucleic acid,
   (ii) a proteinaceous fusion molecule that comprises
      a recombinase domain,
      a protein-protein interaction domain, and
      a nuclear localization signal domain, and
   (iii) a single strand DNA probe complementary to a target site in DNA of the cell (cssDNA), with the probe and the recombinase domain complexed as a nucleoprotein filament at the time of the introduction into the cell,
   with the exogenous nucleic acid sequence being chosen for incorporation into the DNA of the cell and designed to be free of specific binding to the proteinaceous fusion molecule,
   wherein the exogenous nucleic acid is incorporated into the DNA of the cell and expressed by the cell,
   wherein the method is performed without introducing nucleic acids into the cell that have specific binding to the protein-protein interaction domain.

2. The method of claim 1 wherein the exogenous nucleic acid is double-stranded DNA and is free of promoter sequences.

3. The method of claim 1 wherein the exogenous nucleic acid site of insertion is in a gene.

4. The method of claim 1 wherein efficiency of introducing the exogenous DNA into the DNA of the cell is at least about 1%, as measured by an in vitro test with direct injection.

5. The method of claim 1 wherein the recombinase comprises RecA.

6. The method of claim 1 wherein the protein-protein interaction domain comprises a Gal4 protein-protein interaction domain.

7. The method of claim 1 wherein the recombinase is chosen from the group consisting of Cre recombinase, Hin recombinase, Tre recombinase, flippase recombination enzyme, uvsX, RuvC, DST2, KEM1 and XRN1, STPa/DST1, and HPP-1.

8. The method of claim 1 wherein the fusion molecule is chosen from the group consisting of SEQ ID NO:3 and SEQ ID NO:5.

9. The method of claim 1 wherein the nuclear localization signal is chosen from the group consisting of SV40 large T antigen, nucleoplasmin, HIV-1 Rev, and M9.

10. The method of claim 1 wherein the fusion molecule comprises a synthetic non-peptide linker.

11. The method of claim 1 wherein the probe is directed to a mutation in the cell DNA, and the exogenous nucleic acid comprises a wild-type sequence corresponding to the mutation.

12. The method of claim 1 wherein the exogenous nucleic acid is non-homologous relative to the cell DNA.

13. The method of claim 1 wherein the protein-protein interaction domain comprises a dimerization domain.

* * * * *

UNITED STATES PATENT AND TRADEMARK OFFICE
CERTIFICATE OF CORRECTION

PATENT NO. : 9,074,224 B2
APPLICATION NO. : 12/869232
DATED : July 7, 2015
INVENTOR(S) : Jeffrey J. Essner, Hsin-Kai Liao and Scott C. Fahrenkrug It is certified that error appears in the above-identified patent and that said Letters Patent is hereby corrected as shown below:

In the Specification

Column 1, delete Lines 20-24 and replace with the following:
--This invention was made with government support under RR025915 awarded by the National Institutes of Health. The government has certain rights in the invention.--

Signed and Sealed this
Sixteenth Day of April, 2024

Katherine Kelly Vidal
*Director of the United States Patent and Trademark Office*